US009782388B2

(12) United States Patent
Shaw et al.

(10) Patent No.: US 9,782,388 B2
(45) Date of Patent: Oct. 10, 2017

(54) BIS-CYCLIC GUANIDINE COMPOUND COMPOSITIONS, METHODS OF USE AND TREATMENT THEREOF

(71) Applicants: University of South Florida, Tampa, FL (US); Torey Pines Institute for Molecular Studies, Port St. Lucie, FL (US)

(72) Inventors: Lindsey Neil Shaw, Tampa, FL (US); Renee Marie Fleeman, Tampa, FL (US); Richard Allen Houghten, Vero Beach, FL (US); Marcello Angelo Giulianotti, Vero Beach, FL (US); Radleigh G. Santos, Coral Springs, FL (US); Adel Nefzi, Port Saint Lucie, FL (US)

(73) Assignees: University of South Florida, Tampa, FL (US); Torrey Pines Institute for Molecular Studies, Port St. Lucie, FL (US)

( * ) Notice: Subject to any disclaimer, the term of this patent is extended or adjusted under 35 U.S.C. 154(b) by 0 days.

(21) Appl. No.: 15/120,972

(22) PCT Filed: Feb. 19, 2015

(86) PCT No.: PCT/US2015/016609
§ 371 (c)(1),
(2) Date: Aug. 23, 2016

(87) PCT Pub. No.: WO2015/130547
PCT Pub. Date: Sep. 3, 2015

(65) Prior Publication Data
US 2017/0065564 A1    Mar. 9, 2017

Related U.S. Application Data

(60) Provisional application No. 61/944,254, filed on Feb. 25, 2014.

(51) Int. Cl.
*C07D 233/46* (2006.01)
*A61K 31/4178* (2006.01)
*A01N 43/50* (2006.01)

(52) U.S. Cl.
CPC .......... *A61K 31/4178* (2013.01); *A01N 43/50* (2013.01); *C07D 233/46* (2013.01)

(58) Field of Classification Search
CPC .......................... C07D 233/46; A61K 31/4178
See application file for complete search history.

(56) References Cited

U.S. PATENT DOCUMENTS

2012/0329871 A1   12/2012  McKinley et al.

FOREIGN PATENT DOCUMENTS

WO    WO02057224 A2    7/2002

OTHER PUBLICATIONS

Acharya et al., Journal of Combinatorial Chemistry, 2001, vol. 3, No. 6, pp. 578-589.*
Klevens, R. M.; Edwards, J. R.; Richards, C. L., Jr.; Horan, T. C.; Gaynes, R. P.; Pollock, D. A.; Cardo, D. M., Estimating health care-associated infections and deaths in U.S. hospitals, 2002. Public health reports 2007, 122 (2), 160-6.
Rice, L. B., Progress and challenges in implementing the research on ESKAPE pathogens. Infection control and hospital epidemiology : the official journal of the Society of Hospital Epidemiologists of America 2010, 31 Suppl 1, S7-10.
Jacobs, A. C.; Hood, I.; Boyd, K. L.; Olson, P. D.; Morrison, J. M.; Carson, S.; Sayood, K.; Iwen, P. C.; Skaar, E. P.; Dunman, P. M., Inactivation of Phospholipase D Diminishes Acinetobacter baumannii Pathogenesis. Infection and Immunity 2010, 78 (5), 1952-1962.
Kahrstrom, C. T., Entering a post-antibiotic era? Nat Rev Micro 2013, 11 (3), 146-146.
Boucher, Helen W.; Talbot, George H.; Bradley, John S.; Edwards, John E.; Gilbert, D.; Rice, Louis B.; Scheld, M.; Spellberg, B.; Bartlett, J., Bad Bugs, No Drugs: No ESKAPE! An Update from the Infectious Diseases Society of America. Clinical Infectious Diseases 2009, 48 (1), 1-12.
Arias, C. A.; Murray, B. E., Antibiotic-Resistant Bugs in the 21st Century—A Clinical Super-Challenge. New England Journal of Medicine 2009, 360 (5), 439-443.
Falagas, M. E.; Tansarli, G. S.; Karageorgopoulos, D. E.; Vardakas, K. Z., Deaths Attributable to Carbapenem-ResistantEnterobacteriaceaeInfections. Emerging Infectious Diseases 2014, 20 (7), 1170-1175.
Souli, M.; Galani, I.; Giamarellou, H., Emergence of extensively drug-resistant and pandrug-resistant Gram-negative bacilli in Europe. Euro surveillance : bulletin Europeen sur les maladies transmissibles = European communicable disease bulletin 2008, 13 (47).
Santos, R. G.; Appel, J. R.; Giulianotti, M. A.; Edwards, B. S.; Sklar, L. A.; Houghten, R. A.; Pinilla, C., The mathematics of a successful deconvolution: a quantitative assessment of mixture-based combinatorial libraries screened against two formylpeptide receptors. Molecules 2013, 18 (6), 6408-24.
Medina-Franco, J. L.; Martínez-Mayorga, K.; Bender, A.; Marín, R. M.; Giulianotti, M. A.; Pinilla, C.; Houghten, R. A., Characterization of Activity Landscapes Using 2D and 3D Similarity Methods:Consensus Activity Cliffs. Journal of Chemical Information and Modeling 2009, 49 (2), 477-491.
López-Vallejo, F.; Giulianotti, M. A.; Houghten, R. A.; Medina-Franco, J. L., Expanding the medicinally relevant chemical space with compound libraries. Drug Discovery Today 2012, 17 (13-14), 718-726.

(Continued)

*Primary Examiner* — Laura L. Stockton
(74) *Attorney, Agent, or Firm* — Thomas | Horstemeyer, LLP

(57) ABSTRACT

The present disclosure provides compositions including a bis-cyclic guanidine compound, pharmaceutical compositions including a bis-cyclic guanidine compound, methods of treatment of a condition {e.g., bacterial infection) or disease, methods of treatment using compositions or pharmaceutical compositions, and the like.

7 Claims, 12 Drawing Sheets

OTHER PUBLICATIONS

Zhou, Z.; Wei, D.; Guan, Y.; Zheng, A.; Zhong, J.-J., Extensive in vitro activity of guanidine hydrochloride polymer analogs against antibiotics-resistant clinically isolated strains. Materials Science and Engineering: C 2011, 31 (8), 1836-1843.

Kalia, J.; Swartz, K. J., Elucidating the Molecular Basis of Action of a Classic Drug: Guanidine Compounds as Inhibitors of Voltage-Gated Potassium Channels. Molecular Pharmacology 2011, 80 (6), 1085-1095.

Bera, S.; Zhanel, G. G.; Schweizer, F., Antibacterial activity of guanidinylated neomycin B- and kanamycin A-derived amphiphilic lipid conjugates. Journal of Antimicrobial Chemotherapy 2010, 65 (6), 1224-1227.

Ling, L. L.; Schneider, T.; Peoples, A. J.; Spoering, A. L.; Engels, I.; Conlon, B. P.; Mueller, A.; Schaberle, T. F.; Hughes, D. E.; Epstein, S.; Jones, M.; Lazarides, L.; Steadman, V. A.; Cohen, D. R.; Felix, C. R.; Fetterman, K. A.; Millett, W. P.; Nitti, A. G.; Zullo, A. M.; Chen, C.; Lewis, K., A new antibiotic kills pathogens without detectable resistance. Nature 2015.

Rideout, M. C.; Boldt, J. L.; Vahi-Ferguson, G.; Salamon, P.; Nefzi, A.; Ostresh, J. M.; Giulianotti, M.; Pinilla, C.; Segall, A. M., Potent antimicrobial small molecules screened as inhibitors of tyrosine recombinases and Holliday junction-resolving enzymes. Molecular Diversity 2011, 15 (4), 989-1005.

Hensler, M. E.; Bernstein, G.; Nizet, V.; Nefzi, A., Pyrrolidine bis-cyclic guanidines with antimicrobial activity against drug-resistant Gram-positive pathogens identified from a mixture-based combinatorial library. Bioorganic & medicinal chemistry letters 2006, 16 (19), 5073-5079.

Houghten, R. A.; Pinilla, C.; Giulianotti, M. A.; Appel, J. R.; Dooley, C. T.; Nefzi, A.; Ostresh, J. M.; Yu, Y.; Maggiora, G. M.; Medina-Franco, J. L.; Brunner, D.; Schneider, J., Strategies for the use of mixture-based synthetic combinatorial libraries: scaffold ranking, direct testing in vivo, and enhanced deconvolution by computational methods. Journal of combinatorial chemistry 2008, 10 (1), 3-19.

Minond, D.; Cudic, M.; Bionda, N.; Giulianotti, M.; Maida, L.; Houghten, R. A.; Fields, G. B., Discovery of Novel Inhibitors of a Disintegrin and Metalloprotease 17 (ADAM17) Using Glycosylated and Non-glycosylated Substrates. Journal of Biological Chemistry 2012, 287 (43), 36473-36487.

Reilley, K J.; Giulianotti, M.; Dooley, C. T.; Nefzi, A.; McLaughlin, J. P.; Houghten, R. A., Identification of two novel, potent, low-liability antinociceptive compounds from the direct in vivo screening of a large mixture-based combinatorial library. The AAPS journal 2010, 12 (3), 318-29.

Wu, J.; Zhang, Y.; Maida, L. E.; Santos, R. G.; Welmaker, G. S.; LaVoi, T. M.; Nefzi, A.; Yu, Y.; Houghten, R. A.; Toll, L.; Giulianotti, M. A., Scaffold ranking and positional scanning utilized in the discovery of nAChR-selective compounds suitable for optimization studies. Journal of medicinal chemistry 2013, 56 (24), 10103-17.

Ranjit, D. K.; Rideout, M. C.; Nefzi, A.; Ostresh, J. M.; Pinilla, C.; Segall, A. M., Small molecule functional analogs of peptides that inhibit lambda site-specific recombination and bind Holliday junctions. Bioorganic & medicinal chemistry letters 2010, 20 (15), 4531-4.

Mok, N. Y.; Brenk, R.; Brown, N., Increasing the Coverage of Medicinal Chemistry-Relevant Space in Commercial Fragments Screening. Journal of Chemical Information and Modeling 2014, 54 (1), 79-85.

Singh, N.; Guha, R.; Giulianotti, M. A.; Pinilla, C.; Houghten, R. A.; Medina-Franco, J. L., Chemoinformatic analysis of combinatorial libraries, drugs, natural products, and molecular libraries small molecule repository. Journal of chemical information and modeling 2009, 49 (4), 1010-24.

Maggiora, G. M., On outliers and activity cliffs—why QSAR often disappoints. Journal of chemical information and modeling 2006, 46 (4), 1535.

Shanmugasundaram, V. M., G. M. , Characterizing Property and ActiVity Landscapes Using an Information-Theoretic Approach. In 222nd American Chemical Society National Meeting, Chicago, IL, United States, 2001.

Medina-Franco, J. L., Scanning structure-activity relationships with structure-activity similarity and related maps: from consensus activity cliffs to selectivity switches. Journal of chemical information and modeling 2012, 52 (10), 2485-93.

Medina-Franco, J.; Martinez-Mayorga, K.; Giulianotti, M.; Houghten, R.; Pinilla, C., Visualization of the Chemical Space in Drug Discovery. Current Computer Aided-Drug Design 2008, 4 (4), 322-333.

Sastry, M.; Lowrie, J. F.; Dixon, S. L.; Sherman, W., Large-Scale Systematic Analysis of 2D Fingerprint Methods and Parameters to Improve Virtual Screening Enrichments. Journal of Chemical Information and Modeling 2010, 50 (5), 771-784.

Rogers, D.; Hahn, M., Extended-Connectivity Fingerprints. Journal of Chemical Information and Modeling 2010, 50 (5), 742-754.

Santos, R. G.; Giulianotti, M. A.; Houghten, R. A.; Medina-Franco, J. L., Conditional Probabilistic Analysis for Prediction of the Activity Landscape and Relative Compound Activities. Journal of Chemical Information and Modeling 2013, 53 (10), 2613-2625.

Stumpfe, D.; Hu, Y.; Dimova, D.; Bajorath, J., Recent Progress in Understanding Activity Cliffs and Their Utility in Medicinal Chemistry. Journal of Medicinal Chemistry 2014, 57 (1), 18-28.

Garvey, M. I.; Piddock, L. J. V., The Efflux Pump Inhibitor Reserpine Selects Multidrug-Resistant *Streptococcus pneumoniae* Strains That Overexpress the ABC Transporters PatA and PatB. Antimicrobial Agents and Chemotherapy 2008, 52 (5), 1677-1685.

Chen, M.; Yu, Q.; Sun, H., Novel Strategies for the Prevention and Treatment of Biofilm Related Infections. International Journal of Molecular Sciences 2013, 14 (9), 18488-18501.

Sanchez, C. J.; Mende, K.; Beckius, M. L.; Akers, K. S.; Romano, D. R.; Wenke, J. C.; Murray, C. K., Biofilm formation by clinical isolates and the implications in chronic infections. BMC Infectious Diseases 2013, 13 (1), 47.

Kristich, C. J.; Li, Y. H.; Cvitkovitch, D. G.; Dunny, G. M., Esp-independent biofilm formation by Enterococcus faecalis. Journal of bacteriology 2004, 186 (1), 154-63.

Nefzi, A.; Giulianotti, M. A.; Houghten, R. A., Solid-phase synthesis of bis-heterocyclic compounds from resin-bound orthogonally protected lysine. Journal of combinatorial chemistry 2001, 3 (1), 68-70.

Nefzi, A.; Ostresh, J. M.; Yu, Y.; Houghten, R. A., Combinatorial chemistry: libraries from libraries, the art of the diversity-oriented transformation of resin-bound peptides and chiral polyamides to low molecular weight acyclic and heterocyclic compounds. The Journal of organic chemistry 2004, 69 (11), 3603-9.

Houghten, R. A., General method for the rapid solid-phase synthesis of large numbers of peptides: specificity of antigen-antibody interaction at the level of individual amino acids. Proceedings of the National Academy of Sciences of the United States of America 1985, 82 (15), 5131-5.

Ostresh, J. M.; Schoner, C. C.; Hamashin, V. T.; Nefzi, A.; Meyer, J.-P.; Houghten, R. A., Solid-Phase Synthesis of Trisubstituted Bicyclic Guanidines via Cyclization of Reduced N-Acylated Dipeptides. The Journal of organic chemistry 1998, 63 (24), 8622-8623.

Nefzi, A.; Ostresh, J. M.; Houghten, R. A., Parallel solid phase synthesis of tetrasubstituted diethylenetriamines via selective amide alkylation and exhaustive reduction of N-acylated dipeptides. Tetrahedron 1999, 55 (2), 335-344.

Manku, S.; Laplante, C.; Kopac, D.; Chan, T.; Hall, D. G., A Mild and General Solid-Phase Method for the Synthesis of Chiral Polyamines. Solution Studies on the Cleavage of Borane-Amine Intermediates from the Reduction of Secondary Amides. The Journal of organic chemistry 2001, 66 (3), 874-885.

Houghten, R. A.; Pinilla, C.; Appel, J. R.; Blondelle, S. E.; Dooley, C. T.; Eichler, J.; Nefzi, A.; Ostresh, J. M., Mixture-based synthetic combinatorial libraries. Journal of medicinal chemistry 1999, 42 (19), 3743-78.

Pinilla, C.; Appel, J. R.; Blanc, P.; Houghten, R. A., Rapid identification of high affinity peptide ligands using positional scanning synthetic peptide combinatorial libraries. BioTechniques 1992, 13 (6), 901-5.

Acharya, A. N.; Ostresh, J. M.; Houghten, R. A., Determination of isokinetic ratios necessary for equimolar incorporation of carboxylic acids in the solid-phase synthesis of mixture-based combinatorial libraries. Biopolymers 2002, 65 (1), 32-9.

Ostresh, J. M.; Winkle, J. H.; Hamashin, V. T.; Houghten, R. A., Peptide libraries: determination of relative reaction rates of protected amino acids in competitive couplings. Biopolymers 1994, 34 (12), 1681-9.

Carroll, R. K.; Burda, W. N.; Roberts, J. C.; Peak, K. K.; Cannons, A. C.; Shaw, L. N., Draft Genome Sequence of Strain CBD-635, a Methicillin-Resistant *Staphylococcus aureus* USA100 Isolate. Genome announcements 2013, 1 (4).

Van Horn, K. S.; Burda, W. N.; Fleeman, R.; Shaw, L. N.; Manetsch, R., Antibacterial Activity of a Series ofN2,N4-Disubstituted Quinazoline-2,4-diamines. Journal of Medicinal Chemistry 2014, 57 (7), 3075-3093.

Beau, J.; Mahid, N.; Burda, W. N.; Harrington, L.; Shaw, L. N.; Mutka, T.; Kyle, D. E.; Barisic, B.; van Olphen, A.; Baker, B. J., Epigenetic Tailoring for the Production of Anti-Infective Cytosporones from the Marine Fungus *Leucostoma persoonii*. Marine Drugs 2012, 10 (12), 762-774.

Diep, B. A.; Gill, S. R.; Chang, R. F.; Phan, T. H.; Chen, J. H.; Davidson, M. G.; Lin, F.; Lin, J.; Carleton, H. A.; Mongodin, E. F.; Sensabaugh, G. F.; Perdreau-Remington, F., Complete genome sequence of USA300, an epidemic clone of community-acquired meticillin-resistant *Staphylococcus aureus*. Lancet 2006, 367 (9512), 731-9.

Kolar, S. L.; Nagarajan, V.; Oszmiana, A.; Rivera, F. E.; Miller, H. K.; Davenport, J. E.; Riordan, J. T.; Potempa, J.; Barber, D. S.; Koziel, J.; Elasri, M. O.; Shaw, L. N., NsaRS is a cell-envelope-stress-sensing two-component system of *Staphylococcus aureus*. Microbiology 2011, 157 (Pt 8), 2206-19.

Niu, Y.; Padhee, S.; Wu, H.; Bai, G.; Qiao, Q.; Hu, Y.; Harrington, L.; Burda, W. N.; Shaw, L. N.; Cao, C.; Cai, J., Lipo-γ-AApeptides as a New Class of Potent and Broad-Spectrum Antimicrobial Agents. Journal of Medicinal Chemistry 2012, 55 (8), 4003-4009.

Willett, P.; Barnard, J. M.; Downs, G. M., Chemical Similarity Searching. Journal of Chemical Information and Modeling 1998, 38 (6), 983-996.

Perez-Villanueva, J.; Santos, R.; Hernandez-Campos, A.; Giulianotti, M. A.; Castillo, R.; Medina-Franco, J. L., Towards a systematic characterization of the antiprotozoal activity landscape of benzimidazole derivatives. Bioorganic & medicinal chemistry 2010, 18 (21), 7380-91.

Nefzi, Adel, et al. "Parallel synthesis of chiral pentaamines and pyrrolidine containing bis-heterocyclic libraries. Multiple scaffolds with multiple building blocks: A double diversity for the identification of new antitubercular compounds." Bioorganic & medicinal chemistry letters 19.17 (2009): pp. 5160-5175.

Fleeman, Renee, et al. "Combinatorial libraries as a tool for the discovery of novel, broad-spectrum antibacterial agents targeting the ESKAPE pathogens." Journal of medicinal chemistry 58.8 (2015): 3340-3355. published online Mar. 17, 2015.

International Search Report and Written Opinion for PCT/US2015/016609 dated Feb. 19, 2015.

* cited by examiner

| | R1 + R3 | | R2 |
|---|---|---|---|
| 1 | Hydrogen | a | S-methyl |
| 2 | 2-phenylbutyl | b | S-benzyl |
| 3 | 3-phenylbutyl | c | hydrogen |
| 4 | m-tolylethyl | d | S-2-butyl |
| 5 | 2-(3-fluoro-phenyl)-ethyl | e | S-isobutyl |
| 6 | 2-(3-bromo-phenyl)-ethyl | f | R-hydroxymethyl |
| 7 | 2-(3-trifluoromethyl-phenyl)-ethyl | g | (R,R)-1-hydroxyethyl |
| 8 | p-tolylethyl | h | S-isopropyl |
| 9 | 2-(4-fluoro-phenyl)-ethyl | i | S-4-hydroxybenzyl |
| 10 | 2-(3-methoxy-phenyl)-ethyl | j | R-methyl |
| 11 | 2-(4-bromo-phenyl)-ethyl | k | R-benzyl |
| 12 | 2-(4-methoxy-phenyl)-ethyl | l | R-2-butyl |
| 13 | 2-(4-ethoxy-phenyl)-ethyl | m | R-isobutyl |
| 14 | 2-(4-Isobutyl-phenyl)-propyl | n | S-hydroxymethyl |
| 15 | 3,4-dichlorophenethyl | o | (S,S)-1-hydroxyethyl |
| 16 | 2-(3,5-bis-trifluoromethyl-phenyl)-ethyl | p | R-isopropyl |
| 17 | 3-(3,4-dimethoxy-phenyl)-propyl | q | R-4-hydroxybenzyl |
| 18 | phenethyl | r | S-phenyl |
| 19 | 3,4,5-trimethoxy-benzyl | s | S-propyl |
| 20 | butyl | t | R-propyl |
| 21 | heptyl | u | S-butyl |
| 22 | isobutyl | v | R-butyl |
| 23 | 2-methylbutyl | w | S-2-naphthylmethyl |
| 24 | 3-methylbutyl | x | R-2-naphthylmethyl |
| 25 | 3-methylpentyl | y | S-cylcohexylmethyl |
| 26 | 4-methylpentyl | z | R-cylcohexylmethyl |
| 27 | 4-methyl-benzyl | | |
| 28 | cyclopently-methyl | | |
| 29 | cyclohexyl-methyl | | |
| 30 | cyclohexyl-ethyl | | |
| 31 | cyclohexyl-butyl | | |
| 32 | cycloheptyl-methyl | | |
| 33 | 2-methylcyclopropyl-methyl | | |
| 34 | cyclobutyl-methyl | | |
| 35 | 3-cyclopentyl-propyl | | |
| 36 | cyclohexyl-propyl | | |
| 37 | 4-methyl-1-cyclohexyl-methyl | | |
| 38 | 4-tert-butyl-cyclohexyl-methyl | | |
| 39 | 2-Biphenyl-4-yl-ethyl | | |
| 40 | adamantan-1-yl-methyl | | |
| 41 | adamantan-1-yl-ethyl | | |
| 42 | 2-Bicyclo[2.2.1]hept-2-yl-ethyl | | |

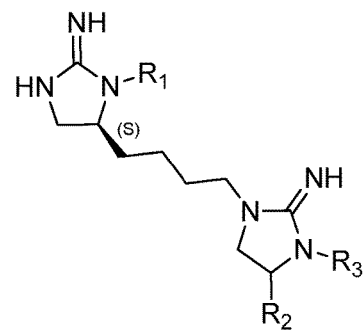

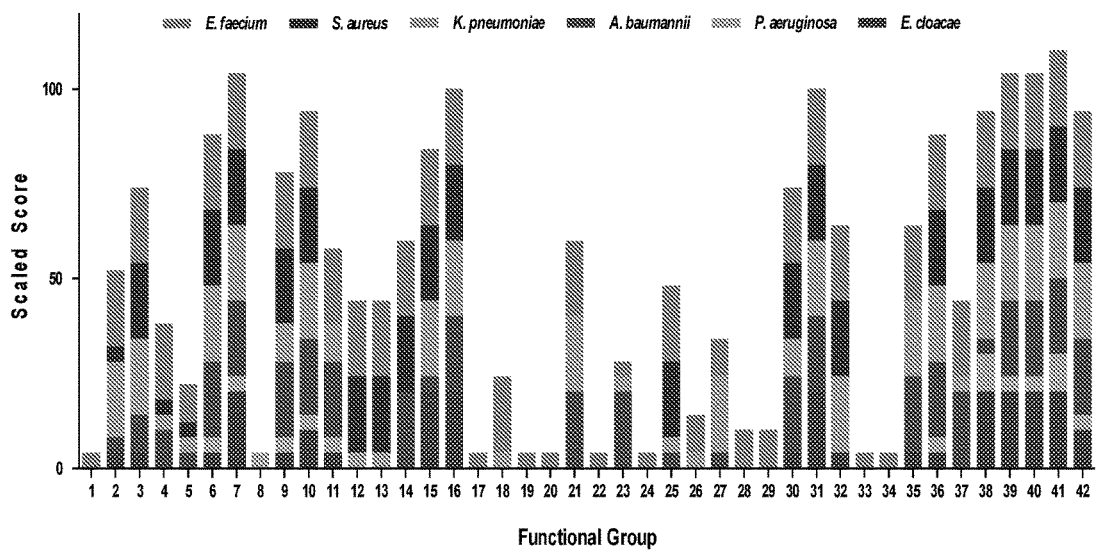

BIS-CYCLIC GUANIDINE COMPOUND COMPOSITIONS, METHODS OF USE AND TREATMENT THEREOF

CLAIM OF PRIORITY TO RELATED APPLICATION

This application claims priority to U.S. provisional application entitled "COMPOSITIONS INCLUDING A BIS-CYCLIC GUANIDINE COMPOUND, METHODS OF USE, AND METHODS OF TREATMENT" having Ser. No. 61/944,254, filed on Feb. 25, 2014, which is entirely incorporated herein by reference.

BACKGROUND

In spite of the rapid and continued emergence of drug resistant ESKAPE pathogen isolates, there has been an alarming decline in drug discovery efforts in the pharmaceutical industry. Thus, there is a need to develop drugs to treat infections for pathogens such as ESKAPE pathogen isolates.

SUMMARY

The present disclosure provides compositions including a bis-cyclic guanidine compound, pharmaceutical compositions including a bis-cyclic guanidine compound, methods of treatment of a condition (e.g., bacterial infection) or disease, methods of treatment using compositions or pharmaceutical compositions, and the like.

An embodiment of the present disclosure includes a pharmaceutical composition, among others, that includes: a therapeutically effective amount of a bis-cyclic guanidine compound, or a pharmaceutically acceptable salt of bis-cyclic guanidine compound, and a pharmaceutically acceptable carrier, to treat an infection, wherein the bis-cyclic guanidine compound has the following structure:

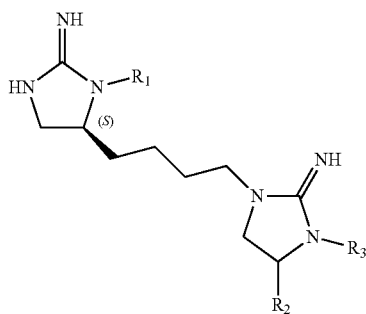

R1 is selected from the group consisting of: 2-(3-trifluoromethyl-phenyl)-ethyl, cyclohexyl-butyl, and adamantan-1-yl-ethyl; R2 is selected from the group consisting of: (S or R)-butyl, (S or R)-2-naphthylmethyl, (S or R)-cyclohexylmethyl; and R3 is selected from the group consisting of: heptyl, cyclohexyl-butyl, and 2-Biphenyl-4-yl-ethyl. In particular, the bis-cyclic guanidine compound is selected from one of the following structures:

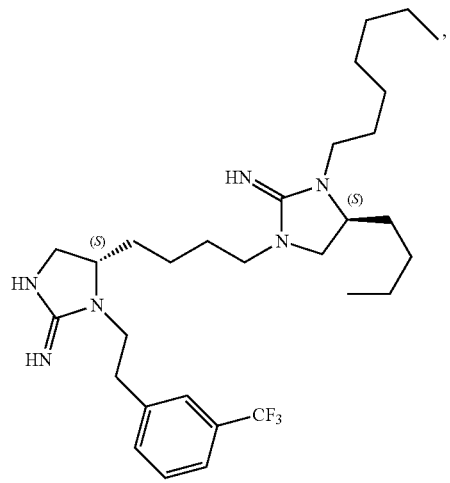

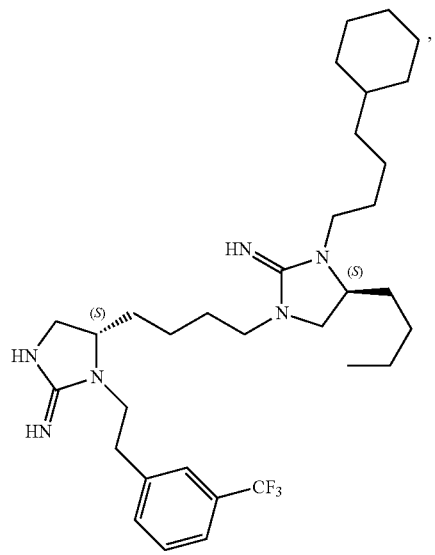

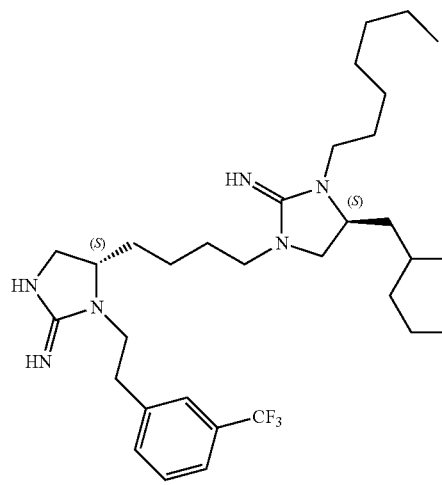

-continued

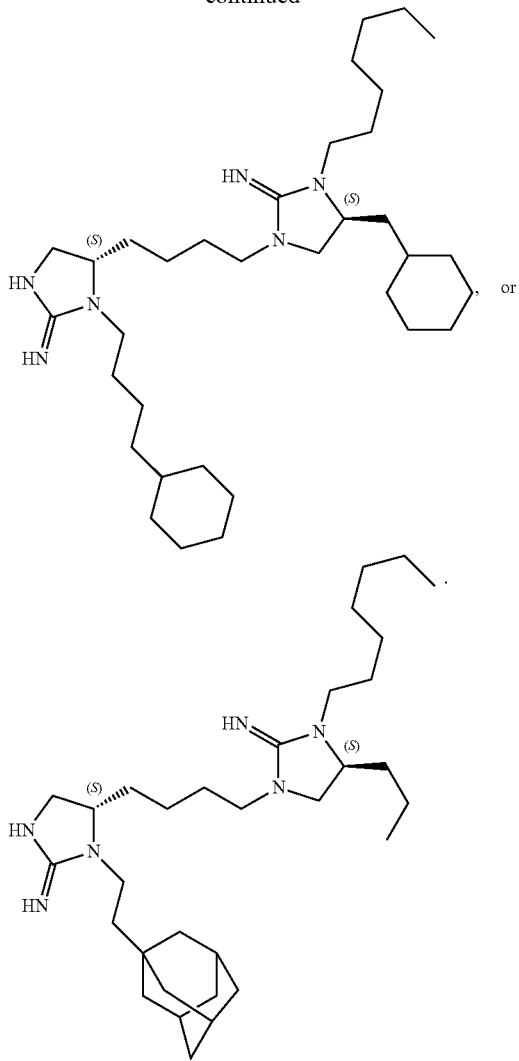

An embodiment of the present disclosure includes a method of treating an infection, among others, that includes: delivering to a subject in need thereof, a pharmaceutical composition, wherein the pharmaceutical composition includes a therapeutically effective amount of a bis-cyclic guanidine compound, or a pharmaceutically acceptable salt of the bis-cyclic guanidine compound, and a pharmaceutically acceptable carrier, to treat the infection, wherein the bis-cyclic guanidine compound has a structure such as those described herein. In an embodiment, the pharmaceutical composition is a broad spectrum antibiotic. In an embodiment, the infection is caused by one or more bacteria selected from the group consisting of: *Enterococcus faecium, Staphylococcus aureus, Klebsiella pneumoniae, Acinetobacter baumannii, Pseudomonas aeruginosa*, and *Enterobacter cloacae*.

An embodiment of the present disclosure includes a method of inhibiting the growth of a biofilm or the growth of bacteria, among others, that includes: exposing a surface having a biofilm thereon or exposed to bacteria to a composition comprising a bis-cyclic guanidine compound, wherein the bis-cyclic guanidine compound has a structure as described herein.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

FIGS. 2A-2C are graphs illustrating deconvolving the antibacterial activity of the bis-cyclic guanidine library. The bis-cyclic guanidines were systematically synthesized into a positional scanning library containing 110 samples (shown in supplemental table S2). These were fixed at: FIG. 2A=the $R_1$ (42 samples); FIG. 2B=$R_2$ (26 samples); or FIG. 2C=$R_3$ (42 samples) position. For example, the first sample in FIG. 2A, is an approximate equal molar mixture of 1,092 compounds. The 1,092 compounds contain hydrogen fixed in the $R_1$ position and all 1,092 combinations of the 26 $R_2$ and 42 $R_3$ functionalities. Similarly, the first sample in FIG. 2B is 1,764 compounds generated from fixing $R_2$ with S-methyl and utilizing all 1,764 combinations of the 42 $R_1$ and 42 $R_3$ functionalities. The height for each color of individual bars is determined by dividing 100 μM (the maximum concentration tested) by the individual MIC for each agent. Libraries are then given a scaled score for each pathogen, and these are stacked to determine the library with the broadest activity, at the lowest concentration.

FIG. 6A is a graph that illustrates time kill studies were performed using MRSA and the front runner agents (at MIC concentrations), alongside positive (4 μM lysostaphin, 0.001% Benzalkonium chloride (BA), 0.001% Benzethonium chloride (BC), and 2.0% Sodium dodecyl sulfate (SDS)), and negative (200 μM Doxycyline (Doxy)) control agents. Shown is the optical density of cells relative to starting values from three independent experiments. Error bars are shown ±SEM. FIG. 6B is a graph illustrating cell viability of all samples after the 120 min experiment. Compounds were removed by centrifugation and washing of cells, followed by serial dilution and enumeration. Percent recovery was determined by comparison to no drug (ND) controls.

Figure 12:
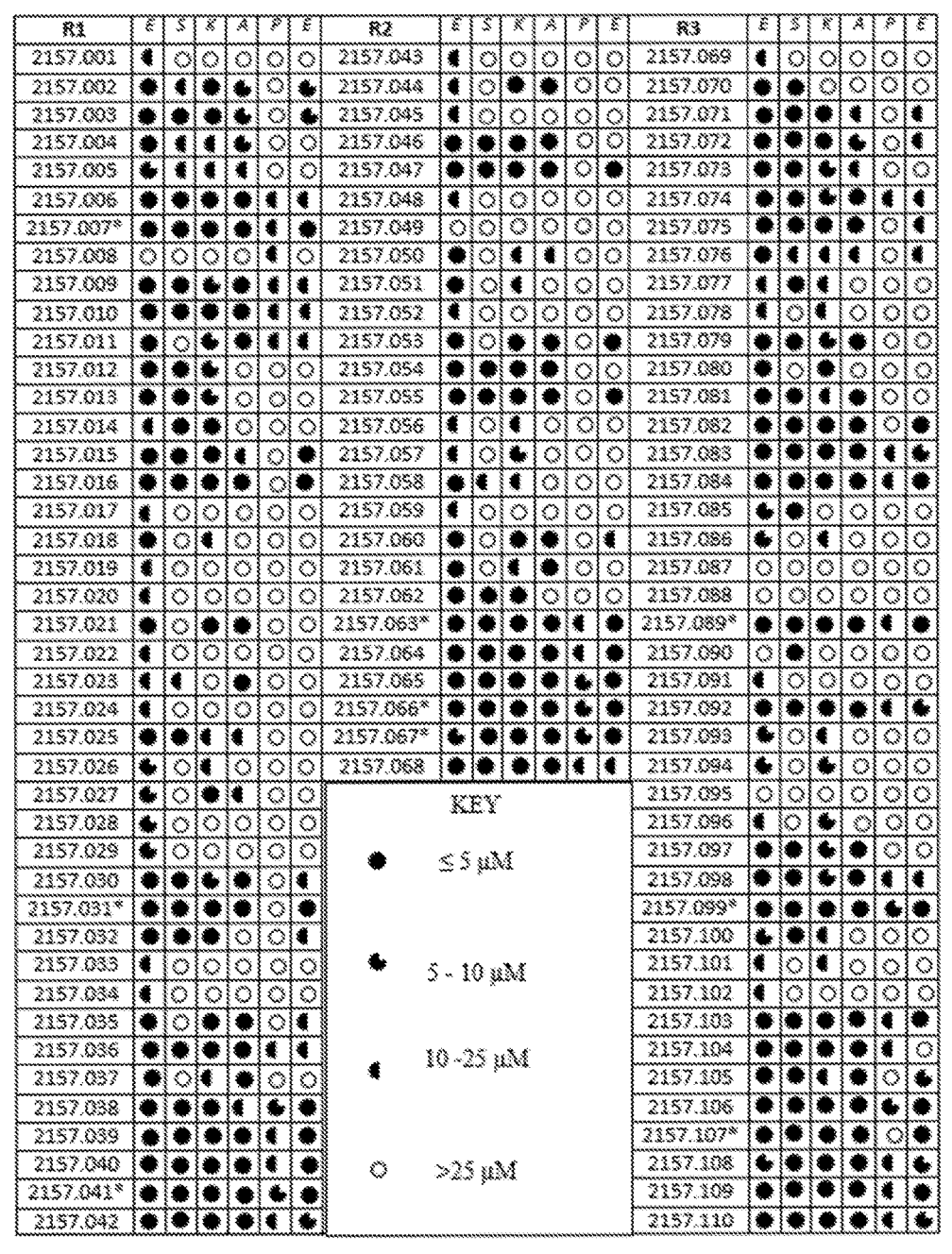

FIG. 12 is a table showing minimal inhibitory concentrations of the deconvolved 2157 libraries against the ESKAPE pathogens. Derivation of the functional groups for each compound can be found by referencing supplemental table S2. Compounds marked with an asterisk (*) denote those used to synthesize the 27 new agents in Supplemental Table S4 (1-27).

DISCUSSION

Figure 1:
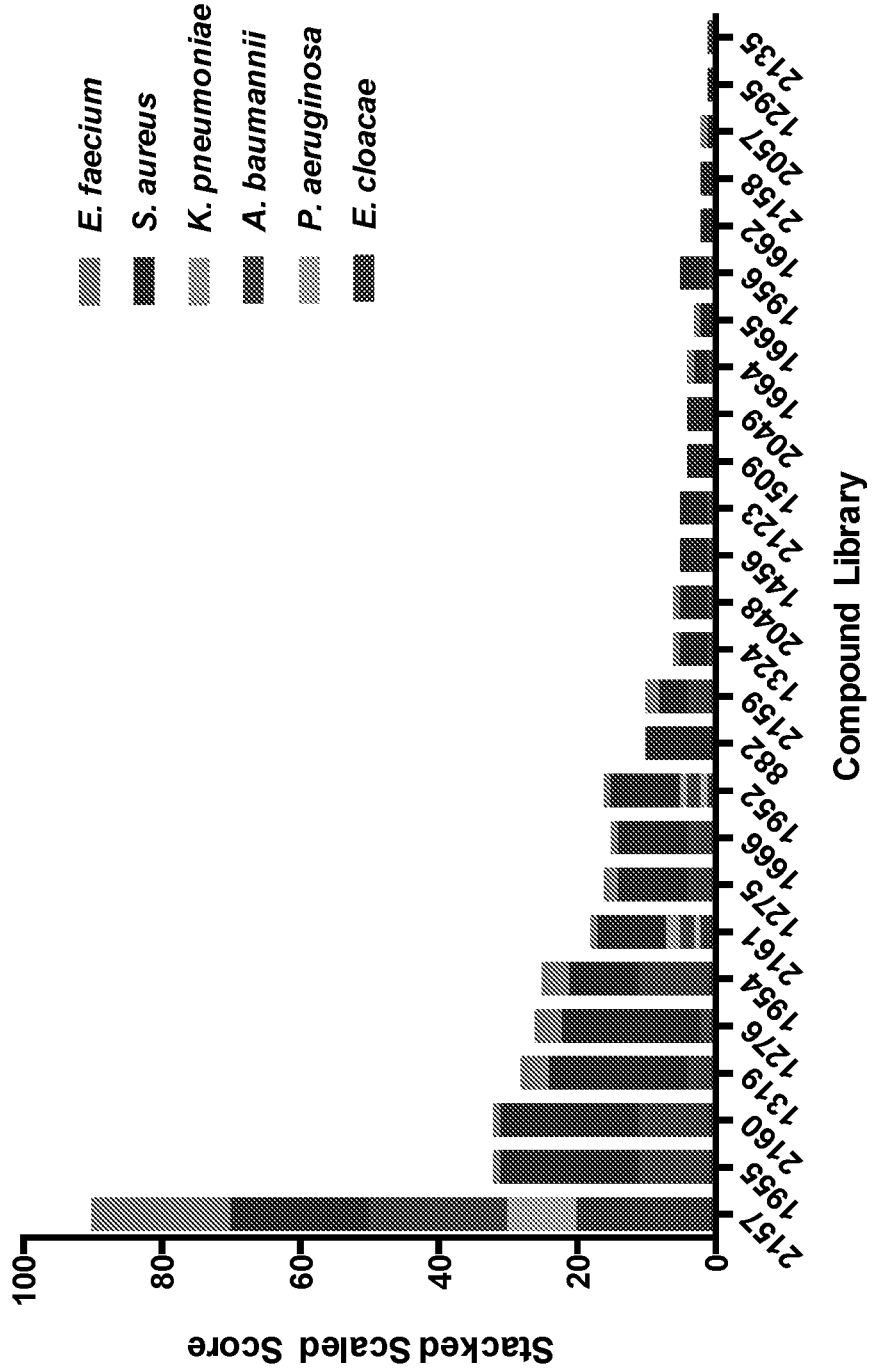
FIG. 1 is a graph illustrating screening the scaffold ranking library for antibacterial activity against the ESKAPE pathogens. Compound mixtures were assayed against the ESKAPE pathogens using a micro broth dilution assay. Data is presented as a stacked scaled score, which is determined by dividing 100 μM (the maximum concentration tested) by the individual doses tested. Each library is given a scaled score for each pathogen, and these are then stacked to determine the library with the broadest activity, at the lowest concentration.

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

Definitions

Unless otherwise defined, all technical and scientific terms used herein have the same meaning as commonly understood by one of ordinary skill in the art of molecular biology, medicinal chemistry, and/or organic chemistry.

Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

The term "substituted" refers to any one or more hydrogens on the designated atom that can be replaced with a selection from the indicated group, provided that the designated atom's normal valence is not exceeded, and that the substitution results in a stable compound. In an embodiment, one or more of the hydrogens can be substituted with a halogen, an alkyl group (unsubstituted or substituted), a cycloalkyl group (unsubstituted or substituted), an aryl group (unsubstituted or substituted), and the like. In particular, the term "substituted," as in "substituted alkyl", "substituted cycloalkyl," substituted aryl," and the like, means that the substituted group may contain in place of one or more hydrogens a group such as a halogen, an alkyl group (unsubstituted or substituted), a cycloalkyl group (unsubstituted or substituted), an aryl group (unsubstituted or substituted), and the like.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, and s-pentyl. The term "lower alkyl" means an alkyl group having less than 10 carbon atoms.

As used herein, "alkenyl" or "alkenyl group" refers to an aliphatic hydrocarbon radical which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "arylalkyl" refers to an arylalkyl group wherein the aryl and alkyl are as herein described. Examples of arylalkyl include, but are not limited to, -phenylmethyl, phenylethyl, -phenylpropyl, -phenylbutyl, and -phenylpentyl.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. The term "lower alkoxy" means an alkoxy group having less than 10 carbon atoms.

The term "cycloalkyl" refers to a non-aromatic mono- or multicyclic ring system of about 3 to about 10 carbon atoms, preferably of about 5 to about 10 carbon atoms. Preferred ring sizes of rings of the ring system include about 5 to about 6 ring atoms. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

The term "cycloalkenyl" refers to a non-aromatic mono- or multicyclic ring system of about 3 to about 10 carbon atoms, preferably of about 5 to about 10 carbon atoms, and which contains at least one carbon-carbon double bond. Preferred ring sizes of rings of the ring system include about 5 to about 6 ring atoms. Exemplary monocyclic cycloalkenyl include cyclopentenyl, cyclohexenyl, cycloheptenyl, and the like. An exemplary multicyclic cycloalkenyl is norbornylenyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, indazolyl, quinolyl, isoquinolyl, quinoxalyl, and quinazolinyl. Preferred examples are furanyl, indazolyl, imidazyl, pyranyl, pyrrolyl, and pyridyl.

The term "biaryl" refers to an aryl, as defined above, where two aryl groups are joined by a direct bond or through an intervening alkyl group, preferably a lower alkyl group.

The term "fused aryl" refers to a multicyclic ring system as included in the term "aryl," and includes aryl groups and heteroaryl groups that are condensed. Examples are naphthyl, anthryl and phenanthryl. The bonds can be attached to any of the rings.

"Aralkyl" and "heteroaralkyl" refer to aryl and heteroaryl moieties, respectively, that are linked to a main structure by an intervening alkyl group, e.g., containing one or more methylene groups.

The term "fluorobenzyl" refers to a benzyl group wherein the phenyl moiety is substituted with one or more fluorine atoms, including 2, 3, 4 and 5 fluorine atom substituents.

Similarly, "halobenzyl" refers to benzyl substituted with one or more different halogens, including fluorine, chlorine, bromine, and iodine (not astatine).

The terms "sulfide" and "thioether" as used herein, alone or in combination, refer to a sulfur atom covalently linked to two atoms; the formal oxidation state of said sulfur is (II). These terms may be used interchangeably.

The term "sulfanyl" as used herein, alone or in combination, refers to the —S—R group, wherein R may be a group such as: alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. Non-limiting examples of sulfanyl groups include methylsulfanyl (—$SCH_3$) and iso-propylsulfanyl (—$SCH(CH_3)_2$) and the like.

The term "sulfoxide" as used herein, alone or in combination, refers to a sulfur atom covalently linked to three atoms, at least one of which is an oxygen atom; the formal oxidation state of said sulfur atom is (IV).

The term "sulfinyl" as used herein, alone or in combination, refers to the groups —S(O)—R, wherein R may be, but is not limited to alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. A non-limiting example of a sulfinyl group includes methylsulfinyl (—S(O)CH$_3$) and the like.

The term "sulfone" as used herein, alone or in combination, refers to a sulfur atom covalently linked to four atoms, at least two of which are oxygen atoms; the formal oxidation state of said sulfur atom is (VI).

The term "sulfonyl" as used herein, alone or in combination, refers to the groups —S(O$_2$)—R, wherein R may be, but is not limited to, alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. A non-limiting example of a sulfonyl group includes methylsulfonyl (—S(O$_2$)CH$_3$) and the like.

The term "phosphite" as used herein, alone or in combination, refers to a phosphorus atom covalently linked to three carbon atoms, wherein the formal oxidation state of said phosphorus is (III).

The term "phosphinyl" as used herein, alone or in combination, refers to the monoradical derived from a phosphite group, as defined above.

The term "phosphonate" as used herein, alone or in combination, refers to a phosphorus atom covalently linked to four atoms, three of which are oxygen and one of which is carbon wherein the formal oxidation state of said phosphorus is (V).

The term "phosphonyl" as used herein, alone or in combination, refers to the monoradical derived from a phosphonate group, as defined above.

The term "phosphate" as used herein, alone or in combination, refers to a phosphorus atom covalently linked to four oxygen atoms, wherein the formal oxidation state of said phosphorus is (V).

The term "phosphatidyl" as used herein, alone or in combination, refers to the monoradical derived from a phosphate group, as defined above.

The terms ketone, ester, ether, and acyl have their art recognized meanings.

The term "unit dosage form," as used herein, refers to physically discrete units suitable as unitary dosages for human and/or animal subjects, each unit containing a predetermined quantity of a compound (e.g., compositions or pharmaceutical compositions, as described herein) calculated in an amount sufficient to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the subject.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one and more such excipients, diluents, carriers, and adjuvants.

As used herein, a "pharmaceutical composition" is meant to encompass a composition or pharmaceutical composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The term "therapeutically effective amount" as used herein refers to that amount of an embodiment of the composition or pharmaceutical composition being administered that will relieve to some extent one or more of the symptoms of the disease, i.e., infection, being treated, and/or that amount that will prevent, to some extent, one or more of the symptoms of the disease, i.e., infection, that the subject being treated has or is at risk of developing.

"Pharmaceutically acceptable salt" refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

In the event that embodiments of the disclosed compounds in the composition or pharmaceutical composition form salts, these salts are within the scope of the present disclosure. Reference to a compound used in the composition or pharmaceutical composition of any of the formulas herein is understood to include reference to salts thereof, unless otherwise indicated. The term "salt(s)", as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of a compound may be formed, for example, by reacting the compound with an amount of acid or base, such as an equivalent amount, in a medium such as one in which the salt precipitates or in an aqueous medium followed by lyophilization.

Embodiments of the compounds of the composition or pharmaceutical composition of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the compounds of the composition or pharmaceutical composition of the present disclosure that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the composition or pharmaceutical composition of the present disclosure are also contemplated herein.

To the extent that the disclosed the compounds of the composition or pharmaceutical composition of the present disclosure, and salts thereof, may exist in their tautomeric form, all such tautomeric forms are contemplated herein as part of the present disclosure.

All stereoisomers of the compounds of the composition or pharmaceutical composition of the present disclosure, such as those that may exist due to asymmetric carbons on the various substituents, including enantiomeric forms (which may exist even in the absence of asymmetric carbons) and diastereomeric forms are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of the compounds of the composition or pharmaceutical composition of the present disclosure that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of 3-Lactam antibiotics, Pharm. Biotech. 11, 345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3):183-209; Browne (1997). Fosphenytoin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The term "administration" refers to introducing a composition of the present disclosure into a subject. One preferred route of administration of the composition is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

As used herein, "treat", "treatment", "treating", and the like refer to acting upon a condition (e.g., bacterial infection), a disease or a disorder with a composition to affect the condition, disease or disorder by improving or altering it. The improvement or alteration may include an improvement in symptoms or an alteration in the physiologic pathways associated with the condition, disease, or disorder. "Treatment," as used herein, covers one or more treatments of a condition or a disease in a subject (e.g., a mammal, typically a human or non-human animal of veterinary interest), and includes: (a) reducing the risk of occurrence of the infection in a subject determined to be predisposed to the condition or disease but not yet diagnosed with it (b) impeding the development of the infection, and/or (c) relieving the infection, e.g., causing regression of the infection and/or relieving one or more infection symptoms.

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition (e.g., infection), a disease, or a symptom thereof and/or may be therapeutic in terms of a partial or complete cure for a infection, and/or adverse effect attributable to the infection.

As used herein, the term "subject," or "patient," includes humans and mammals (e.g., mice, rats, pigs, cats, dogs, and horses). Typical subjects to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living subject" refers to a subject noted above or another organism that is alive. The term "living subject" refers to the entire subject or organism and not just a part excised (e.g., a liver or other organ) from the living subject.

As used herein, "biofilms" refer to biological films that develop and persist at interfaces in aqueous environments, especially along the inner walls of conduit material in industrial facilities, in household plumbing systems, on medical implants, or as foci of chronic infections. These biological films are composed of microorganisms embedded in an organic gelatinous structure composed of one or more matrix polymers that are secreted by the resident microorganisms. Biofilms can develop into macroscopic structures several millimeters or centimeters in thickness and can cover large surface areas. These biological formations can play a role in restricting or entirely blocking flow in plumbing systems and often decrease the lifespan or longevity of materials through corrosive action mediated by the embedded bacteria. Biofilms are also capable of trapping nutrients and particulates that can contribute to their enhanced development and stability. Biofilms can also prevent penetration of antimicrobial agents and therefore, make bacteria within biofilms drug resistant, which leads to persistent infection. Embodiments of the present disclosure can be used to inhibit the growth of a biofilm, where inhibits includes one or more of the following: stopping the growth of the biofilm, killing the biofilm, reducing the size of the biofilm, and the like.

Discussion:

The present disclosure provides compositions including a bis-cyclic guanidine compound, pharmaceutical compositions including a bis-cyclic guanidine compound, methods of treatment of a condition (e.g., bacterial infection) or disease, methods of treatment using compositions or pharmaceutical compositions, and the like.

An embodiment of the present disclosure can be used individually or in combination (e.g., in the same composition or separately) with other antibiotics to treat one or multiple strains of bacteria. Embodiments of the present disclose can be used as a broad spectrum antibiotic. In an embodiment, compositions of the present disclosure can be used to treat subjects having infections caused by bacteria such: *Enterococcus faecium, Staphylococcus aureus, Klebsiella pneumoniae, Acinetobacter baumannii, Pseudomonas aeruginosa, Enterobacter cloacae*, or combinations thereof. In addition, embodiments of the present disclosure can be used to inhibit biofilm growth on a surface or growth of bacteria on a surface. Additional details are described in the Examples.

An embodiment of the present disclosure includes a composition and a pharmaceutical composition including a bis-cyclic guanidine compound. In an embodiment, the pharmaceutical composition and the method of treatment (e.g., of an infection such as one directly or indirectly caused by a bacterial infection) includes a therapeutically effective amount of a bis-cyclic guanidine compound, or a pharmaceutically acceptable salt of the bis-cyclic guanidine compound, and a pharmaceutically acceptable carrier, to treat the bacterial infection.

In an embodiment, the bis-cyclic guanidine compound can include the following structure:

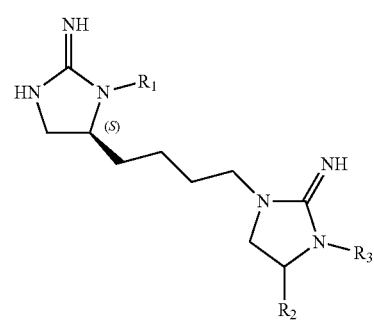

or a pharmaceutically acceptable salt thereof. In an embodiment, R1 can be: 2-(3-trifluoromethyl-phenyl)-ethyl, cyclohexyl-butyl, or adamantan-1-yl-ethyl. In an embodiment, R2 can be: (S or R)-butyl, (S or R)-2-naphthylmethyl, or (S or R)-cyclohexylmethyl (S or R configuration are defined by the IUPAC 1974 Recommendations). In an embodiment, R3 can be: heptyl, cyclohexyl-butyl, or 2-Biphenyl-4-yl-ethyl.

In an embodiment, the bis-cyclic guanidine compound can be one of the following structures:

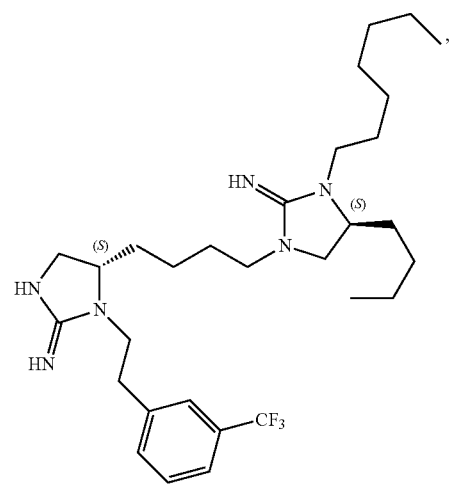

-continued

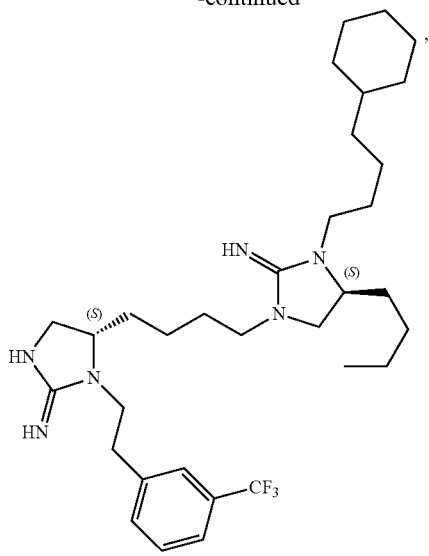

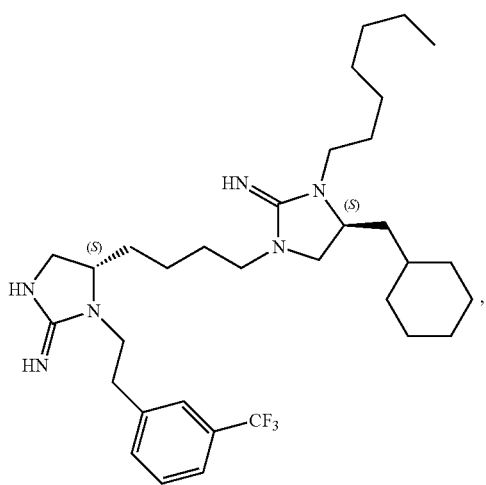

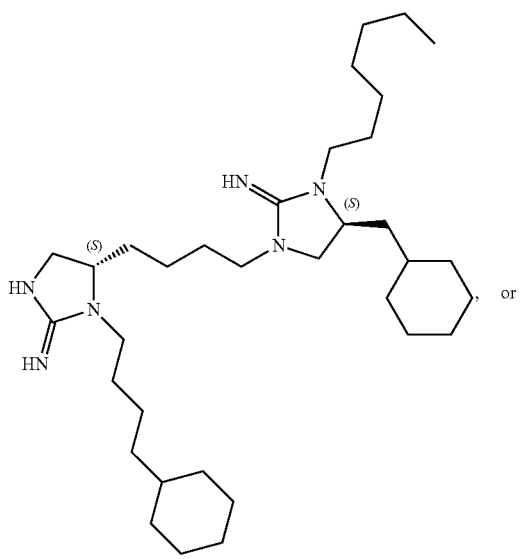, or

-continued

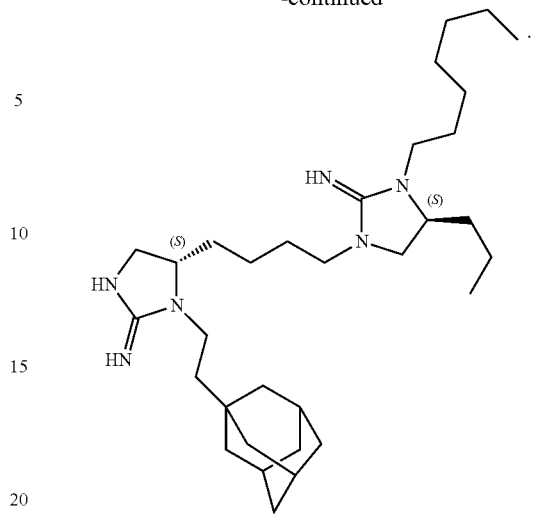

In an embodiment, the method includes treating a subject having an infection, in particular, a bacterial infection. The method can include delivering to a subject in need thereof, a pharmaceutical composition that includes a therapeutically effective amount of a bis-cyclic guanidine compound, or a pharmaceutically acceptable salt of the bis-cyclic guanidine compound, and a pharmaceutically acceptable carrier, to treat the infection. Embodiments of the bis-cyclic guanidine compound are described herein. In an embodiment the bacterial infections can be caused by for more types of bacteria. In an embodiment, the compounds are broad spectrum antibacterial agents (e.g., an antibiotic towards a wide range of bacteria (e.g., gram positive, gram negative, multiple families of bacteria, multiple types of bacteria, and the like)). In an embodiment, the types of bacteria can include: *Enterococcus faecium, Staphylococcus aureus, Klebsiella pneumoniae, Acinetobacter baumannii, Pseudomonas aeruginosa, Enterobacter cloacae*, or combinations thereof.

It should be noted that the therapeutically effective amount to result in uptake of the bis-cyclic guanidine compound into the subject can depend upon a variety of factors, including for example, the age, body weight, general health, sex, and diet of the subject; the time of administration; the route of administration; the rate of excretion of the specific compound employed; the duration of the treatment; the existence of other drugs used in combination or coincidental with the specific composition employed; the type(s) of bacteria; and like factors well known in the medical arts.

An embodiment of the present disclosure includes a method of inhibiting the growth of a biofilm on a surface or growth of bacteria on a surface. In an embodiment, the method includes exposing a surface to having a biofilm to a composition comprising a bis-cyclic guanidine compound, such as those described herein. The biofilm can be at any stage of development. In another embodiment, a surface can be pretreated with a bis-cyclic guanidine compound to inhibit the formation of a biofilm.

In an embodiment, the composition (e.g., bis-cyclic guanidine compound) when disposed on a surface may have an antibacterial characteristic (e.g., kills at least 70%, at least 80%, at least 90%, at least 95%, or at least 99% of the microorganisms (e.g., bacteria) on the surface and/or reduces the amount of antibacterial that form or grow on the surface by at least 70%, at least 80%, at least 90%, at least 95%, or at least 99%, as compared to a similar surface without the polymer composition disposed on the surface).

In an embodiment, the structures having the surface can include those that may be exposed to bacteria, have bacteria disposed on them, have a biofilm disposed on them, and the like. In an embodiment, the surface can be of a structure such as pipes or plumbing, tile, stone, ceramic, marble, granite, fabrics, cooking counters, food processing facilities, kitchen utensils, food packaging, swimming pools, metals, drug vials, medical instruments, medical implants, yarns, fibers, gloves, furniture, plastic devices, toys, diapers, leather, tiles, and flooring materials.

Figure 10:
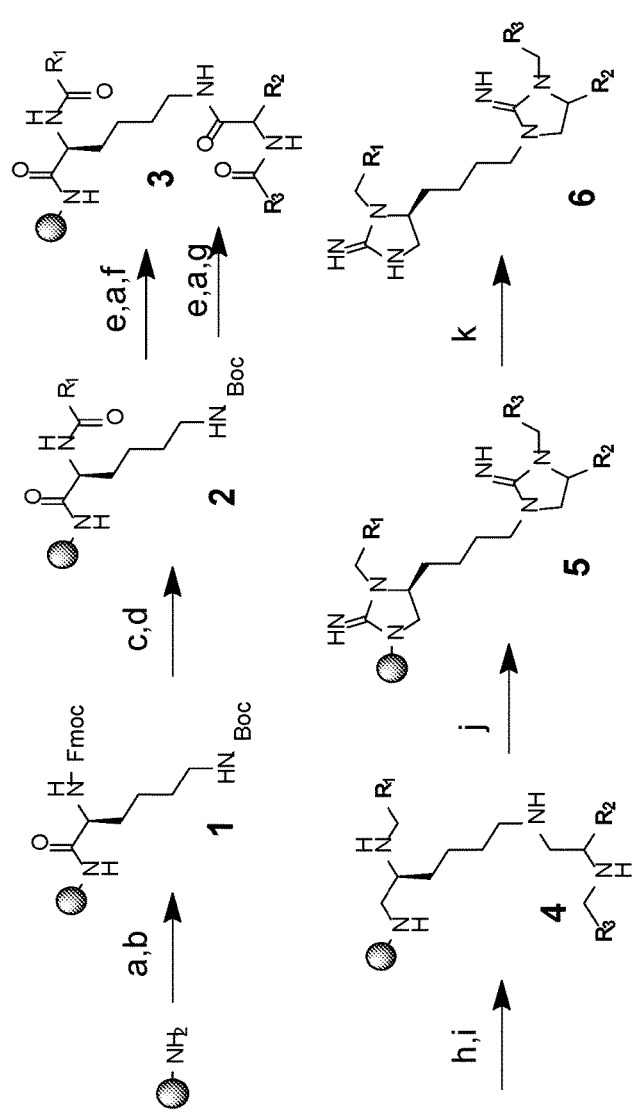
FIG. 10 illustrates scheme 1, a synthetic scheme of bis-cyclic guanidines. a) 5% DIEA/DCM; b) Fmoc-Lys (Boc)-OH, DIC, HOBt, DMF; c) 20% Piperidine/DMF; d) $R_1$COOH, DIC, HOBt, DMF; e) 55% TFA/DCM; f) Boc-AA($R_2$), DIC, HOBt, DMF; g) $R_3$COOH, DIC, HOBt, DMF; h) BH3-THF, 65° C., 96 hours; i) Piperidine, 65° C., 24 hours; j) CNBr, DCM; k) HF, anisole, 0° C.
Figure 11:
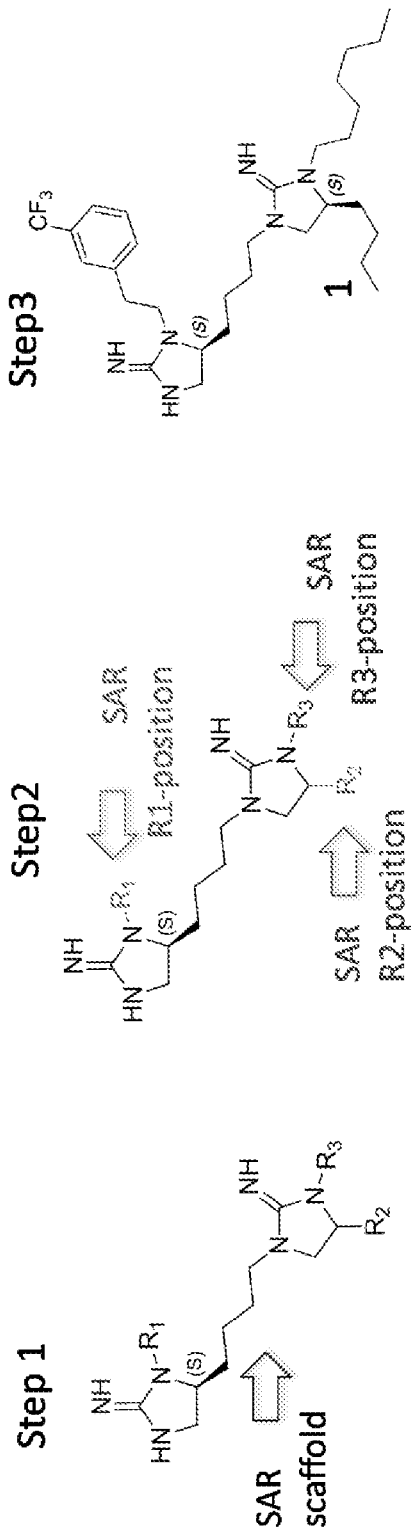
FIG. 11 illustrates embodiments of the present disclosure.

Individual compounds described herein can be synthesized using the following synthetic scheme (Scheme 1, FIG. 10). (Nefzi et al. (2001). *J Comb Chem;* 3, 68-70)., Nefzi et al. (2004) *J Org Chem;* 69, 3603-3609), (Wu et al. (2013) *J. Med. Chem;* 56, 10103-10117) Utilizing the "tea-bag" methodology (Houghten et al. (*Proc Natl Acad Sci USA* 1985, 82, 5131-5).}, 100 mg of p-methylbenzdrylamine (MBHA) resin (1.1 mmol/g, 100-200 mesh) was sealed in a mesh "tea-bag," neutralized with 5% diisopropylethylamine (DIEA) in dichloromethane (DCM), and subsequently swelled with additional DCM washes. Fmoc-Lys(Boc)-OH was coupled in Dimethylformamide (0.1M DMF) for 120 minutes in the presence of Diisopropylcarbodiimide (DIC, 6 equiv.) and 1-Hydroxybenzotriazole hydrate (HOBt, 6 equiv.) (1, Scheme 1). The Fmoc protecting group was removed with 20% piperidine in DMF for 20 minutes and the $R_1$ carboxylic acids was coupled using (10 equiv.) in the presence of DIC (10 equiv) and HOBt (10 equiv) in DMF (0.1M) for 120 minutes (2, Scheme 1). The Boc protecting group was then removed with Trifluoroacetic Acid (TFA) in DCM for 30 minutes and subsequently neutralized with 5% DIEA/DCM (3×). Boc-Amino Acids were coupled utilizing standard coupling procedures (6 equiv.) with DIC (6 equiv.) and HOBt (6 equiv.) in DMF (0.1M) for 120 minutes. The Boc group was removed with 55% TFA/DCM for 30 minutes and subsequently neutralized with 5% DIEA/DCM (3×). Carboxylic acids were coupled using (10 equiv.) in the presence of DIC (10 equiv.) and HOBt (10 equiv.) in DMF (0.1M) for 120 minutes (3, Scheme 1). All coupling reactions were monitored for completion by Ninhydrin test. The reduction was performed in a 4000 mL Wilmad LabGlass vessel under nitrogen. A Borane in 1.0M Tetrahydrofuran complex solution was used in 40 fold excess for each amide bond. The vessel is heated to 65° C. and maintained at temperature for 96 hours. The solution is then removed and the bags are washed with THF and methanol. Once completely dry, the bags are treated for 24 hours with piperidine at 65° C. and washed several times with methanol, DMF and DCM (4, Scheme 1). Before proceeding, completion of reduction is monitored by a control cleavage and analyzed by LCMS. Urea cyclization (5, Scheme 1) was performed with a 5 fold excess (for each cylization) of Cyanogen bromide (CNBr) in a 0.1M anhydrous DCM solution overnight. Following the cyclization, the bags are rinsed with DMF and DCM. The resin is cleaved with HF in the presence of anisole in an ice bath at 0° C. for 90 minutes (6, Scheme 1). The products are then extracted from the HF vessels with 95% acetic acid in water, transferred to scintillation vials, frozen and lyophilized. They are then reconstituted in 50% acetonitrile and water, frozen and lyophilized three more times. Final crude products are purified by RP-HPLC. For purposes of describing functional groups R1 and R3 consistent with the descriptions above, —CH$_2$—R1 and —CH$_2$—R3 in structure 6 from Scheme 1 can be represented by R1 and R3 in the following structure.

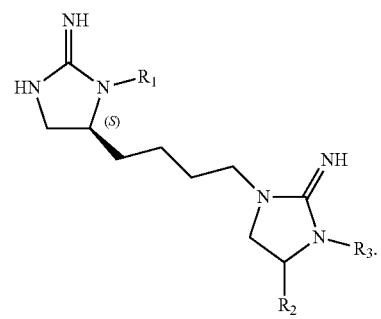

Pharmaceutical Formulations and Routes of Administration

Embodiments of the present disclosure include a bis-cyclic guanidine compound as identified herein and formulated with one or more pharmaceutically acceptable excipients, diluents, carriers and/or adjuvants. In addition, embodiments of the present disclosure include a bis-cyclic guanidine compound formulated with one or more pharmaceutically acceptable auxiliary substances. In particular bis-cyclic guanidine compound can be formulated with one or more pharmaceutically acceptable excipients, diluents, carriers, and/or adjuvants to provide an embodiment of a composition of the present disclosure.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the bis-cyclic guanidine compound can be administered to the subject using any means capable of resulting in the desired effect. Thus, the bis-cyclic guanidine compound can be incorporated into a variety of formulations for therapeutic administration. For example, the bis-cyclic guanidine compound can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the bis-cyclic guanidine compound may be administered in the form of its pharmaceutically acceptable salts, or a subject active composition may be used alone or in appropriate association, as well as in combination, with other pharmaceutically active compounds. The following methods and excipients are merely exemplary and are in no way limiting.

For oral preparations, the bis-cyclic guanidine compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the bis-cyclic guanidine compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the bis-cyclic guanidine compound can be utilized in aerosol formulation to be administered via inhalation. Embodiments of the bis-cyclic guanidine compound can be formulated into pressurized acceptable propellants such as dichlorodifluoromethane, propane, nitrogen and the like.

Furthermore, embodiments of the bis-cyclic guanidine compound can be made into suppositories by mixing with a variety of bases such as emulsifying bases or water-soluble bases. Embodiments of the bis-cyclic guanidine compound can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compositions. Similarly, unit dosage forms for injection or intravenous administration may comprise the bis-cyclic guanidine compound in a composition as a solution in sterile water, normal saline or another pharmaceutically acceptable carrier.

Embodiments of the bis-cyclic guanidine compound can be formulated in an injectable composition in accordance with the disclosure. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles in accordance with the present disclosure.

In an embodiment, the bis-cyclic guanidine compound can be formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of the bis-cyclic guanidine compound can be accomplished using any of a variety of refillable, pump systems. Pumps provide consistent, controlled release over time. In some embodiments, the bis-cyclic guanidine compound can be in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent (e.g., the bis-cyclic guanidine compound) can be delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present disclosure is the Synchromed infusion pump (Medtronic).

Suitable excipient vehicles for the bis-cyclic guanidine compound are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the bis-cyclic guanidine compound adequate to achieve the desired state in the subject being treated.

Compositions of the present disclosure can include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the pharmaceutical composition of the present disclosure (as well as combination compositions) can be delivered in a controlled release system. For example, the bis-cyclic guanidine compound may be administered using intravenous infusion, an implantable osmotic pump, a transdermal patch, liposomes, or other modes of administration. In one embodiment, a pump may be used (Sefton (1987). *CRC Crit. Ref. Biomed. Eng.* 14:201; Buchwald et al. (1980). *Surgery* 88:507; Saudek et al. (1989). *N. Engl. J. Med.* 321:574). In another embodiment, polymeric materials are used. In yet another embodiment a controlled release system is placed in proximity of the therapeutic target thus requiring only a fraction of the systemic dose. In yet another embodiment, a controlled release system is placed in proximity of the therapeutic target, thus requiring only a fraction of the systemic. Other controlled release systems are discussed in the review by Langer (1990). *Science* 249:1527-1533.

In another embodiment, the compositions of the present disclosure (as well as combination compositions separately or together) include those formed by impregnation of the bis-cyclic guanidine compound described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

Dosages

Embodiments of the bis-cyclic guanidine compound can be administered to a subject in one or more doses. Those of skill will readily appreciate that dose levels can vary as a function of the specific the bis-cyclic guanidine compound administered, the severity of the symptoms and the susceptibility of the subject to side effects. Preferred dosages for a given compound are readily determinable by those of skill in the art by a variety of means.

In an embodiment, multiple doses of the bis-cyclic guanidine compound are administered. The frequency of administration of the bis-cyclic guanidine compound can vary depending on any of a variety of factors, e.g., severity of the symptoms, and the like. For example, in an embodiment, the bis-cyclic guanidine compound can be administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in an embodiment, the bis-cyclic guanidine compound is administered continuously.

The duration of administration of the bis-cyclic guanidine compound analogue, e.g., the period of time over which the bis-cyclic guanidine compound is administered, can vary, depending on any of a variety of factors, e.g., patient response, etc. For example, the bis-cyclic guanidine compound in combination or separately, can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

Routes of Administration

Embodiments of the present disclosure provide methods and compositions for the administration of the active agent (e.g., the bis-cyclic guanidine compound) to a subject (e.g., a human) using any available method and route suitable for drug delivery, including in vivo and ex vivo methods, as well as systemic and localized routes of administration.

Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent (e.g., the bis-cyclic guanidine compound) can be administered in a single dose or in multiple doses.

Embodiments of the bis-cyclic guanidine compound can be administered to a subject using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the bis-cyclic guanidine compound. Where systemic delivery is desired, administration typically involves invasive or systemically absorbed topical or mucosal administration of pharmaceutical preparations.

In an embodiment, the bis-cyclic guanidine compound can also be delivered to the subject by enteral administration. Enteral routes of administration include, but are not limited to, oral and rectal (e.g., using a suppository) delivery.

Methods of administration of the bis-cyclic guanidine compound through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLE

Mixture based synthetic combinatorial libraries offer a tremendous enhancement for the rate of drug discovery, allowing the activity of millions of compounds to be assessed through the testing of exponentially fewer samples. In this study we used a scaffold-ranking library to screen 37 different libraries for antibacterial activity against the ESKAPE pathogens. Each library contained between 10,000 and 750,000 structural analogs for a total of >6 million compounds. From this we identified a bis-cyclic guanidine library that displayed strong antibacterial activity (FIG. 11). A positional scanning library for these compounds was developed and used to identify the most effective functional groups at each variant position. Individual compounds were synthesized that were broadly active against all ESKAPE organisms at concentrations <2 μM. In addition, these compounds were bactericidal, had anti-biofilm effects, showed limited potential for the development of resistance, and displayed almost no toxicity when tested against human lung cells and erythrocytes. Using a murine model of peritonitis, we also demonstrate that these agents are highly efficacious in vivo.

Introduction:

Nosocomial infections are a significant cause of human morbidity and mortality. In the United States alone there are 2 million such infections every year caused by bacterial pathogens, leading to approximately 100,000 deaths.[1] These infections are a significant public health concern as they are typically caused by broadly multidrug resistant organisms, which have become virtually unmanageable with existing antibacterial chemotherapeutics.[2] It is thus no surprise that the World Health Organization has identified antimicrobial resistance as one of the three greatest threats to mankind in the 21$^{st}$ century.[3] In light of this, the Infectious Disease Society of America (IDSA) coined the term ESKAPE pathogens almost a decade ago, referring to the six bacterial species that collectively cause around two-thirds of all US nosocomial infections, and have effectively escaped the ability to be treated by existing drugs.[4] These bacteria are: *Enterococcus faecium, Staphylococcus aureus, Klebsiella pneumoniae, Acinetobacter baumannii, Pseudomonas aeruginosa*, and *Enterobacter* species.

In spite of the rapid and continued emergence of drug resistant ESKAPE pathogen isolates, there has been an alarming decline in drug discovery efforts in the pharmaceutical industry; resulting in a 75% reduction in FDA approval of antibacterial agents from 1983-2007.[4] For three of the Gram-negative ESKAPE organisms (*K. pneumoniae, A. baumannii* and *P. aeruginosa*), a post antibiotic era has effectively been realized, with pan-resistant isolates identified on numerous occasions over the last decade.[5]_ENREF_6_ENREF_7 As a result, the IDSA recently issued a call to action, indicating the urgent necessity of developing sustainable antibacterial research and development that responds to current resistance trends, and anticipates the development of resistance in the future.[4]

The use of positional scanning libraries (PSL) provides a fundamental shift in the drug discovery processes for diseases. These libraries allow the evaluation of thousands to millions of synthetic compounds through the use of exponentially fewer test samples, compared to traditional approaches of screening individual agents against a given target. PSLs contain diverse chemical structures, and large numbers of compounds in each library, which increases the rate of identifying compounds with useful chemical characteristics.[6] Such approaches expedite the screening process, allowing for rapid selection of specific PSLs that can be deconvolved, generating strong and detailed SAR data due to high structural density of the libraries.[7] Furthermore, it has been demonstrated through chemoinformatic approaches that PSLs have the ability to expand currently known medicinal chemistry space.[8] Taking all these considerations together, the use of such libraries can rapidly enhance the drug discovery process, which is of significant benefit in trying to keep pace with increasing rates of antibacterial resistance.

In this study, we began with a scaffold ranking library containing 37 different combinatorial libraries composed of 10,000 to 750,000 compounds each, leading to a total of >6 million compounds tested. From this initial screening, a PSL based around a core bis-cyclic guanidine scaffold was selected for further evaluation. The library contained 45,864 different bis-cyclic guanidines systematically formatted into 110 mixture samples. By screening this library, we identified a series of individual bis-cyclic guanidine compounds that have strong antibacterial activity against both Gram-positive and Gram-negative organisms.

Guanidine based compounds have been found to possess extensive functional bioactivities.[9] In the late 1960s, guanidine hydrochloride was used to treat *Clostridium botulinum* infections as it was found to block presynaptic potassium channels, which stimulated neurotransmitter release, and alleviated toxin mediated paralysis.[10] Guanidine related compounds like bisbiguanides (such as chlorhexidine) and bisamidines (such as hexamidine) have shown broad spectrum activity against both Gram-negative and Gram-positive pathogens and are commonly used as antiseptics. Recently, the attachment of guanidinium groups to both neomycin B and kanamycin A has been shown to restore and extend their activity towards gentamicin-resistant *Pseudomonas aeruginosa* and methicillin-resistant *Staphylococcus aureus.*[11] Finally, a highly novel antimicrobial agent (teixobactin) containing a cyclic guanidine substituent was recently discovered, demonstrating excellent activity against Gram-positive organisms, and displaying essentially no propensity for the development of resistance.[12] More relevant to this study, in work by Rideout et al.,[13] pyrrolidine bis-cyclic guanidines were identified, with antibacterial activity towards Gram-positive and Gram-negative species. These agents were found to interfere with DNA replication, and induce envelope stress in target organisms. Interestingly, the bis-cyclic guanidine library tested herein was also screened in these holiday junction accumulation assays, and found to bind these structures as well, although at a much lower frequency than the their pyrrolidine-based counterparts.

Further to this, the pyrrolidine bis-cyclic guanidines were actually part of the combinatorial library screened in the present study (library 1955); however the simpler bis-cyclic guanidine scaffold identified herein possessed a broader spectrum of activity at more promising concentrations.

As such, in this study we have identified a novel series of bis-cyclic guanidine compounds that have broad activity against all of the ESKAPE pathogens, limited toxicity to human cells, a strong ability to eradicate bacterial biofilms, and show promising efficacy in mammalian models of infection. We contend that employing positional scanning approaches, and the accompanying strategies described herein, create a fundamental shift away from traditional antibacterial testing methodologies, by introducing a rapid approach to discover novel compounds that possess broad spectrum activity.

Results and Discussion:
Scaffold Ranking Library.

In order to rapidly assess the available chemical scaffolds in our combinatorial collection for their potential broad-spectrum antibacterial activity, a scaffold ranking library approach was utilized. We have previously described in detail the construction,[14][6] advantages and limitations of the scaffold ranking library,[6] as well as its successful implementation for the discovery of several classes of novel ligands for a range of targets and indications;[15][16][17] including antimicrobials that inhibit tyrosine recombinases and Holliday junction-resolving enzymes.[13a][18] In the current project we utilized a scaffold ranking library containing 37 mixture samples, each of which was comprised of approximately equal molar concentrations of individual compounds containing the same common core scaffold (Supplemental Table S1). The 37 mixtures were screened for antimicrobial activity against all six ESKAPE pathogens using a microbroth dilution assay. From the initial scaffold ranking data (FIG. 1) we determined that the most potent broad spectrum library was 2157. This sample (FIG. 1) effectively inhibited E. faecium, S. aureus, A. baumannii, P. aeruginosa, and E. cloacae at 100 µM. More importantly the sample retained broad spectrum activity at 5 µM, where it inhibited E. faecium, S. aureus, A. baumannii, and E. cloacae. Two other samples, 2161 and 1952 (both polyamines) were active against all six ESKAPE pathogens at 100 µM, but did not retain broad spectrum activity at lower concentrations, which led to a less significant stacked scale score. In general scaffolds containing cyclic guanidines, piperazines, and polyamines were amongst the most active scaffolds (see Supplementary Table 1 for list of core scaffolds). However the broad antimicrobial activity, even at low concentrations, led us to further investigate the 2157 positional scanning library.

Deconvolution of the 2157 Library.

Figure 2B:
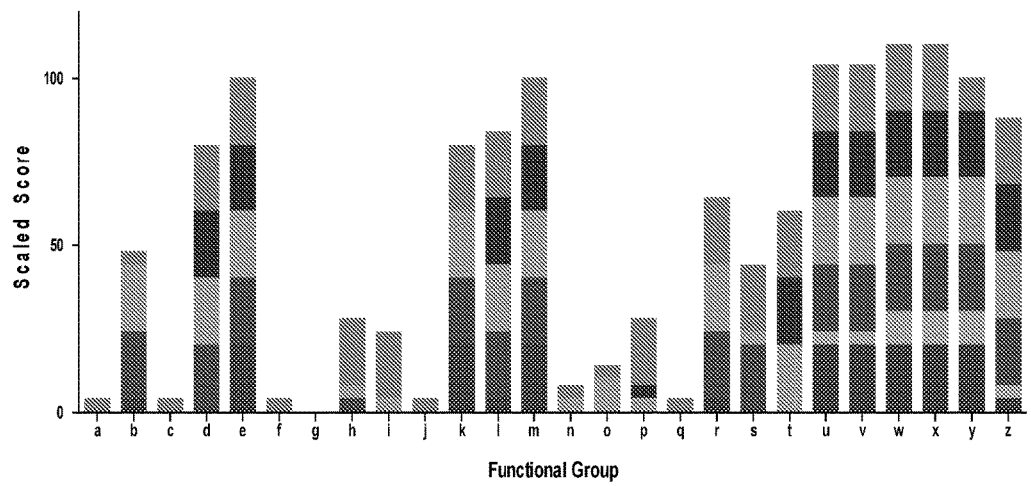
Figure 2C:
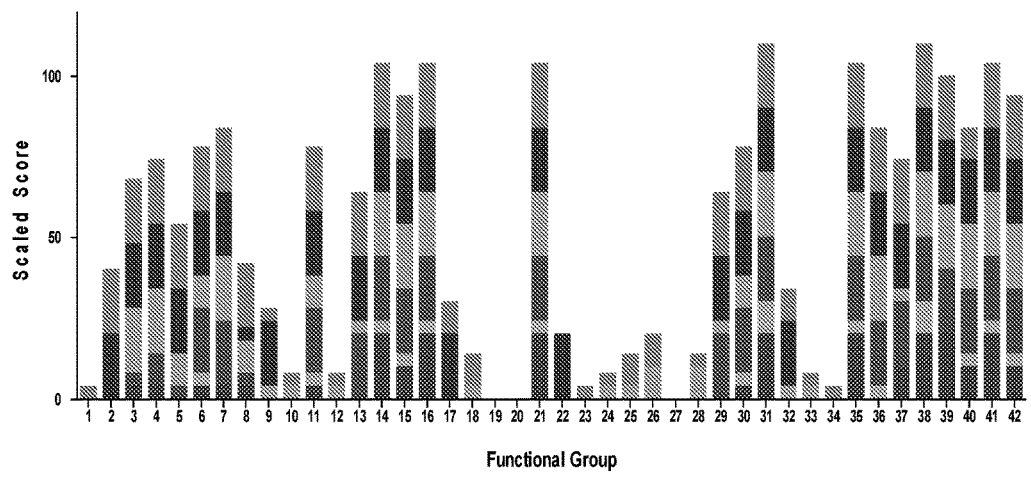

Library 2157 is a positional scanning library containing 45,864 individual bis-cyclic guanidines (Scheme 1 (FIG. 10) and FIG. 2) systematically synthesized into 110 mixture samples (Supplemental Table S2). These separate 110 mixtures were next screened against the ESKAPE pathogens to deconvolve specific antibacterial activity, and begin to generate a structure activity relationship. The first 42 of these 110 samples contain the 45,864 bis-cyclic guanidines arranged by fixing the $R_1$ position (FIG. 2A, Supplemental Table 2); the next 26 samples are arranged by $R_2$ position (FIG. 2B); and the last 42 samples are arranged by $R_3$ (FIG. 2C). By way of example the first sample in FIG. 2A contains an equal molar amount of the 1,092 individual compounds in the library that have hydrogen fixed at the $R_1$ position; likewise the last sample in FIG. 2C contains an equal molar amount of the 1,092 individual compounds in the library that have 2-bicyclo[2.2.1]hept-2-yl-ethyl fixed at the $R_3$ position.

The 110 samples from Library 2157 were screened for antimicrobial activity against all six ESKAPE pathogens in a similar manner to the Scaffold Ranking Library, generating MIC data for each sample (FIG. 2, Supplemental Table 3). From this we determined a clear differentiation in the potency of mixtures. For example, those fixed with large aromatic or aliphatic substitutions, such as 2-(3-trifluoromethyl-phenyl)-ethyl and adamantan-1-yl-ethyl, respectively, at $R_1$, were more potent than any of the mixtures fixed with small aliphatic groups, such as butyl and isobutyl. However, we noted that samples fixed at the $R_2$ position with different butyl functionalities are actually amongst the most potent, although as the butyl group is shortened to a propyl and then a methyl, there appears to be step-wise reduction in potency. Additionally there is no apparent preference for absolute configuration at this position. For the R3 position a number of samples with aliphatic (cyclic and acyclic) and aromatic functionalities fixed at the R3 position show activity, however there were a few trends that seem to affect activity at this position such as the size of the aliphatic group (larger favored) as well as the preference for aromatic electron withdrawing groups over electron donating groups. For example changing from a heptyl, six carbon chain functionality, to a butyl, four carbon chain in R3 effectively eliminates activity of the sample; and switching from a weak meta-electron donating group such as 2-(3-fluoro-phenyl)-ethyl or 2-(3-bromo-phenyl)-ethyl to a strong meta-donating group such as 2-(3-methoxy-phenyl)-ethyl at the R3 position reduced the overall activity of the sample.

From this data we could have chosen a number of different functionalities (active samples) to fix at each of the positions; however in order to reduce the number of compounds produced, we selected 27 individual compounds for synthesis. These compounds were selected by combining the functionalities of the most potent mixtures from each of the R positions, while biasing to include as much structural diversity as possible (Supplemental Table S4 Samples 1-27).

Screening of Individual Compounds.

Figure 3:
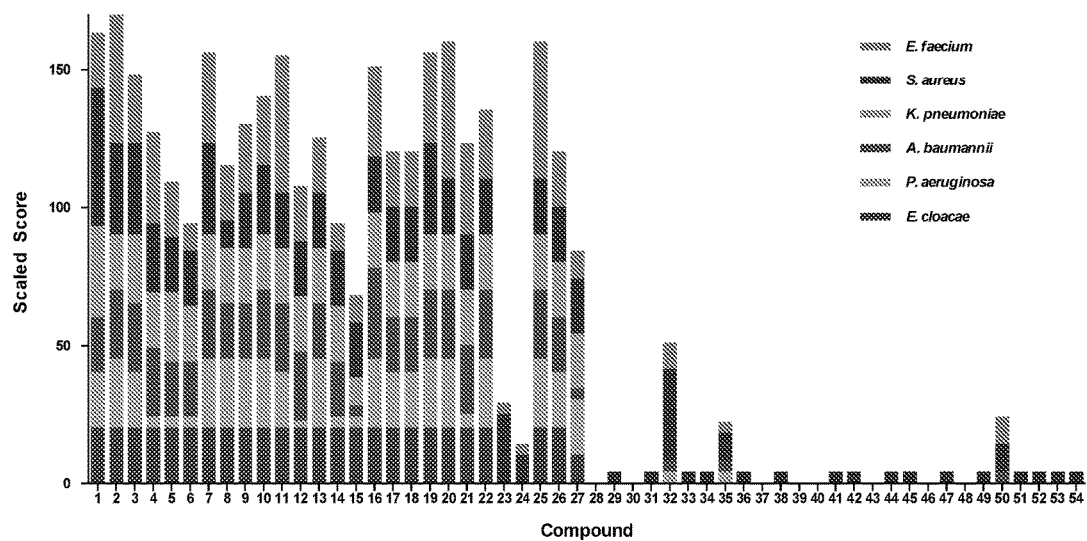
FIG. 3 is a graph illustrating the assessment of the antibacterial activity of individual bis-cyclic guanidines synthesized based on library SAR data. Fifty-four individual compounds were synthesized for testing against the ESKAPE pathogens. 1-27 were generated based on SAR data from ESKAPE testing with the combinatorial libraries; 28-54 were included as they were predicted to be significantly less active based on PSL data. Data is presented as stacked, scaled scores, with the height for each color of individual bars determined by dividing 100 μM (the maximum concentration tested) by the individual MIC for each agent. Compounds are then given a scaled score for each pathogen, and these are then stacked to determine which have the broadest activity, at the lowest concentration. Note data is generated using "crude" compounds (see Materials and Methods Section for details).
Figure 4:
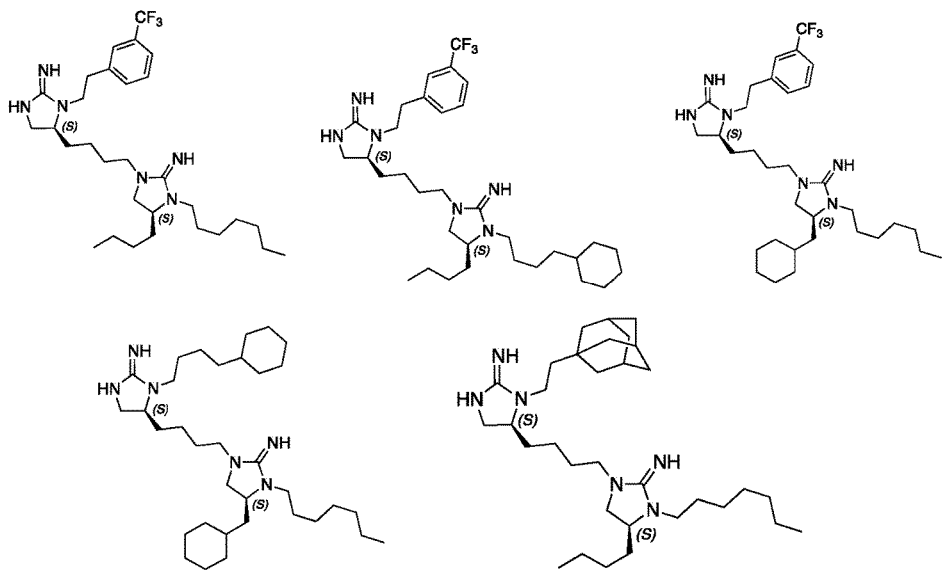
FIG. 4 illustrates bis-cyclic guanidine compounds of the present disclosure.

The 27 individual compounds were synthesized (Scheme 1, FIG. 3) and screened for antimicrobial activity against all six ESKAPE pathogens, again using MIC assays, and are reported using stacked scaled scores (FIG. 3, 1-27). Additionally, a separate set of 27 structural analogs predicted not to be potent based on the SAR were tested to verify as much, and that the SAR generated holds value for predicting potent inhibitors (Supplemental Table S4a and FIG. 3, 28-54). Although these additional 27 compounds (28-54) are very close structural analogs to the 27 compounds selected for synthesis in the ESKAPE project (1-27); based on the screening of library 2157 the additional compounds were predicted to be significantly less active towards the ESKAPE pathogens. We included these compounds to validate that the activity observed is being driven by the correct combination of functionalities around the core bis-cyclic guanidine scaffold, and not just generally by any compound from this library. The 27 novel compounds synthesized for the ESKAPE project displayed an increase in broad spectrum antibacterial activity at low concentrations. At a concentration of 45 µM, 25 of the 27 compounds inhibited growth of all six ESKAPE organisms, with 14 of these retaining activity against all organisms when the concentration decreased to 10 µM. Even more promising, 5 of the individual compounds tested (1, 2, 7, 16 and 19; FIG. 4) had antibacterial activity against all 6 species at concentrations <2 µM (Table 1). Conversely, and as expected, the 27 additional compounds (28-54) displayed almost no activity towards the ESKAPE pathogens (FIG. 3, 28-54), further validating our structure-guided design of individual compounds.

SAR and Potential Activity Cliffs for the Individual Compounds.

As previously described, the 27 compounds (1-27) were selected based on SAR information inherently contained in positional scanning library 2157. While compounds 28-54 are very close structural analogs to compounds 1-27, they clearly posses little-to-no activity when compared to compounds 1-27. A careful exploration of compound structures, in order to identify parameters that distinguished these two sets of analogs, is therefore warranted. As a first step, for each of the 54 compounds Canvas[19] was used to generate six physicochemical properties commonly used to characterize and compare compound data sets in drug discovery[20][19]: molecular weight (MW), polar surface area (PSA), A log P (log P as calculated by Canvas), number of rotatable bonds (RB), number of hydrogen bond acceptors and donors (HBA and HBD respectively). A list of all computed values for each compound can be found in Supplemental Table S4; the average and standard deviation for each of the six properties for the two sets, as well as the subset of 5 leads (1, 2, 7, 16, 19), is shown in Table 2. From these data it is evident that the average MW, A log P, and RB for the two sets is markedly different, with the active group (1-27) having a higher average MW, A log P and number of RB than the inactive set. Of note, the five lead compounds (1, 2, 7, 16, and 19) had, on average, slightly lower MW and A log P values, and slightly more rotatable bonds than the active set as a whole. Equally evident, however, is that size, lipophilicity, and flexibility do not fully capture the SAR of these data sets; even though the groupings are grossly categorized by these properties (Table 2), there are numerous examples of compounds with similar physicochemical properties having large activity differences, e.g. activity cliffs with respect to property similarity.[21] In order to investigate the potential presence of activity cliffs in a systematic manner, we used Structure-Activity Similarity (SAS) Maps,[22][7][20] which were one of the first methods developed to characterize SARs by using the concept of activity landscape modeling. SAS maps systematically compare a given representation of molecular similarity with activity similarities for all possible combinations of compounds in a data set.[23] Because the SAR observed with any dataset is highly dependent on the molecular representation used,[24] different structural similarity methods can have drastically different behavior with regards to activity cliffs. Using SAS maps, each of the 1,431 non-redundant pairs of the 54 compounds in the series was evaluated for potency, similarity and relative molecular similarity (FIG. 5).

Figure 5:
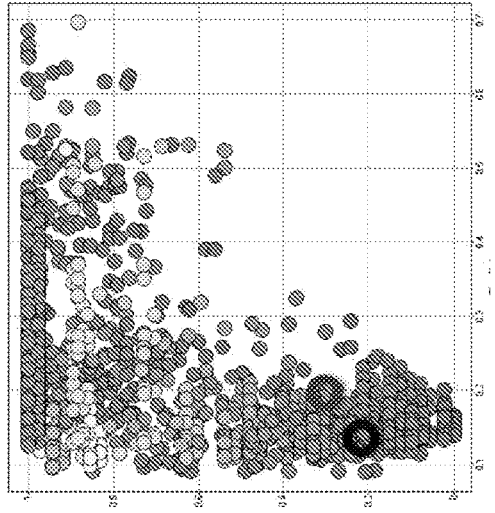
FIG. 5 illustrates graphs of the computational exploration of physicochemical properties of various compounds. Each of the 54 compounds (1-54) is compared against each of the remaining 53 compounds for differences in potency (Y-axis both left and right panel) and molecular representation (Physicochemical Properties: X-axis left panel; Radial: X-axis right panel). Each pair is represented by a dot. In this way a pair of compounds with similar activity potencies and physicochemical properties will be shown by a dot in the upper right hand quadrant of the left panel. The dots are colored by activity of the most potent compound in a pair, using a continuous color of: Grey (no activity (top and dark color), Yellow (low activity, lightest color), Orange (moderate activity, middle color range), and Red (high activity, second darkest color). Shown below the panels are structures for two such pairs. The pair in the left location on both panels (19-35) is identified by open blue circles, whilst the pair in the right location (2-32) is indicated by open black circles. Under each structure is the total activity value used for each compound, as well as the three physicochemical values (MW, A log P, and RB) associated with a given agent.
Figure 5:
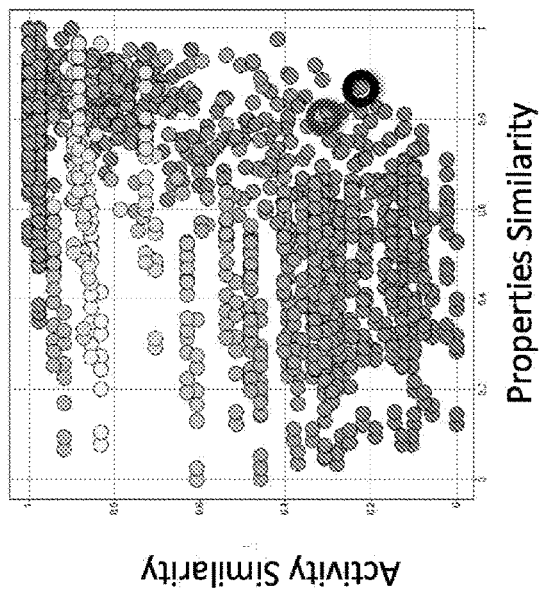
Figure 5:
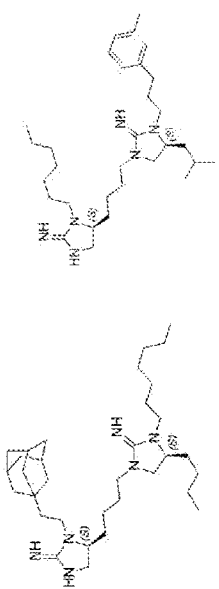

The left panel of FIG. 5 shows a SAS map with molecular similarity computed using the six physicochemical properties (following a method we have previously described,[24] and summarized in the Materials and Methods) on the x-axis and potency similarity on the y-axis. The data points in the lower right hand quadrant of this plot indicate pairs of compounds with high similarity in the six physicochemical properties used, but low activity similarity (i.e. large differences in potency). Such points thus represent activity cliffs. As such, it is clear from the large number of similar points in the plot that property differences alone are not sufficient to explain the activity differences in these 54 compounds. Two example pairs are highlighted in FIG. 5: pair 19 (an active compound) and 35 (a relatively inactive compound) are shown by open blue circles, whilst pair 2 (an active compound) and 32 (a relatively inactive compound) are shown by open black circles. The right panel shows a SAS map where the molecular similarity was computed using a different molecular representation: radial fingerprints. Radial fingerprints entail growing a set of fragments radially from each heavy atom over a series of iterations,[25] and are equivalent to extended connectivity fingerprints (ECFPs).[26] In sharp contrast to the SAS map obtained with physicochemical properties, the SAS map generated with radial fingerprints does not show activity cliffs. For example, the two pairs of compounds 19-35 and 2-32 are now appropriately located in the lower left quadrant of the SAS map (right panel FIG. 5). Notably, we recently reported the superior performance of radial fingerprints over other fingerprint-based methods for activity landscape studies.[27]

The disparity between the SAS maps is a strong argument for the exploration of dense portions of the chemical space; here, representative compounds based on physicochemical properties would have been ill-equipped to properly characterize the active compounds found. Indeed, because of the high structural density of positional scanning libraries,[20] they are inherently very rich in SAR information, and well suited to assess the presence of activity cliffs.[10][21][28] Taken together, analysis of the SAR indicates that, although in general the active compounds (1-27) are more hydrophobic and have more rotatable bonds than the inactive compounds (28-54), the specific atom connectivity, as captured by radial fingerprints, plays a key role in the activity of the molecules.

Exploring the Antibacterial Activity of Frontrunner Agents Using a Library of ESKAPE Pathogen Isolates.

Thus far, all data was derived using individual, albeit highly drug resistant, isolates. To assess the full antibacterial potency of front runner agents, additional data was collected using a panel of clinical ESKAPE isolates (Supplemental Table 5-6). We determined that all Gram positive strains (E. faecium and S. aureus), as well as those isolates of the Gram negative organism A. baumannii, were sensitive to frontrunner agents at 2 µM, with absolutely no variation. Furthermore, the growth of 95% of all isolates (regardless of species) was inhibited by the five lead bis-cyclic guanidines at concentrations of ≤10 µM. K. pneumoniae and E. cloacae strains displayed slight variation in MIC values, with agents 2 and 19 inhibiting the growth of 90% of isolates for both species at 5 µM, and 70% of strains at 2 µM. Lead agent 16 had an MIC of 2 µM against 90% of E. cloacae strains, and 5 µM against 90% of K. pneumoniae strains. Lead agent 7, was found to be similar to 16 in activity towards K. pneumonia, inhibiting 90% of strains at 5 µM, and 90% of E. cloacae strains at 2 µM. Compound 1 had the most variation in MIC against K. pneumoniae and E. cloacae, with growth of 90% of clinical isolates for each pathogen inhibited at 10 µM. Against the P. aeruginosa panel of strains, the lead bis-cyclic guanidines had slightly higher MIC values. Lead agents 2 and 16 inhibited 90% of isolates at 5 µM, whilst agents 1, 7, and 19 inhibited 90% at 10 µM.

Given the minor variations observed in MIC for three of the Gram-negative organisms, and that these particular bacteria are renowned for efflux detoxification of antibacterial agents, we hypothesized that the differences observed likely relate to variation in efflux pump activity between strains. To test this contention, we reanalyzed MICs for all five front runner agents against our full panel of K. pneumoniae, P. aeruginosa or E. cloacae isolates in the presence of sub-inhibitory concentrations of the known efflux inhibitor, reserpine.[29] We determined that, whilst 100 µM of reserpine or 2 µM of compound 1 individually had no effect on the growth of P. aeruginosa isolate 1420, the two combined strongly inhibited growth of this strain (Supplemental FIG. 1A). Similarly, when using *P. aeruginosa* strain 1414 and frontrunner 19, we observed complete inhibition of growth when this agent was paired with reserpine (Supplemental FIG. 1B). The effects observed appear to be universal, regardless of strain or compound tested. For example, *K. pneumoniae* strain 1441, when used with compound 16 (Supplemental FIG. 1C), or *E. cloacae* strain 1446 when tested with compound 7 (Supplemental FIG. 1D), resulted in complete inhibition of growth in combination with 100 µM of reserpine. It should be noted that the data presented herein represents a worst-case scenario. For example, compound 1 was the least active of any agent against *P. aeruginosa* strain 1420; the same is true for all other pairings presented. Similar data was returned for all front runner agents, against all 10 isolates of the three Gram-negative organisms (data not shown). These findings support the hypothesis that inherent efflux mechanisms of certain Gram-negative organisms result in MIC variations for the lead bis-cyclic guanidines between clinical isolates. As such, we suggest that any minor decrease in activity for these agents can be restored by the use of a known efflux pump inhibitor.

Assessing Antibacterial Mode of Action.

We next set out to perform a thorough in vitro and in vivo characterization of these five lead agents, to assess their antimicrobial activities. To do this, we first used a minimal bactericidal concentration (MBC) assay to distinguish whether these compounds were bactericidal or bacteriostatic in nature. Upon analysis, all compounds were found to be bactericidal at concentrations close to their MICs (Table 1). Compounds 1 and 2 proved to be the most bactericidal, with the former agent having $MBC_{90}$ values ranging from 1.87 µM (against *E. faecium*) to 4.01 µM (against *P. aeruginosa*); whilst the latter had $MBC_{90}$ values ranging from 1.66 µM (against *E. faecium*) to 4.15 µM (against *E. cloacae*). Similarly, compound 19 was also strongly bactericidal, with $MBC_{90}$ values ranging from 2.61 µM (against *K. pneumoniae*) to 4.66 µM (against *A. baumannii*). For the most part, compound 16 was significantly bactericidal in effects, with $MBC_{90}$ values ranging from 2.77 µM (against *A. baumannii*) to 4.45 µM (against *K. pneumoniae*); however its $MBC_{90}$ against *E. cloacae* was slightly higher at 9.55 µM. Finally, 7 was strongly bactericidal against the first four ESKAPE pathogens, with $MBC_{90}$ values ranging from 2.16 µM to 3.28 µM; however this number rose to 6.36 µM against *E. cloacae*, and 13.74 µM against *P. aeruginosa*. As such, all compounds displayed effective bactericidal activity, with many proving so even at very low concentrations.

Figures 6A, 6B:
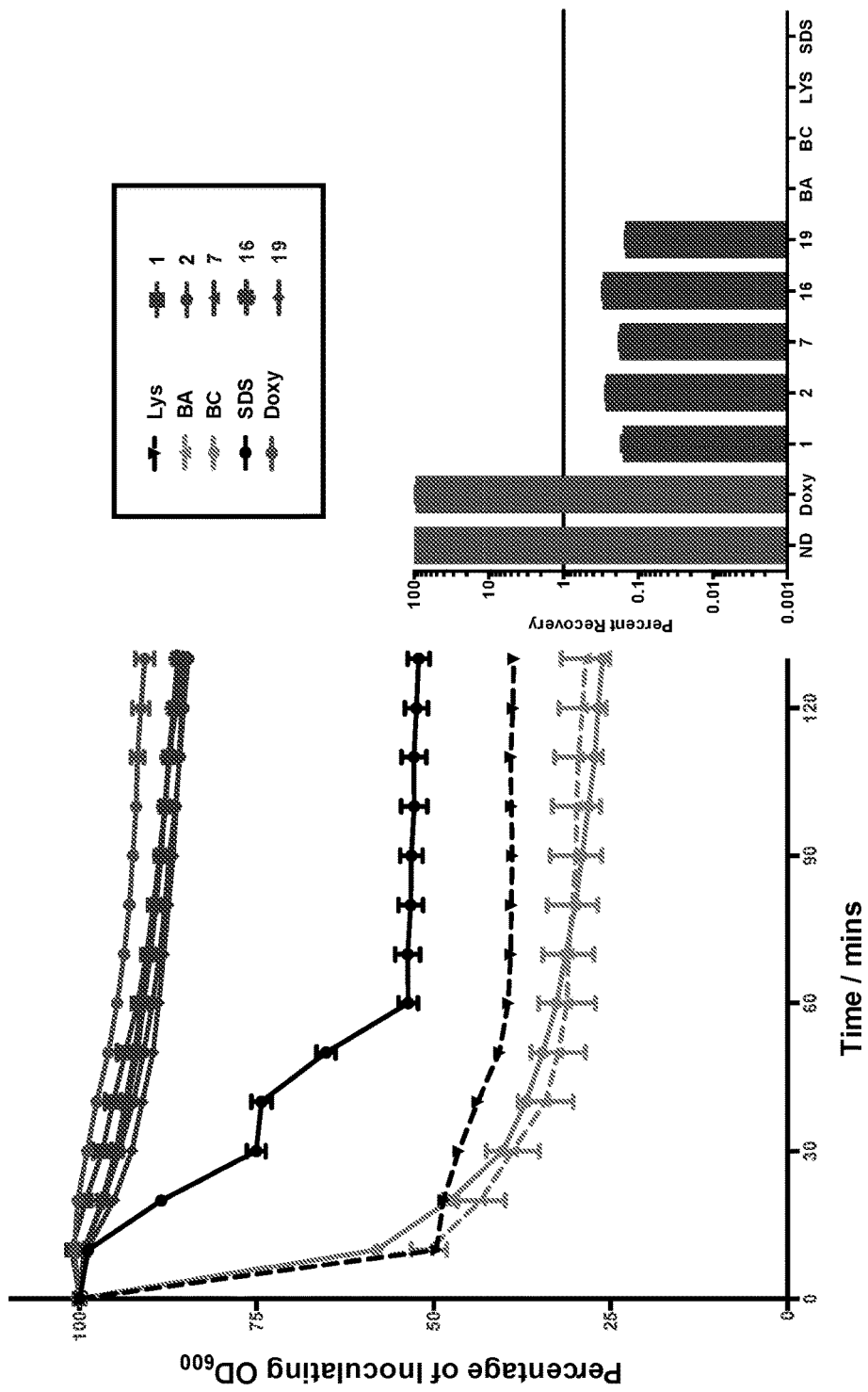
FIGS. 6A and 6B illustrates that bis-cyclic guanidines are bactericidal but not bacteriolytic.

Considering the strong bactericidal nature of the bis-cyclic guanidines, we next assessed the ability of front runner agents to lyse bacterial cells. As such, a time kill assay was performed using all five lead agents against exponentially growing MRSA cells (FIG. 6a). Alongside we also used positive controls agents, including sodium dodecyl sulfate (SDS), Lysostaphin (Lys) (a *S. aureus* specific lytic agent), benzalkonium chloride (BA) and benzethonium chloride (BC). These latter two agents are cationic detergents, and were included because the bis-cyclic guanidines have the potential to be cationic in nature at physiological pH. For our lead agents at MIC we observed limited change in bacterial density over the 2 h period. Such findings were similar to our negative control, doxycycline (a translation inhibitor). By way of comparison, we recovered only 52.2% of cells upon exposure SDS. More profoundly, we achieved >50% lysis of MRSA cells within only 10 minutes of exposure to the positive control agent lysostaphin, with viability continuing to decrease over time. Finally, both cationic detergents proved highly lytic towards MRSA, with only 28.56% and 32.63% of cells surviving exposure to benzalkonium chloride or benzethonium chloride, respectively. At 120 minutes, cultures from these tests were serial diluted and cell viability assessed by CFU $mL^{-1}$. The bacteriostatic control antibiotic doxycycline displayed a 92% recovery of cells once the antibiotic was washed out. Incubation with the lytic control agents (BA, BC, SDS, Lys) resulted in 0% cell recovery after the 120 minute assay. With regards to the bis-cyclic guanidines, we observed a 2.5-log reduction in viability after the 2 h period (0.2% recovery). As such, it would appear that although our front runner compounds result in significant bacterial death during initial incubation, this is not the result of bacterial lysis. Accordingly, these data effectively demonstrate that although the bis-cyclic guanidines are strongly bactericidal, their mode of action does not appear to be via bacterial cell lysis; unlike that of simple cationic detergents.

Determining the Antibiofilm Capacity of Lead Agents.

Biofilm formation is a common feature for all of the ESKAPE pathogens, and has profound influence of disease severity and mortality.[30] Biofilms form on implanted devices, as well as on bone, and in the heart, and are innately resistant to antimicrobial intervention.[31] As such, we next set out to assess whether our front runner compounds displayed antibacterial activity. These were performed using minimum biofilm eradication assays (MBEC), as described previously.[32] Whilst the $MBEC_{50}$ values for the lead compounds were found to be in excess of MIC and $MBC_{90}$ data, we did observe some highly promising anti-biofilm effects with each agent (Table 1). Compound 19 proved to be our most effective in this regard, having $MBEC_{50}$ values ≤8.6 µM against *S. aureus, K. pneumoniae* and *P. aeruginosa*, and between 13.37 µM and 24.07 µM for the remaining organisms. For 16, we determined $MBEC_{50}$ values of 6.28 µM, and 7.58 µM for *K. pneumoniae* and *S. aureus*, respectively; and 12.68 µM to 34.44 µM against the other four species. The remaining three agents (1, 2 and 7) had $MBEC_{50}$ values that were typically higher than this; however, 2 and 7 were strongly active against *K. pneumoniae* (4.65 and 4.81 µM), and *S. aureus* (2.18 and 4.35 µM) biofilms. As such, it appears that bis-cyclic guanidines not only have strong potential as broad spectrum antibacterial agents, but also have the capacity to limit biofilms formed by each of the ESKAPE pathogens.

Exploring the Potential for Front-Runner Toxicity Towards Human Cells.

Figure 7:
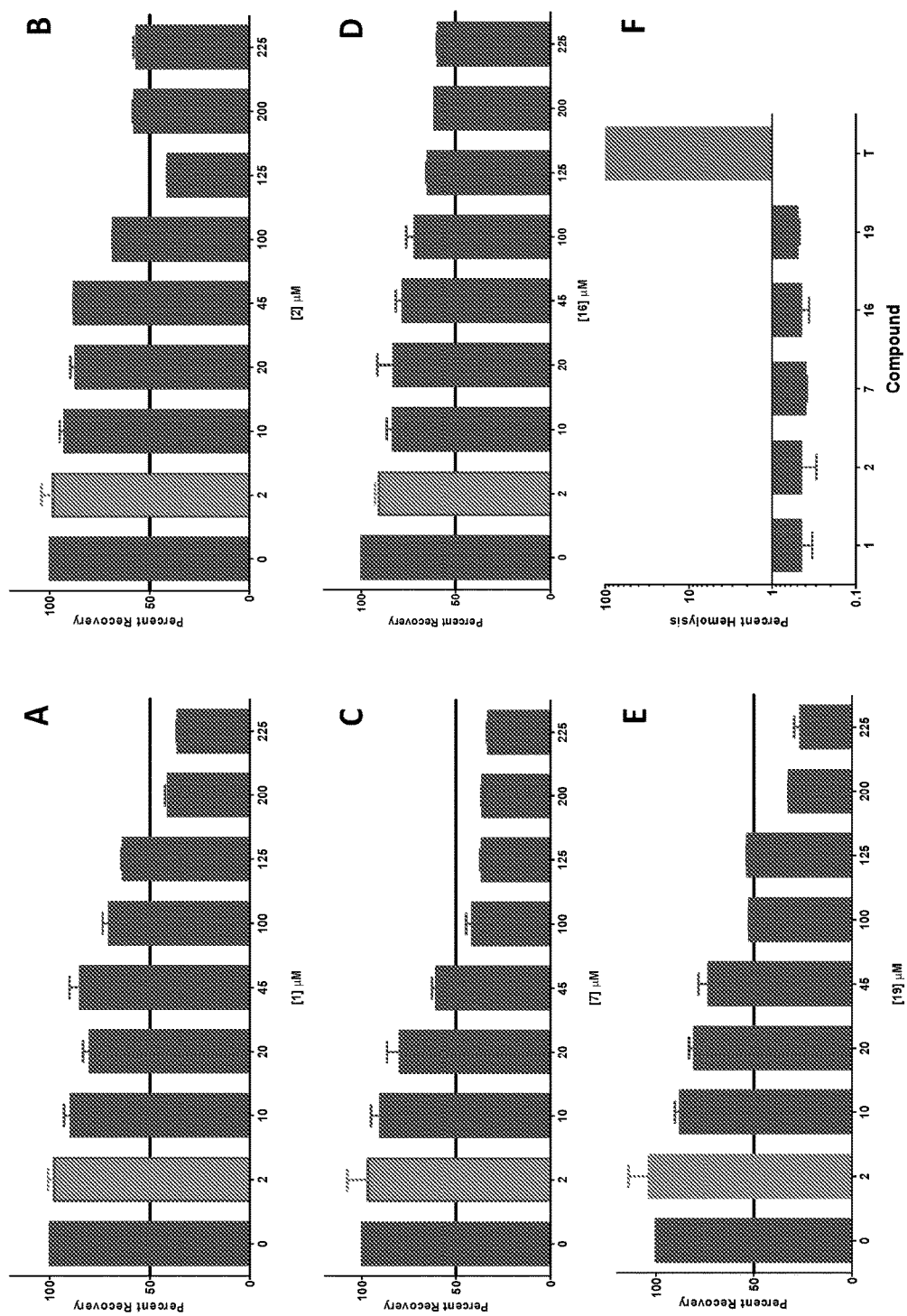
FIGS. 7A-7F illustrates cytotoxicity of lead agents. Shown is the survival of A549 cells measured using an MTT assay with all five lead agents (FIGS. 7A-7E). Data is presented as percent recovery compared to vehicle only controls. Error bars are shown ±SEM, from at least three independent experiments; MICs are denoted by grey coloring. A solid black line is shown for $IC_{50}$ value determination. Hemolytic capacity towards human erythrocytes was also measured using the lead agents (FIG. 7F). Data is shown as percent hemolysis compared to positive (1% Triton-X100 (T), 100% hemolysis) controls. Lead agents were added at a concentration of 10 μM. Error bars are shown ±SEM, from at least three independent experiments. A solid black line is shown at 1% hemolysis.

Ensuring selectivity for prokaryotic over eukaryotic cells is of primary importance during the development of antimicrobial agents. As such, we next performed cytotoxicity testing for the five lead bis-cyclic guanidines using human A549 adenocarcinomic alveolar basal epithelial cells. The screening of these five lead agents revealed remarkably low toxicity (FIG. 7 and Table 1). Specifically, lead compound 19 (FIG. 7e) displayed the least toxicity, allowing for >97% cell recovery compared to vehicle only controls at concentrations up to 45 µM. Even at the highest concentration tested (225 µM), >70% of cells were recovered. Similarly, compounds 2 (FIG. 7b) and 16 (FIG. 7d) allowed for >65% recovery at concentrations up to 100 µM, and >50% at 225 µM. Compound 1 (FIG. 7a) allowed for >65% recovery at concentrations up to 200 µM, with a slight decline to around 40% at 225 µM. Compound 7 (FIG. 7c) and 19 (FIG. 7e) yielded less favorable results, but still displayed limited toxicity, with >60% recovery at 45 µM; a concentration that is 25× their MIC. After this concentration, A549 recovery was consistently ≥33% and 26% respectively at concentrations up to 225 µM. The cytotoxicity data was used to determine $IC_{50}$ values where possible, as well as Activity Indices (AI=$IC_{50}$/MIC), to gain a sense of therapeutic window and selectivity (Table 1). Importantly, compound 16 never resulted in 50% human cell toxicity, meaning that it has an AI value far in excess of 139. For compounds 1, 19, and 2, we obtained $IC_{50}$s of 163.6 µM, 145.70 µM, and 124.6 µM, which resulted in selectivity windows of AI=100, AI=87.6, and AI=81.8, respectively. Finally, even compound 7, which had slightly more toxic effects, had an $IC_{50}$ of 65.7 µM and an AI=43.1. As such, each of our front-runner compounds appears to have excellent specificity for bacterial cells over their eukaryotic counterparts.

To ensure that these findings were not specific to the cell line used, we next assessed the tendency of lead bis-cyclic guanidines to lyse human red blood cells (hRBCs). In agreement with data from A549 cells, hemolysis assays reveal that bis-cyclic guanidine have little to no apparent toxicity towards human cells; demonstrating no effective capacity to lyse hRBCs (FIG. 70. Using all lead agents at 10 µM (>5×MIC for each molecule) we observed hemolysis levels ranging from 0.34% to 0.5%, which clearly demonstrates that lead agents have limited ability to lyse red blood cells. This is placed in context when one compares these values to that of the positive control (Triton-X100, 100% hemolysis). The inability to lyse hRBCs in addition to the lack of toxicity towards A549 cells reveal a high selectivity of bis-cyclic guanidines towards bacterial cells over human counterparts, and therefore suggests that bis-cyclic guanidines have very strong potential for development as new antibacterial agents.

Exploring the Potential for ESKAPE Pathogen Resistance to Front Runner Bis-Cyclic Guanidines.

Figure 8A:
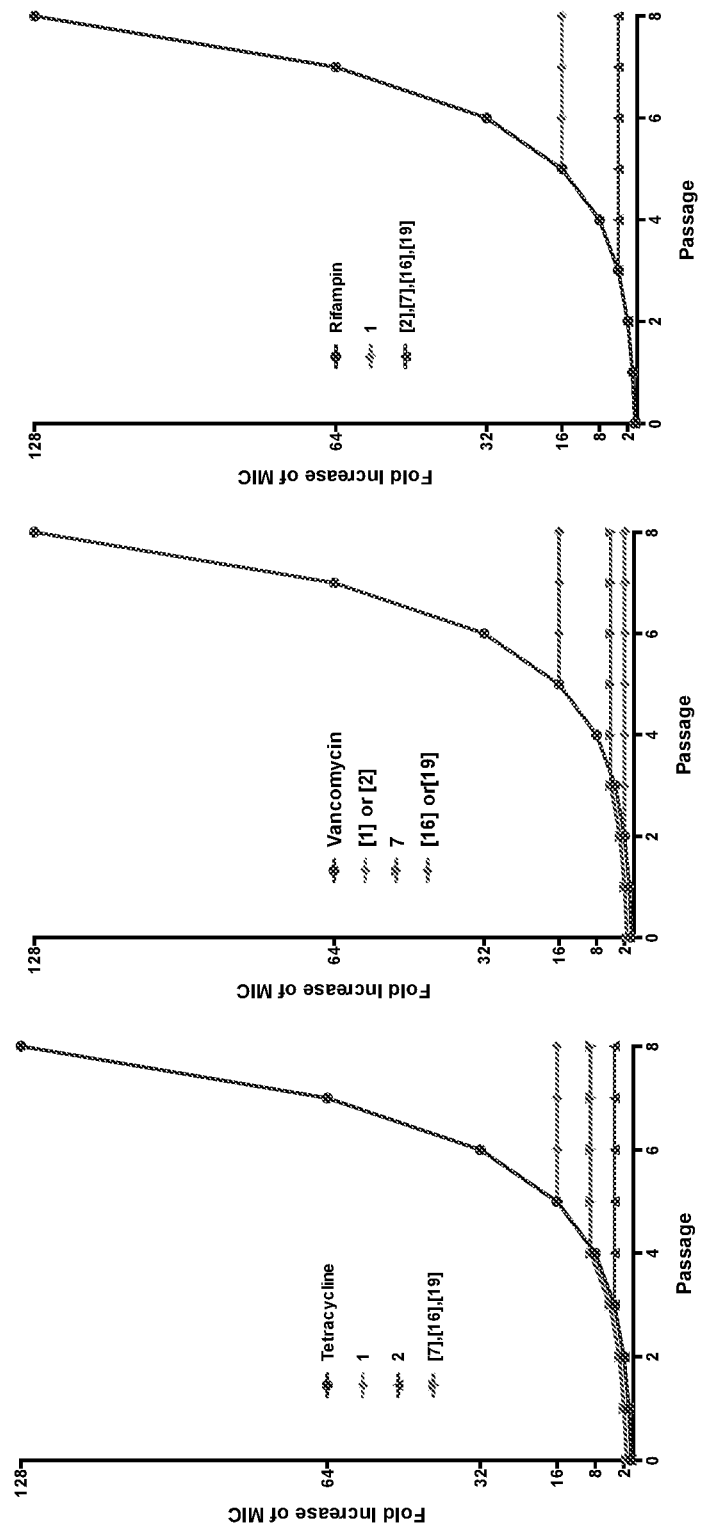
FIGS. 8A-8B illustrate graphs for adaptive tolerance by ESKAPE pathogens to various agents. ESKAPE pathogens were serially passaged for eight days in fresh liquid media (changed every 24 h), with the concentration of compound increased 2-fold each day. Shown are the increases in MIC observed over time. Ef=*E. faecium*; Ec=*E. cloacae*.
Figure 8B:
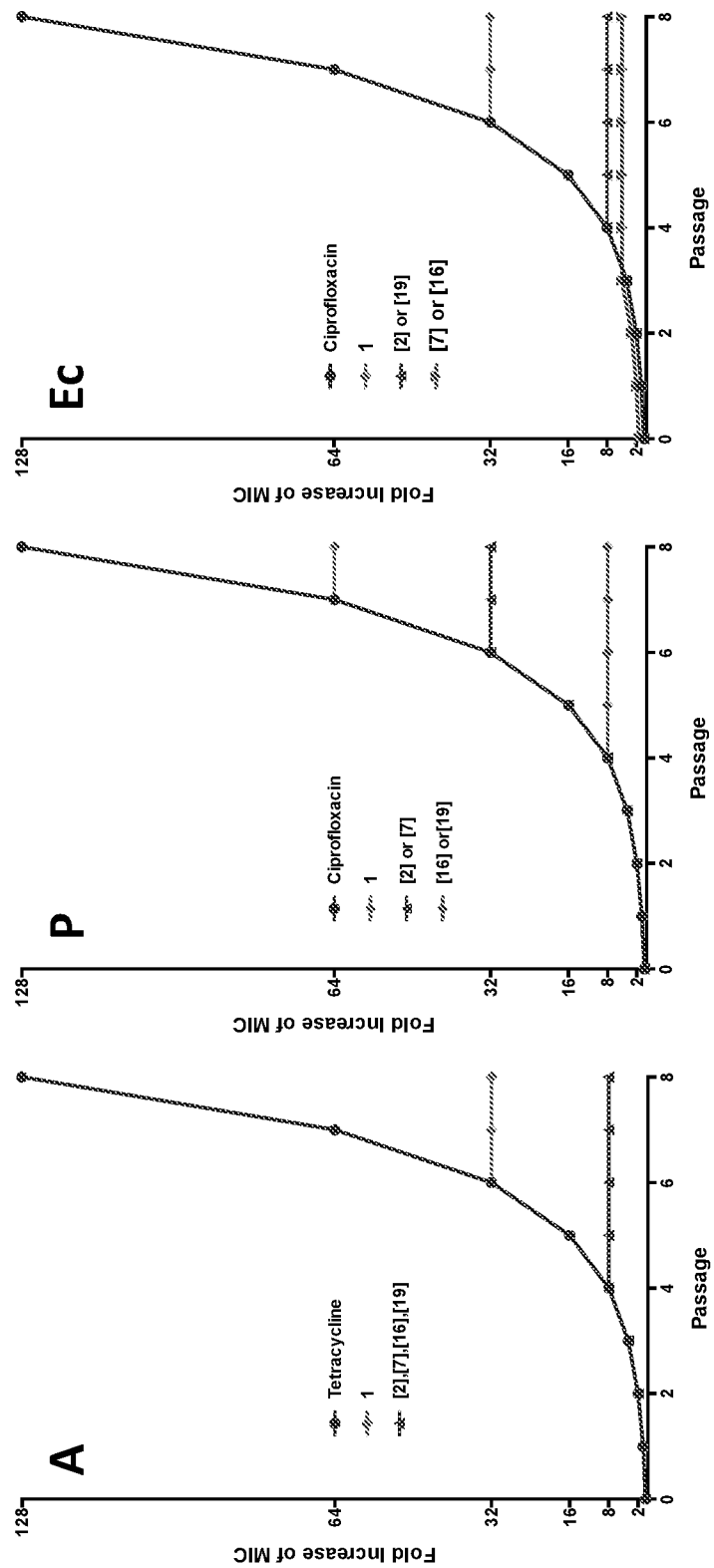

An important attribute of potential antimicrobial agents is that the development of resistance to their action is not readily attained. Thus, we determined the spontaneous mutation frequencies for each of our five frontrunner agents. Despite numerous attempts using agar containing compounds at concentrations ranging from 2-10×MIC, we could not generate spontaneous mutants for any of the ESKAPE pathogens (>1×10$^{11}$ CFU collectively tested for each organism). This is in good agreement with work by Rideout et al.,[13a] and their study of agents chemically related to the bis-cyclic guanidines, where spontaneous mutants could also not be generated. In the absence of spontaneous mutants, we next performed stepwise resistance assays, by serially passage of ESKAPE organisms in liquid media over 8 separate cycles (1 per day). For each passage, the concentration of front-runner compound was increased two fold; alongside a control agent (*E. faecium* and *A. baumannii*=tetracycline; *P. aeruginosa* and *E. cloacae*=ciprofloxacin; *S. aureus*=vancomycin; *K. pneumoniae*=rifampin). Against *S. aureus*, lead compounds 1 and 2 displayed the smallest increase in MIC, with only a two-fold decrease in sensitivity observed (FIGS. 8A-8B). We also observed limited resistance for 7, where a four-fold increase in MIC was noted after 8 passages. Finally, 16 and 19 both led to a 16-fold reduction in susceptibility, which, whilst higher than our other compounds, was significantly less than that of the control, vancomycin. For this latter agent, we noted a continued doubling of the MIC for every passage up to 128 fold increase in MIC. The control agents for each of the other five pathogens behaved similarly, with continued doubling up to 128 fold of the original MIC. However, in each case, the bis-cyclic guanidines outperformed the existing, approved, control agents. Lead agents 2, 7, 16, and 19 were remarkably effective at limiting resistance development in the Gram negative species *K. pneumoniae*, *A. baumannii*, and *E. cloacae*. Testing with these agents revealed a sensitivity limit of ≤8-fold, with concentrations higher resulting in complete inhibition of bacterial growth. Against *P. aeruginosa*, lead agents 16 and 19 had the smallest increase in sensitivity at 8-fold, a promising observation for a pathogen known to readily develop resistance to antimicrobial agents. As such, there appears to be very limited potential for resistance to our front-runner agents, with no-spontaneous mutation seemingly apparent, and limited room for adaptive tolerance to their affects.

Lead Bis-Cyclic Guanidines are Efficacious During In Vivo Infection.

Figure 9:
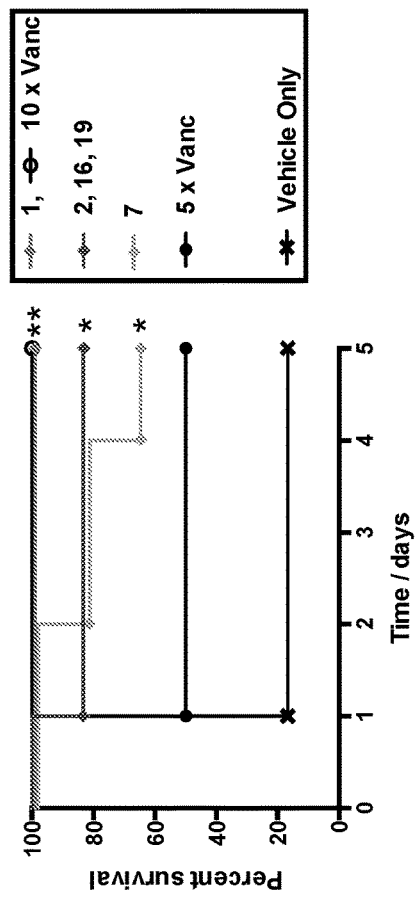
FIG. 9 illustrates a graph of a group for a number of the bis-cyclic guanidines that are efficacious during in vivo infection. Mice were I.P. infected with a lethal dose of *S. aureus*. After 1 h, they were then injected with either front-runner bis-cyclic guanidines (at 2×MIC), vancomycin (positive control, at 5×MIC and 10×MIC) or vehicle alone (negative control). Mice were then monitored for five days, and the significance of mortality measured using a log rank and chi square test with 1-degree of freedom. *=$p>0.05$, **=$p>0.01$.

As a final measure of the suitability of our lead compounds to serve as anti-bacterial agents, we studied their in vivo efficacy in mice. Using MRSA as a representative ESKAPE organism, we infected mice with 1×10$^8$ bacterial cells in 5% mucin via intraperitoneal injection. At 1 h post-infection, mice were then I.V. injected with either vancomycin (positive control), or I.M. with our front runner compounds. Each group of mice was compared to a negative control group receiving only vehicle (45% w/v (2-hydroxypropyl)-β-cyclodextrin in water). At 2×MIC for compound 1, all mice survived the 5 day infection period (FIG. 9). Similarly, compounds 2, 16 and 19 also proved highly efficacious, with only a single mouse succumbing to infection after the first day, and the rest surviving through day 5. Finally, compound 7 was only marginally less effective, with 1 mouse lost on each of days 2 and 4, which still resulted in statistically significant protection compared to vehicle only controls. When using our control agent vancomycin, we observed 50% protectivity at 5×MIC (not significant), and 100% protectivity at 10×MIC. Based on these encouraging results, we suggest that our lead bis-cyclic guanidines have excellent in vivo activity, even at very low doses.

Conclusions:

The combinatorial scaffold libraries in this study allowed for the assessment of >6 million compounds for antibacterial activity against the ESKAPE pathogens. The screening ultimately identified a bis-cyclic guanidine scaffold with broad spectrum activity towards each of these organisms. The utilization of a positional scanning library (PSL) was crucial in identifying the most effective functional groups at each of the three variant positions of the core scaffold. The PSL data guided synthesis of 27 individual compounds with significantly increased activity towards all 6 ESKAPE pathogens. The five most promising individual compounds were chosen as lead agents for further characterization of antibacterial activity (1, 2, 7, 16, and 19). These lead agents proved to be strongly bactericidal (but not bacteriolytic), had promising abilities to eradicate biofilms created by each of the ESKAPE pathogens, and demonstrated little capacity for the development of resistance. Moreover, the bis-cyclic guanidines proved to be highly selective towards bacteria, revealed by low toxicity towards human lung epithelial cells and erythrocytes. Finally, using a murine model of lethal peritonitis we observed in vivo efficacy of the bis-cyclic guanidines. Taken together we present the discovery of a novel class of bis-cyclic guanidines that have high specificity toward the ESKAPE pathogens in vitro and in vivo, and which display significant promise for development as antibacterial agents.

Materials and Methods

Synthesis of Library 2157 and Individual Compounds and Construction of Scaffold Ranking Plate:

General Synthesis of Bis-Cyclic Guanidines (Scheme 1):

Library 2157 as well as the individual compounds reported herein (1-54) were synthesized following the same synthetic scheme (Scheme 1).[33,34,17] Utilizing the "tea-bag" methodology[35], 100 mg of p-methylbenzhydrylamine (MBHA) resin (1.1 mmol/g, 100-200 mesh) was sealed in a mesh "tea-bag," neutralized with 5% diisopropylethylamine (DIEA) in dichloromethane (DCM), and subsequently swelled with additional DCM washes. Fmoc-L-Lys(Boc)-OH was coupled in Dimethylformamide (0.1M DMF) for 120 minutes in the presence of Diisopropylcarbodiimide (DIC, 6 equiv.) and 1-Hydroxybenzotriazole hydrate (HOBt, 6 equiv.) (1, Scheme 1). The Fmoc protecting group was removed with 20% piperidine in DMF for 20 minutes and the $R_1$ carboxylic acids was coupled (10 equiv) in the presence of DIC (10 equiv) and HOBt (10 equiv) in DMF (0.1M) for 120 minutes (2, Scheme 1). The Boc protecting group was then removed with Trifluoroacetic Acid (TFA) in DCM for 30 minutes and subsequently neutralized with 5% DIEA/DCM (3×). Boc-Amino Acids ($R_2$) were coupled utilizing standard coupling procedures (6 equiv.) with DIC (6 equiv.) and HOBt (6 equiv.) in DMF (0.1M) for 120 minutes. The Boc group was removed with 55% TFA/DCM for 30 minutes and subsequently neutralized with 5% DIEA/DCM (3×). Carboxylic acids ($R_3$) were coupled (10 equiv) in the presence of DIC (10 equiv) and HOBt (10 equiv) in DMF (0.1M) for 120 minutes (3, Scheme 1). All coupling reactions were monitored for completion by the Ninhydrin test. Reductions were performed in a 4000 mL Wilmad LabGlass vessel under nitrogen. Tetrahydrofuran (THF, 1.0M) borane complex solution was used in 40 fold excess for each amide bond. The vessel was heated to 65° C. and maintained at this temperature for 96 hours. The solution was then removed and the bags washed with THF and methanol (MeOH). Once completely dry, bags were treated overnight with piperidine at 65° C. and washed several times with DMF, DCM, and methanol (4, Scheme 1). Before proceeding, the completion of reduction was monitored by LCMS analysis of a control compound (4, Scheme 1) that was cleaved from solid support (HF, anisole, 0° C. 7 hr). Cyclization (5, Scheme 1) was performed with a 5-fold excess (for each cyclization) of cyanogen bromide (CNBr) in a 0.1M anhydrous DCM solution overnight. Following the cyclization, the bags were rinsed with DMF and DCM. The resin was cleaved with HF in the presence of anisole in an ice bath at 0° C. for 90 minutes (6, Scheme 1). After removal of the HF by gaseous $N_2$ the products were then extracted from the vessels with 95% acetic acid in water, transferred to scintillation vials, frozen and lyophilized. Compounds were then reconstituted in 50% acetonitrile and water, frozen and lyophilized three more times. For initial screening (data shown in section "Screening of individual compounds") the individual compounds were tested as crude material in case the activity was driven by a side reaction that was also present in the original positional scanning library. After initial screening, the 5 front runner compounds, 1, 2, 7, 16 and 19 were selected for purification and all data reported in section "Exploring the antibacterial activity of frontrunner agents using a library of ESKAPE pathogen isolates" and beyond is from the purified stock of these five compounds. All chirality was generated from the corresponding amino acids. As previously reported by our group and others, the reduction of polyamides with borane is free of racemization[36,36b,37]. For those compounds with multiple chiral centers, a single diastereomer was obtained.

LCMS Analysis of Crude Material:

Purity and identity of initial crude compounds was verified using a Shimadzu 2010 LCMS system, consisting of a LC-20AD binary solvent pumps, a DGU-20A degasser unit, a CTO-20A column oven, and a SIL-20A HT auto sampler. A Shimadzu SPD-M20A diode array detector was used for detections. A full spectra range of 190-600 nm was obtained during analysis. Chromatographic separations were obtained using a Phenomenex Luna C18 analytical column (5 µm, 50×4.6 mm i.d.). The column was protected by a Phenomenex C18 column guard (5 µm, 4×3.0 mm i.d.). All equipment was controlled and integrated by Shimadzu LCMS solutions software version 3. Mobile phases for LCMS analysis were HPLC grade or LCMS grade obtained from Sigma Aldrich and Fisher Scientific. The mobile phases consisted of a mixture of LCMS grade Acetonitrile/water (both with 0.1% formic acid for a pH of 2.7). The initial setting for analysis was 5% Acetonitrile (v/v), then linearly increased to 95% Acetonitrile over 6 minutes. The gradient was then held at 95% Acetonitrile for 2 minutes before being linearly decreased to 5% over 0.10 minutes and held until stop for an additional 1.90 minutes. The total run time was equal to 12 minutes, the total flow rate was 0.5 mL/minute. The column oven and flow cell temperature for the diode array detector was 30° C. The auto sampler temperature was held at 15° C., and 5 uL was injected for analysis.

HPLC Purification (Compounds 1, 2, 7, 16 and 19):

All purifications were performed on a Shimadzu Prominence preparative HPLC system, consisting of LC-8A binary solvent pumps, a SCL-10A system controller, a SIL-10AP auto sampler, and a FRC-10A fraction collector. A Shimadzu SPD-20A UV detector was used for detection. The wavelength was set at 214 nm during analysis. Chromatographic separations were obtained using a Phenomenex Luna C18 preparative column (5 µm, 150×21.5 mm i.d.). The column was protected by a Phenomenex C18 column guard (5 µm, 15×21.2 mm i.d.). Prominence prep software was used to set all detection and collection parameters. The mobile phases for HPLC purification were HPLC grade obtained from Sigma Aldrich and Fisher Scientific. The mobile phase consisted of a mixture of Acetonitrile/water (both with 0.1% formic acid). The initial setting for separation was 2% Acetonitrile, which was held for 2 minutes, then the gradient was linearly increased to 20% Acetonitrile over 4 minutes. The gradient was then linearly increased to 55% Acetonitrile over 36 minutes. The HPLC system was set to automatically flush and re-equilibrate the column after each run for a total of 4 column volumes. The total flow rate was set to 12 mL/min and the total injection volume was set to 3900 uL. The fraction collector was set to collect from 6 to 40 minutes. The corresponding fractions were then combined and lyophilized.

LCMS Analysis of Purified Compounds:

The purity and identity of purified compounds 1, 2, 7, 16 and 19 (all data reported from section "Exploring the antibacterial activity of frontrunner agents using a library of ESKAPE pathogen isolates" through to the end of the manuscript was generated with purified compounds) were carried out using a Shimadzu 2020 LCMS system, consisting of a LC-20AD binary solvent pumps, a DGU-20A degasser unit, a CTO-20A column oven and a SIL-20A HT auto sampler. A Shimadzu SPD-M20A diode array detector was used for detections. A full spectra range of 190-460 nm was obtained during analysis. Chromatographic separations were obtained using a Phenomenex Gemini C18 analytical column (5 μm, 250×2 mm i.d.). The column was protected by a Phenomenex C18 column guard (5 μm, 4×2 mm i.d.). All equipment was controlled and integrated by Shimadzu Lab Solutions software version 5.53 SP3. Three different sets of conditions were used for analysis. Condition 1 (Acetonitrile/water pH 2.7): The mobile phase consisted of a mixture of LCMS grade Acetonitrile/water (both with 0.1% formic acid for a pH of 2.7) with initial settings for analysis of 5% organic mobile phase (v/v), which was linearly increased to 95% organic mobile phase over 38 minutes. The gradient was then held at 95% organic mobile phase for 4 minutes, then linearly decreased to 5% over 2 minutes and held until stop for an additional 1 minute. The total run time was equal to 46 minutes. Condition 2 (Methanol/water pH 7.4): The mobile phase consisted of LCMS grade Methanol/water containing 10 mM Ammonium Bicarbonate (adjusted pH 7.4 with formic acid). The initial setting for analysis was 5% organic mobile phase (v/v), which was linearly increased to 95% organic mobile phase over 38 minutes. The gradient was then held at 95% organic mobile phase for 4 minutes, then linearly decreased to 5% over 2 minutes and held until stop for an additional 1 minute. The total run time was equal to 46 minutes. Condition 3 (Methanol/water pH 5.14): The mobile phase consisted of LCMS grade Methanol/water containing 50 mM Ammonium Formate (adjusted pH 5.14 with formic acid). The initial setting for analysis was 60% Methanol (v/v), which was linearly increased to 80% Methanol over 10 minutes, before the gradient was linearly increased to 83% Methanol over 25 minutes. The gradient was again linearly increased to 95% Methanol over 3 minutes and held at 95% for an additional 4 minutes. Then the gradient was linearly decreased to 60% Methanol over 2 minutes and held until stop for a total run time of 46 minutes.

NMR Analysis of Purified Compounds:

$^1$H and $^{13}$C NMR spectra were obtained utilizing the Bruker 400 Ascend (400 and 100 MHz, respectively). NMR chemical shifts were reported in δ (ppm) using the δ 7.26 signal of CDCl$_3$ ($^1$H NMR) and the δ 77.16 signal of CDCl$_3$ ($^{13}$C NMR) as internal standards.

(S)-4-butyl-3-hexyl-1-(4-((S)-2-imino-3-(3-(trifluoromethyl)phenethyl)imidazolidin-4-yl)butyl)imidazolidin-2-imine (1)

Using the synthetic approach described in Scheme 1 for the synthesis of compound 1 was synthesized using the following reagents: (α-α-α-Trifluoro-m-Tolyl) acetic acid (R$_1$), Boc-L-Norleucine (R$_2$), Heptanoic Acid (R$_3$). Final crude product was purified by HPLC as described above. 1H NMR (400 MHz, CHLOROFORM-d): δ 8.7 (br. s., 2H) 7.5-7.6 (m, 2H) 7.4-7.5 (m, 2H) 4.0-4.1 (m, 1H) 3.8-3.9 (m, 1H) 3.5-3.7 (m, 5H) 3.3-3.5 (m, 2H) 3.1-3.3 (m, 3H) 2.9-3.1 (m, 2H) 1.7-1.9 (m, 1H) 1.5-1.6 (m, 5H) 1.5 (d, J=8.1 Hz, 2H) 1.2-1.4 (m, 13H) 0.9-1.0 (m, 6H); 13C NMR (100 MHz, CHLOROFORM-d) δ 169.0, 159.5, 157.2, 139.4, 132.7, 129.2, 56.4, 51.0, 46.1, 45.1, 43.0, 42.8, 33.5, 31.6, 31.5, 31.4, 29.0, 26.8, 26.5, 26.4, 22.5, 22.4, 20.5, 14.0, 13.9; LCMS (ESI+) Calcd for C$_{30}$H$_{49}$F$_3$N$_6$: 551.75, found [M+H]+: 551.35. LCMS retention time (214 nm) Condition 1 (Acetonitrile/water pH 2.7): 17.168 min. Condition 2 (Methanol/water pH 7.4) 33.528 min. Condition 3 (Methanol/water pH 5.14): 9.254 min.

(S)-4-butyl-3-(4-cyclohexylbutyl)-1-(4-((S)-2-imino-3-(3-(trifluoromethyl)phenethyl)imidazolidin-4-yl)butyl)imidazolidin-2-imine (2)

Using the synthetic approach described in Scheme 1 for the synthesis of compound 2 was synthesized using the following reagents: (α-α-α-Trifluoro-m-Tolyl) acetic acid (R$_1$), Boc-L-Norleucine (R$_2$), Cyclohexanebutyric Acid (R$_3$). Final crude product was purified by HPLC as described above. 1H NMR (400 MHz, CHLOROFORM-d): δ 8.7 (br. s., 2H) 7.5-7.6 (m, 2H) 7.4-7.5 (m, 2H) 4.0-4.1 (m, 1H) 3.8 (d, J=9.9 Hz, 1H) 3.5-3.7 (m, 3H) 3.5 (br. s., 1H) 3.3-3.5 (m, 2H) 3.1-3.30 (m, 3H) 2.9-3.0 (m, 2H) 2.2 (br. s., 3H) 2.0 (s, 1H) 1.6-1.9 (m, 6H) 1.5-1.60 (m, 3H) 1.4-1.5 (m, 2H) 1.2-1.4 (m, 12H) 0.8-1.0 (m, 4H); 13C NMR (100 MHz, CHLOROFORM-d) δ 159.5, 157.2, 139.4, 132.7, 129.2, 123.5, 58.6, 56.4, 50.1, 46.1, 45.1, 43.0, 42.8, 37.5, 37.1, 33.5, 33.4, 33.3, 31.5, 31.4, 27.1, 26.6, 26.4, 26.3, 23.9, 22.5, 20.5, 13.9; LCMS (ESI+) Calcd for C$_{33}$H$_{53}$F$_3$N$_6$: 591.81, found [M+H]+: 591.45. LCMS retention time (214 nm) Condition 1 (Acetonitrile/water pH 2.7): 18.363 min. Condition 2 (Methanol/water pH 7.4) 34.487 min. Condition 3 (Methanol/water pH 5.14): 12.048 min.

(S)-4-(cyclohexylmethyl)-3-hexyl-1-(4-((S)-2-imino-3-(3-(trifluoromethyl)phenethyl)imidazolidin-4-yl)butyl)imidazolidin-2-imine (7)

Using the synthetic approach described in Scheme 1 for the synthesis of compound 7 was synthesized using the following reagents: (α-α-α-Trifluoro-m-Tolyl) acetic acid (R$_1$), Boc-L-Cyclohexylalanine (R$_2$), Heptanoic Acid (R$_3$). Final crude product was purified by HPLC as described above. 1H NMR (400 MHz, CHLOROFORM-d): δ 8.7 (br. s., 2H) 7.5-7.6 (m, 2H) 7.4-7.5 (m, 2H) 4.0-4.1 (m, 1H) 3.8-3.9 (m, 1H) 3.5-3.7 (m, 4H) 3.3-3.5 (m, 3H) 3.1-3.3 (m, 3H) 2.8-3.1 (m, 3H) 1.6-1.8 (m, 8H) 1.5-1.6 (m, 4H) 1.2-1.4 (m, 14H) 0.9-1.1 (m, 5H); 13C NMR (100 MHz, CHLOROFORM-d) δ 159.5, 157.2, 139:4, 132.7, 129.2, 77.2, 58.6, 54.7, 51.8, 46.2, 45.2, 43.0, 42.8, 39.8, 34.3, 33.5, 32.5, 31.6, 31.4, 28.9, 26.7, 26.5, 26.3, 26.2, 26.1, 25.9, 22.5, 20.5, 14.0; LCMS (ESI+) Calcd for C$_{33}$H$_{53}$F$_3$N$_6$: 591.81, found [M+H]+: 591.45. LCMS retention time (214 nm) Condition 1 (Acetonitrile/water pH 2.7): 18.380 min. Condition 2 (Methanol/water pH 7.4) 35.664 min. Condition 3 (Methanol/water pH 5.14): 12.373 min.

(S)-1-(4-((S)-3-(4-cyclohexylbutyl)-2-iminoimidazolidin-4-yl)butyl)-4-(cyclohexylmethyl)-3-hexylimidazolidin-2-imine (16)

Using the synthetic approach described Scheme 1 for the synthesis of compound 16 was synthesized using the following reagents: Cyclohexanebutyric Acid (R$_1$), Boc-L-Cyclohexylalanine (R$_2$), Heptanoic Acid (R$_3$). Final crude product was purified by HPLC as described above. 1H NMR (400 MHz, CHLOROFORM-d): δ 8.7 (br. s., 2H) 3.8-3.9 (m, 2H) 3.6-3.8 (m, 5H) 3.4-3.5 (m, 1H) 3.3 (dd, J=9.72, 5.81 Hz, 1H) 3.1-3.2 (m, 3H) 1.5-1.8 (m, 17H) 1.2-1.4 (m, 22H) 1.0-1.2 (m, 2H) 0.8-1.0 (m, 6H); 13C NMR (100 MHz, CHLOROFORM-d) δ 169.1, 159.5, 157.2, 57.8, 54.7, 51.8, 46.1, 45.3, 42.8, 41.9, 39.8, 37.5, 37.2, 34.3, 33.4, 33.3, 32.5, 31.6, 31.4, 28.9, 27.5, 26.8, 26.7, 26.6, 26.5, 26.4, 26.2, 26.1, 25.9, 23.9, 22.6, 20.5, 14.0; LCMS (ESI+) Calcd for C$_{34}$H$_{64}$N$_6$: 557.91, found [M+H]+: 557.50. LCMS retention time (214 nm) Condition 1 (Acetonitrile/water pH 2.7): 19.706 min. Condition 2 (Methanol/water pH 7.4) 37.568 min. Condition 3 (Methanol/water pH 5.14): 14.248 min.

(S)-1-(4-((S)-3-(2-((3S,5S,7S)-adamantan-1-yl)ethyl)-2-iminoimidazolidin-4-yl)butyl)-4-butyl-3-hexylimidazolidin-2-imine (19)

Using the synthetic approach described in Scheme 1 for the synthesis of compound 19 was synthesized using the following reagents: 1-Adamantaneacetic Acid ($R_1$), Boc-L-Norleucine ($R_2$), Heptanoic Acid ($R_3$). Final crude product was purified by HPLC as described above. 1H NMR (400 MHz, CHLOROFORM-d): δ 8.7 (br. s., 2H), 3.9 (dd, J=9.6, 4.7 Hz, 1H), 3.8-3.9 (m, 1H), 3.6-3.8 (m, 5H), 3.4-3.5 (m, 1H), 3.3 (dd, J=9.7, 5.6 Hz, 1H), 3.0-3.3 (m, 3H), 2.0 (br. s., 4H), 1.5-1.8 (m, 18H), 1.2-1.4 (m, 15H), 0.9-1.0 (m, 6H); 13C NMR (100 MHz, CHLOROFORM-d) δ 169.2, 159.5, 157.3, 57.4, 56.4, 51.1, 46.0, 45.4, 42.9, 42.1, 40.5, 36.9, 31.7, 31.6, 31.5, 29.0, 28.5, 26.8, 26.7, 26.6, 26.4, 22.6, 22.5, 20.5, 14.0, 13.9; LCMS (ESI+) Calcd for $C_{33}H_{60}N_5$: 541.87, found [M+H]+: 541.45. LCMS retention time (214 nm) Condition 1 (Acetonitrile/water pH 2.7): 18.270 min. Condition 2 (Methanol/water pH 7.4) 36.038 min. Condition 3 (Methanol/water pH 5.14): 12.692 min.

Positional Scanning Library 2157:

Positional scanning library 2157 was synthesized using the general Scheme 1. The positional scanning library incorporates both individual and mixtures of amino acids ($R_2$) and carboxylic acids ($R_1$ and $R_3$). The synthetic technique facilitates the generation of information regarding the likely activity of individual compounds from screening of the library.[14,38,39] Equimolar isokinetic ratios have previously been determined and calculated for each of the amino and carboxylic acids utilized for the respective mixtures.[40,41] The bis-cyclic guanidine library 2157 has a total diversity of 45,864 compounds (42×26×42=45,864). The $R_1$ and $R_3$ positions as shown in Scheme 1 (6) each consist of 42 carboxylic acids and the $R_2$ contains 26 amino acids.

Scaffold Ranking Library:

The scaffold ranking library contains one sample for each of the 37 positional scanning libraries tested. Each of these samples contains an approximate equal molar amount of each compound in that library. So, for example, the sample 2157 in the scaffold ranking library contains 45,864 compounds in approximately equal molar amounts. These samples can be prepared by mixing the cleaved products of the complete positional scanning library, as was the case for sample 2157, or they can be synthesized directly as a single mixture.[14,6]

Bacterial Strains and Growth Conditions.

For this study we used a representative panel of multi-drug resistant clinical ESKAPE pathogen isolates (Supplemental Table S6).[42,43,3a,44,45] Gram-positive organisms were grown in tryptic soy broth media (TSB), whilst Gram-negative organisms were grown in lysogeny Broth (LB), as described by us previously.[43] MIC and MBC determination assays.

The minimum inhibitory concentration (MIC) for the combinatorial libraries, deconvolved 2157 library, and individual compounds were determined as follows. Broth cultures of ESKAPE strains were grown overnight before being diluted 1 in 1,000 in fresh media. Sterile 96-well plates were loaded with culture and compounds (in DMF) were added at decreasing concentrations to equal a total volume of 200 µl per well. Care was taken to not add more than 2.0% DMF to any well. Plates were then incubated at 37° C., and MICs determined after 24 hours by visual inspection for a lack of turbidity in wells. All assays were performed in triplicate with identical results obtained. For both the scaffold ranking and positional scanning samples, relative broad-spectrum activity was determined via stacked scores:

$$StackedScore = \sum_{i=E,S,K,A,P,E} \frac{100}{MIC \text{ of } i^{th} \text{ Pathogen}}$$

Minimal bactericidal concentrations (MBC) were determined for 1, 2, 7, 16, and 19 using MIC cultures. Briefly, compound was washed by centrifugation and serial dilution, before plating on Tryptic Soy Agar (TSA). Plates were incubated for 24 hours at 37° C. and cell viability assessed by determining CFU/ml at each concentration, for every compound. Percent recovery was then determined compared to CFU/ml from no drug controls. All concentrations and controls were tested using three biological replicates, alongside two technical replicates for each data point.

Time Kill Assay.

Time kill assays were performed in a 96-well microtiter plate using a BioTek Synergy2 plate reader. To prepare bacterial cultures, stationary phase MRSA cells were inoculated into fresh TSB and grown for 3 hours. After this time, cultures were inoculated into a 96-well microtiter plate at an $OD_{600}$ of 0.5, followed by the addition of test agent at MIC concentrations. In parallel, 2.0% sodium dodecyl sulfate (SDS), 0.001% benzalkonium chloride, 0.001% benzethonium chloride, and 4 µM lysostaphin were used as positive controls. Doxycycline (200 µM), a bacteriostatic translation inhibitor that does not result in cell lysis was used as a negative control. Assays were performed in triplicate over the span of 130 minutes, with $OD_{600}$ readings taken every 10 minutes.

MBEC Determination Assays.

The minimum biofilm eradication concentration (MBEC) was determined in 96-well microtiter plates as follows. Broth cultures of ESKAPE strains were grown using the conditions described above. Biofilms for each of the ESKAPE pathogens were generated from these as we have previously described for S. aureus, however human serum was not used for non-staphylococcal organisms.[44,46] For all organisms, biofilms were developed by standardizing an overnight culture into fresh media to an $OD_{600}$ of 0.5 and adding 150 µl into each well of a 96-well microtiter plate. Biofilms were allowed to develop for 24 hours, before the media was carefully removed and 200 µl of fresh media added containing a range of front-runner agent (above and below MIC). These cultures were incubated at 37° C. overnight alongside no drug controls. After 24 hours, the media was removed from wells and the biofilm resuspended in phosphate buffered saline (PBS). Cultures were mixed by vigorous pipetting, before being serially diluted in PBS, and plated in duplicate on relevant agar. Plates were incubated at 37° C. for 24 hours, and CFUs determined by enumeration. Each analysis was performed using three technical replicates, and antibiofilm activity was determined by comparing treated to untreated samples.

Cytotoxicity Assay.

Cytotoxicity assays were performed using human A549 cells (adenocarcinomic human alveolar epithelial cells), as described by us previously.[44] Briefly, cells were cultured in F-12K Nutrient mixture (Kaighn's Modification) media containing L-glutamine, supplemented with 10% fetal bovine serum and 1% penicillin-streptomycin for 3 days at 37° and 5% $CO_2$. Cells were then diluted to $1.0 \times 10^5$ ml$^{-1}$ using F-12K supplemented media, and added to 96 well tissue culture plates at a volume of 100 µl. Plates were incubated for 24 hours at 37° C. and 5% $CO_2$, allowing the cells to adhere to the plastic. After this time, media was carefully removed and 200 µl fresh F-12 added with test compounds at concentrations ranging from 1-125 µM. Plates were then incubated for 48 hours at 37° C. and 5% $CO_2$. After 48 hours the media was removed, and new media added containing MTT (3-(4, 5-dimethylthiazol-2-yl)-2,5-diphenyltetrazolium bromide), followed by incubation for four hours at 37°

C. and 5% $CO_2$. After 4 h, 50 μl of media was removed, replaced with DMSO and incubated for ten minutes at 37° C. in order to solubilize any formazan produced. A Biotek plate reader was used to measure the absorbance of formazan production at 540 nM, and $IC_{50}$ values were determined for each of the five compounds. Front runners were solvated in 45% w/v (2-hydroxypropyl)-β-cyclodextrin in water for these studies; which was also used alone as a negative control. $IC_{50}$ values were determined for each compound by comparison to vehicle only controls, to assess toxicity to human cells.

Hemolysis Assay.

A hemolysis assay was performed using whole human blood (Bioreclamation), as described previously,[47] with the following modifications. Human red blood cells (hRBCs) were resuspended 20% v/v in 1×HA buffer (4.25 ml 10% NaCl; 1 ml $CaCl_2$ in 50 ml sterile water), and lead agents were added at a concentration of 10 μM, to a final volume of 100 μl. Cells were incubated for 15 minutes at 37° C. before being centrifuged at 5,500 g for 1 minute to pellet non-lysed hRBCs. The supernatant was removed, added to a 96-well microtiter plate and the $OD_{543}$ read using a Biotek synergy2 plate reader. The negative control was vehicle only (DMF), and the positive control was 1.0% triton X-100. Assays were performed in triplicate, with data displayed as percent hemolysis compared to controls, defined as: Percent Hemolysis=($OD_{543}$ test sample–$OD_{543}$ no drug control)/ ($OD_{543}$ triton X-100–$OD_{543}$ no drug control)×100.

Resistance Assays.

In order to test potential resistance towards the lead agents, a serial passage assay was performed alongside control compounds (*E. faecium* and *A. baumanni*=tetracycline; *P. aeruginosa* and *E. cloacae*=ciprofloxacin; *S. aureus*=vancomycin; *K. pneumoniae*=rifampin). ESKAPE pathogens were grown overnight in liquid media at 37° C. These cultures were then diluted 1:100 in fresh media, and seeded into a 96-well plate. Lead bis-cyclic guanidines or control agents were added to respective wells at half MIC concentrations. Plates were then incubated for 24 hours at 37° C., with bacteria removed from these cultures on the following day, to inoculate fresh media (1:100 dilution) containing compounds at a 2-fold higher concentrations. These were then grown overnight, and the procedure repeated for a total of eight days. The cultures were observed for a lack of growth, indicating strains were no longer able to resist the action of a given compound. Each experiment was performed in triplicate, yielding identical results.

Assessing Efficacy During Bacterial Infection In Vivo.

A murine model of lethal peritonitis was used to demonstrate the effectiveness of the bis-cyclic guanidines to clear bacterial infections, as described by us previously.[43] All animal studies received written approval after review by the Institutional Animal Care & Use Committee in the Division of Comparative Medicine & Division of Research Integrity & Compliance at the University of South Florida. Six mice per group were injected with 1×10⁸ CFU $ml^{-1}$ of *Staphylococcus aureus* (USA300 strain FPR3757) in PBS containing 5% mucin. After 1 h, mice were inoculated with either 5×MIC (4 nM) or 10×MIC (8 nM) of vancomyin (I.V., positive control); 2×MIC (2 μM) of front runner agents (I.M., test group); or vehicle alone (I.V.; 45% w/v (2-hydroxypropyl)-β-cyclodextrin in water; negative control). Mice were monitored twice daily for five days to assess mortality. The clinical endpoint of this study was when the mice reached a pre-moribund state. Characteristics of pre-moribund state include: hunched posture, rapid, shallow and/or labored breathing, ruffled fur, lethargy, failure to respond to stimuli, soiled anogenital area, paralysis, paresis, head tilt, circling, vocalizations, non-purposeful movements and/or were unable to eat or drink. Those mice reaching this state prior to the completion of the 5 day infection period were euthanized. The number of mice surviving between control and treatment groups was compared and analyzed for statistical significance using a log rank test.

SAS Maps:

SAS maps were generated following a standard and well-validated protocol.[7,20] Briefly, for each pair of compounds ith and jth, potency differences were determined as the absolute difference between their $pIC_{50}$ activity values. On a relative scale, the potency similarity ($PS_{i,j}$) was measured with the expression:

$$PS_{i,j} = 1 - \frac{|A_i - A_j|}{\max - \min}$$

where $A_i$ and $A_j$ are the activity values of the ith and jth molecules, and max-min indicates the range of activities in the data set. Pairwise structural similarities were computed using the Tanimoto coefficient[48] with radial fingerprints as implemented in Canvas.[25] Property similarities were computed with 6 continuous coordinates: MW, PSA, A log P, RB, HBA and HBD.

Properties were auto-scaled with mean centering using the equation:[49]

$$p_{ki} = \frac{P_{ki} - \overline{P_k}}{\sigma_{P_k}}$$

where $p_{ki}$ denotes the scaled version of the kth property for the ith molecule, $P_{ki}$ denotes the unscaled value, and $\overline{P_k}$ and $\sigma_{P_k}$ denote, respectively, the mean and standard deviation of the kth property over all molecules in the study. The Euclidean distance between a pair of molecules in the property space was then computed with the expression:

$$d_{ij} = \left[ \sum_{k=1}^{K} (p_{ki} - p_{kj})^2 \right]^{1/2}$$

where $d_{ij}$ denotes the Euclidean distance between the ith and jth molecules; $P_{ki}$ and $P_{kj}$ denote the value of the scaled property k of the ith and jth molecules, respectively. In this work K=6 for the four physicochemical properties. Then, Euclidean distances were scaled from 0 to 1 as follows:

$$sd_{ij} = \frac{d_{ij} - \min d_{ij}}{\max d_{ij} - \min d_{ij}}$$

where $sd_{ij}$ is the scaled distance, and max $d_{ij}$ and min $d_{ij}$ indicate the range of distances in the data set. Pairwise property similarities were measured with the expression:

$$PS_{ij} = 1 - sd_{ij}$$

where $PS_{ij}$ represents the molecular similarity using four continuous descriptors of the ith and jth molecules, and $sd_{ij}$ is the scaled distance.

REFERENCES

1. Klevens, R. M.; Edwards, J. R.; Richards, C. L., Jr.; Horan, T. C.; Gaynes, R. P.; Pollock, D. A.; Cardo, D. M., Estimating health care-associated infections and deaths in U.S. hospitals, 2002. *Public health reports* 2007, 122 (2), 160-6.
2. Rice, L. B., Progress and challenges in implementing the research on ESKAPE pathogens. *Infection control and hospital epidemiology: the official journal of the Society of Hospital Epidemiologists of America* 2010, 31 Suppl 1, S7-10.
3. (a) Jacobs, A. C.; Hood, I.; Boyd, K. L.; Olson, P. D.; Morrison, J. M.; Carson, S.; Sayood, K.; Iwen, P. C.; Skaar, E. P.; Dunman, P. M., Inactivation of Phospholipase D Diminishes *Acinetobacter baumannii* Pathogenesis. *Infection and Immunity* 2010, 78 (5), 1952-1962; (b) Kahrstrom, C. T., Entering a post-antibiotic era? *Nat Rev Micro* 2013, 11 (3), 146-146.
4. Boucher, Helen W.; Talbot, George H.; Bradley, John S.; Edwards, John E.; Gilbert, D.; Rice, Louis B.; Scheld, M.; Spellberg, B.; Bartlett, J., Bad Bugs, No Drugs: No ESKAPE! An Update from the Infectious Diseases Society of America. *Clinical Infectious Diseases* 2009, 48 (1), 1-12.
5. (a) Arias, C. A.; Murray, B. E., Antibiotic-Resistant Bugs in the 21st Century—A Clinical Super-Challenge. *New England Journal of Medicine* 2009, 360 (5), 439-443; (b) Falagas, M. E.; Tansarli, G. S.; Karageorgopoulos, D. E.; Vardakas, K. Z., Deaths Attributable to Carbapenem-Resistant Enterobacteriaceae Infections. *Emerging Infectious Diseases* 2014, 20 (7), 1170-1175; (c) Souli, M.; Galani, I.; Giamarellou, H., Emergence of extensively drug-resistant and pandrug-resistant Gram-negative bacilli in Europe. *Euro surveillance: bulletin Europeen sur les maladies transmissibles=European communicable disease bulletin* 2008, 13 (47).
6. Santos, R. G.; Appel, J. R.; Giulianotti, M. A.; Edwards, B. S.; Sklar, L. A.; Houghten, R. A.; Pinilla, C., The mathematics of a successful deconvolution: a quantitative assessment of mixture-based combinatorial libraries screened against two formylpeptide receptors. *Molecules* 2013, 18 (6), 6408-24.
7. Medina-Franco, J. L.; Martínez-Mayorga, K.; Bender, A.; Marín, R. M.; Giulianotti, M. A.; Pinilla, C.; Houghten, R. A., Characterization of Activity Landscapes Using 2D and 3D Similarity Methods: Consensus Activity Cliffs. *Journal of Chemical Information and Modeling* 2009, 49 (2), 477-491.
8. López-Vallejo, F.; Giulianotti, M. A.; Houghten, R. A.; Medina-Franco, J. L.,
Expanding the medicinally relevant chemical space with compound libraries. *Drug Discovery Today* 2012, 17 (13-14), 718-726.
9. Zhou, Z.; Wei, D.; Guan, Y.; Zheng, A.; Zhong, J.-J., Extensive in vitro activity of guanidine hydrochloride polymer analogs against antibiotics-resistant clinically isolated strains. *Materials Science and Engineering: C* 2011, 31 (8), 1836-1843.
10. Kalia, J.; Swartz, K. J., Elucidating the Molecular Basis of Action of a Classic Drug: Guanidine Compounds As Inhibitors of Voltage-Gated Potassium Channels. *Molecular Pharmacology* 2011, 80 (6), 1085-1095.
11. Bera, S.; Zhanel, G. G.; Schweizer, F., Antibacterial activity of guanidinylated neomycin B- and kanamycin A-derived amphiphilic lipid conjugates. *Journal of Antimicrobial Chemotherapy* 2010, 65 (6), 1224-1227.
12. Ling, L. L.; Schneider, T.; Peoples, A. J.; Spoering, A. L.; Engels, I.; Conlon, B. P.; Mueller, A.; Schaberle, T. F.; Hughes, D. E.; Epstein, S.; Jones, M.; Lazarides, L.; Steadman, V. A.; Cohen, D. R.; Felix, C. R.; Fetterman, K. A.; Millett, W. P.; Nitti, A. G.; Zullo, A. M.; Chen, C.; Lewis, K., A new antibiotic kills pathogens without detectable resistance. *Nature* 2015.
13. (a) Rideout, M. C.; Boldt, J. L.; Vahi-Ferguson, G.; Salamon, P.; Nefzi, A.; Ostresh, J. M.; Giulianotti, M.; Pinilla, C.; Segall, A. M., Potent antimicrobial small molecules screened as inhibitors of tyrosine recombinases and Holliday junction-resolving enzymes. *Molecular Diversity* 2011, 15 (4), 989-1005; (b) Hensler, M. E.; Bernstein, G.; Nizet, V.; Nefzi, A., Pyrrolidine bis-cyclic guanidines with antimicrobial activity against drug-resistant Gram-positive pathogens identified from a mixture-based combinatorial library. *Bioorganic & medicinal chemistry letters* 2006, 16 (19), 5073-5079.
14. Houghten, R. A.; Pinilla, C.; Giulianotti, M. A.; Appel, J. R.; Dooley, C. T.; Nefzi, A.; Ostresh, J. M.; Yu, Y.; Maggiora, G. M.; Medina-Franco, J. L.; Brunner, D.; Schneider, J., Strategies for the use of mixture-based synthetic combinatorial libraries: scaffold ranking, direct testing in vivo, and enhanced deconvolution by computational methods. *Journal of combinatorial chemistry* 2008, 10 (1), 3-19.
15. Minond, D.; Cudic, M.; Bionda, N.; Giulianotti, M.; Maida, L.; Houghten, R. A.; Fields, G. B., Discovery of Novel Inhibitors of a Disintegrin and Metalloprotease 17 (ADAM17) Using Glycosylated and Non-glycosylated Substrates. *Journal of Biological Chemistry* 2012, 287 (43), 36473-36487.
16. Reilley, K. J.; Giulianotti, M.; Dooley, C. T.; Nefzi, A.; McLaughlin, J. P.; Houghten, R. A., Identification of two novel, potent, low-liability antinociceptive compounds from the direct in vivo screening of a large mixture-based combinatorial library. *The AAPS journal* 2010, 12 (3), 318-29.
17. Wu, J.; Zhang, Y.; Maida, L. E.; Santos, R. G.; Welmaker, G. S.; LaVoi, T. M.; Nefzi, A.; Yu, Y.; Houghten, R. A.; Toll, L.; Giulianotti, M. A., Scaffold ranking and positional scanning utilized in the discovery of nAChR-selective compounds suitable for optimization studies. *Journal of medicinal chemistry* 2013, 56 (24), 10103-17.
18. Ranjit, D. K.; Rideout, M. C.; Nefzi, A.; Ostresh, J. M.; Pinilla, C.; Segall, A. M., Small molecule functional analogs of peptides that inhibit lambda site-specific recombination and bind Holliday junctions. *Bioorganic & medicinal chemistry letters* 2010, 20 (15), 4531-4.
19. Mok, N. Y.; Brenk, R.; Brown, N., Increasing the Coverage of Medicinal Chemistry-Relevant Space in Commercial Fragments Screening. *Journal of Chemical Information and Modeling* 2014, 54 (1), 79-85.
20. Singh, N.; Guha, R.; Giulianotti, M. A.; Pinilla, C.; Houghten, R. A.; Medina-Franco, J. L., Chemoinformatic analysis of combinatorial libraries, drugs, natural products, and molecular libraries small molecule repository. *Journal of chemical information and modeling* 2009, 49 (4), 1010-24.
21. Maggiora, G. M., On outliers and activity cliffs—why QSAR often disappoints. *Journal of chemical information and modeling* 2006, 46 (4), 1535.
22. Shanmugasundaram, V. M.; G. M., Characterizing Property and ActiVity Landscapes Using an Information-Theoretic Approach. In *222nd American Chemical Society National Meeting*, Chicago, Ill., United States, 2001.

23. Medina-Franco, J. L., Scanning structure-activity relationships with structure-activity similarity and related maps: from consensus activity cliffs to selectivity switches. *Journal of chemical information and modeling* 2012, 52 (10), 2485-93.
24. Medina-Franco, J.; Martinez-Mayorga, K.; Giulianotti, M.; Houghten, R.; Pinilla, C., Visualization of the Chemical Space in Drug Discovery. *Current Computer Aided-Drug Design* 2008, 4 (4), 322-333.
25. Sastry, M.; Lowrie, J. F.; Dixon, S. L.; Sherman, W., Large-Scale Systematic Analysis of 2D Fingerprint Methods and Parameters to Improve Virtual Screening Enrichments. *Journal of Chemical Information and Modeling* 2010, 50 (5), 771-784.
26. Rogers, D.; Hahn, M., Extended-Connectivity Fingerprints. *Journal of Chemical Information and Modeling* 2010, 50 (5), 742-754.
27. Santos, R. G.; Giulianotti, M. A.; Houghten, R. A.; Medina-Franco, J. L., Conditional Probabilistic Analysis for Prediction of the Activity Landscape and Relative Compound Activities. *Journal of Chemical Information and Modeling* 2013, 53 (10), 2613-2625.
28. Stumpfe, D.; Hu, Y.; Dimova, D.; Bajorath, J., Recent Progress in Understanding Activity Cliffs and Their Utility in Medicinal Chemistry. *Journal of Medicinal Chemistry* 2014, 57 (1), 18-28.
29. Garvey, M. I.; Piddock, L. J. V., The Efflux Pump Inhibitor Reserpine Selects Multidrug-Resistant *Streptococcus pneumoniae* Strains That Overexpress the ABC Transporters PatA and PatB. *Antimicrobial Agents and Chemotherapy* 2008, 52 (5), 1677-1685.
30. Chen, M.; Yu, Q.; Sun, H., Novel Strategies for the Prevention and Treatment of Biofilm Related Infections. *International Journal of Molecular Sciences* 2013, 14 (9), 18488-18501.
31. Sanchez, C. J.; Mende, K.; Beckius, M. L.; Akers, K. S.; Romano, D. R.; Wenke, J. C.; Murray, C. K., Biofilm formation by clinical isolates and the implications in chronic infections. *BMC Infectious Diseases* 2013, 13 (1), 47.
32. Kristich, C. J.; Li, Y. H.; Cvitkovitch, D. G.; Dunny, G. M., Esp-independent biofilm formation by *Enterococcus faecalis*. *Journal of bacteriology* 2004, 186 (1), 154-63.
33. Nefzi, A.; Giulianotti, M. A.; Houghten, R. A., Solid-phase synthesis of bis-heterocyclic compounds from resin-bound orthogonally protected lysine. *Journal of combinatorial chemistry* 2001, 3 (1), 68-70.
34. Nefzi, A.; Ostresh, J. M.; Yu, Y.; Houghten, R. A., Combinatorial chemistry: libraries from libraries, the art of the diversity-oriented transformation of resin-bound peptides and chiral polyamides to low molecular weight acyclic and heterocyclic compounds. *The Journal of organic chemistry* 2004, 69 (11), 3603-9.
35. Houghten, R. A., General method for the rapid solid-phase synthesis of large numbers of peptides: specificity of antigen-antibody interaction at the level of individual amino acids. *Proceedings of the National Academy of Sciences of the United States of America* 1985, 82 (15), 5131-5.
36. (a) Ostresh, J. M.; Schoner, C. C.; Hamashin, V. T.; Nefzi, A.; Meyer, J.-P.; Houghten, R. A., Solid-Phase Synthesis of Trisubstituted Bicyclic Guanidines via Cyclization of Reduced N-Acylated Dipeptides. *The Journal of organic chemistry* 1998, 63 (24), 8622-8623; (b) Nefzi, A.; Ostresh, J. M.; Houghten, R. A., Parallel solid phase synthesis of tetrasubstituted diethylenetriamines via selective amide alkylation and exhaustive reduction of N-acylated dipeptides. *Tetrahedron* 1999, 55 (2), 335-344.
37. Manku, S.; Laplante, C.; Kopac, D.; Chan, T.; Hall, D. G., A Mild and General Solid-Phase Method for the Synthesis of Chiral Polyamines. Solution Studies on the Cleavage of Borane-Amine Intermediates from the Reduction of Secondary Amides. *The Journal of organic chemistry* 2001, 66 (3), 874-885.
38. Houghten, R. A.; Pinilla, C.; Appel, J. R.; Blondelle, S. E.; Dooley, C. T.; Eichler, J.; Nefzi, A.; Ostresh, J. M., Mixture-based synthetic combinatorial libraries. *Journal of medicinal chemistry* 1999, 42 (19), 3743-78.
39. Pinilla, C.; Appel, J. R.; Blanc, P.; Houghten, R. A., Rapid identification of high affinity peptide ligands using positional scanning synthetic peptide combinatorial libraries. *BioTechniques* 1992, 13 (6), 901-5.
40. Acharya, A. N.; Ostresh, J. M.; Houghten, R. A., Determination of isokinetic ratios necessary for equimolar incorporation of carboxylic acids in the solid-phase synthesis of mixture-based combinatorial libraries. *Biopolymers* 2002, 65 (1), 32-9.
41. Ostresh, J. M.; Winkle, J. H.; Hamashin, V. T.; Houghten, R. A., Peptide libraries: determination of relative reaction rates of protected amino acids in competitive couplings. *Biopolymers* 1994, 34 (12), 1681-9.
42. Carroll, R. K.; Burda, W. N.; Roberts, J. C.; Peak, K. K.; Cannons, A. C.; Shaw, L. N., Draft Genome Sequence of Strain CBD-635, a Methicillin-Resistant *Staphylococcus aureus* USA100 Isolate. *Genome announcements* 2013, 1 (4).
43. Van Horn, K. S.; Burda, W. N.; Fleeman, R.; Shaw, L. N.; Manetsch, R., Antibacterial Activity of a Series of N2,N4-Disubstituted Quinazoline-2,4-diamines. *Journal of Medicinal Chemistry* 2014, 57 (7), 3075-3093.
44. Beau, J.; Mahid, N.; Burda, W. N.; Harrington, L.; Shaw, L. N.; Mutka, T.; Kyle, D. E.; Barisic, B.; van Olphen, A.; Baker, B. J., Epigenetic Tailoring for the Production of Anti-Infective Cytosporones from the Marine Fungus *Leucostoma persoonii*. *Marine Drugs* 2012, 10 (12), 762-774.
45. Diep, B. A.; Gill, S. R.; Chang, R. F.; Phan, T. H.; Chen, J. H.; Davidson, M. G.; Lin, F.; Lin, J.; Carleton, H. A.; Mongodin, E. F.; Sensabaugh, G. F.; Perdreau-Remington, F., Complete genome sequence of USA300, an epidemic clone of community-acquired meticillin-resistant *Staphylococcus aureus*. *Lancet* 2006, 367 (9512), 731-9.
46. Kolar, S. L.; Nagarajan, V.; Oszmiana, A.; Rivera, F. E.; Miller, H. K.; Davenport, J. E.; Riordan, J. T.; Potempa, J.; Barber, D. S.; Koziel, J.; Elasri, M. O.; Shaw, L. N., NsaRS is a cell-envelope-stress-sensing two-component system of *Staphylococcus aureus*. *Microbiology* 2011, 157 (Pt 8), 2206-19.
47. Niu, Y.; Padhee, S.; Wu, H.; Bai, G.; Qiao, Q.; Hu, Y.; Harrington, L.; Burda, W. N.; Shaw, L. N.; Cao, C.; Cai, J., Lipo-γ-AApeptides as a New Class of Potent and Broad-Spectrum Antimicrobial Agents. *Journal of Medicinal Chemistry* 2012, 55 (8), 4003-4009.
48. Willett, P.; Barnard, J. M.; Downs, G. M., Chemical Similarity Searching. *Journal of Chemical Information and Modeling* 1998, 38 (6), 983-996.
49. Perez-Villanueva, J.; Santos, R.; Hernandez-Campos, A.; Giulianotti, M. A.; Castillo, R.; Medina-Franco, J. L., Towards a systematic characterization of the antiprotozoal activity landscape of benzimidazole derivatives. *Bioorganic & medicinal chemistry* 2010, 18 (21), 7380-91.

TABLE 1

Antimicrobial activity of front-runner bis-cyclic guanidines. The in vitro antibacterial and cytotoxic properties of the lead bis-cyclic guanidines were assessed. Shown are the antibacterial activity (MIC), the bactericidal capacity ($MBC_{90}$), anti-biofilm properties ($MBEC_{50}$), and toxicity towards human A549 cells ($IC_{50}$). Selectivity windows were also determined in the form of an Activity Index ($IC_{50}$/MIC): note that only 1 value is given because all compounds have the same MIC against each of the ESKAPE pathogens.

| | MIC (µM) | | | | | | $MBC_{90}$ (µM) | | | | | |
|---|---|---|---|---|---|---|---|---|---|---|---|---|
| CMPD | E | S | K | A | P | E | E | S | K | A | P | E |
| 1 | 1.63 | 1.63 | 1.63 | 1.63 | 1.63 | 1.63 | 1.87 | 3.09 | 2.36 | 3.05 | 4.01 | 3.14 |
| 2 | 1.52 | 1.52 | 1.52 | 1.52 | 1.52 | 1.52 | 1.66 | 2.03 | 3.98 | 2.83 | 2.32 | 4.15 |
| 7 | 1.52 | 1.52 | 1.52 | 1.52 | 1.52 | 1.52 | 3.27 | 3.28 | 2.16 | 3.23 | 13.74 | 6.36 |
| 16 | 1.62 | 1.62 | 1.62 | 1.62 | 1.62 | 1.62 | 2.87 | 3.88 | 4.45 | 2.77 | 3.99 | 9.55 |
| 19 | 1.66 | 1.66 | 1.66 | 1.66 | 1.66 | 1.66 | 3.59 | 2.88 | 2.61 | 4.66 | 2.77 | 2.70 |

| | $MBEC_{50}$ (µM) | | | | | | $IC_{50}$ (µM) | AI |
|---|---|---|---|---|---|---|---|---|
| CMPD | E | S | K | A | P | E | A549 | — |
| 1 | 38.84 | 13.87 | 6.97 | 14.82 | 19.68 | 13.02 | 163.6 | 100.0 |
| 2 | 29.20 | 2.18 | 4.65 | 15.84 | 30.62 | 13.44 | 124.6 | 81.8 |
| 7 | 26.30 | 4.35 | 4.81 | 13.10 | 45.56 | 14.54 | 65.7 | 43.1 |
| 16 | 28.08 | 7.58 | 6.28 | 14.13 | 34.44 | 12.68 | >225 | >139 |
| 19 | 13.27 | 6.40 | 8.60 | 24.07 | 5.01 | 15.14 | 145.7 | 87.6 |

TABLE 2

Physicochemical properties of individual bis-cyclic guanidines. Shown are data for the active set (1-27), inactive set (28-54), and front-runner compounds (lead 5; 1, 2, 7, 16, and 19). Molecular Weight (MW), number of rotatable bonds (RB), number of hydrogen bond acceptors (HBA) and donors (HBD), polar surface area (PSA).

| Set | MW | AlogP | RB | HBA | HBD | PSA |
|---|---|---|---|---|---|---|
| 1-27 | 618.24 ± 50.99 | 8.72 ± 0.66 | 16.33 ± 1.27 | 2 ± 0 | 2 ± 0 | 69.45 ± 0 |
| 28-54 | 421.32 ± 55.46 | 4.78 ± 1.35 | 11.67 ± 2.59 | 2 ± 0 | 2 ± 0 | 72.38 ± 4.22 |
| Lead 5 | 566.03 ± 23.33 | 8.00 ± 0.62 | 17.40 ± 0.55 | 2 ± 0 | 2 ± 0 | 69.45 ± 0 |

Supplemental TABLE S1

Chemical composition of the synthetic scaffold ranking library.

| ID | # of samples | Total # | Structure of Core Scaffold | E | S | K | A | P | E |
|---|---|---|---|---|---|---|---|---|---|
| 2157 | 110 | 45,864 | (structure) | 20 | 20 | 0 | 20 | 10 | 20 |
| 1955 | 120 | 738,192 | (structure) | 1 | 20 | 0 | 10 | 0 | 1 |

Supplemental TABLE S1-continued

Chemical composition of the synthetic scaffold ranking library.

| ID | # of samples | Total # | Structure of Core Scaffold | E | S | K | A | P | E |
|---|---|---|---|---|---|---|---|---|---|
| 2160 | 110 | 45,864 | | 1 | 20 | 0 | 10 | 0 | 1 |
| 1319 | 116 | 56,610 | | 4 | 20 | 0 | 4 | 0 | 0 |
| 1276 | 116 | 56,610 | | 4 | 20 | 0 | 2 | 0 | 0 |
| 1954 | 120 | 738,192 | | 4 | 10 | 0 | 10 | 0 | 1 |
| 2161 | 110 | 45,864 | | 1 | 10 | 2 | 2 | 1 | 2 |
| 1275 | 116 | 56,610 | | 2 | 10 | 0 | 4 | 0 | 0 |
| 1666 | 96 | 31,320 | | 1 | 10 | 0 | 4 | 0 | 0 |

Supplemental TABLE S1-continued

Chemical composition of the synthetic scaffold ranking library.

| ID | # of samples | Total # | Structure of Core Scaffold | E | S | K | A | P | E |
|---|---|---|---|---|---|---|---|---|---|
| 1952 | 120 | 738,192 | | 1 | 10 | 1 | 2 | 1 | 1 |
| 882 | 125 | 72,283 | | 0 | 10 | 0 | 0 | 0 | 0 |
| 2159 | 110 | 45,864 | | 2 | 4 | 0 | 4 | 0 | 0 |
| 1324 | 116 | 56,610 | | 1 | 4 | 0 | 1 | 0 | 0 |
| 2048 | 83 | 17,340 | | 1 | 4 | 0 | 1 | 0 | 0 |
| 1456 | 174 | 195,112 | | 0 | 4 | 0 | 1 | 0 | 0 |
| 2123 | 142 | 102,459 | | 0 | 4 | 0 | 1 | 0 | 0 |

Supplemental TABLE S1-continued
Chemical composition of the synthetic scaffold ranking library.
| ID | # of samples | Total # | Structure of Core Scaffold | E | S | K | A | P | E |
|---|---|---|---|---|---|---|---|---|---|
| 1509 | 319 | 13,398 | 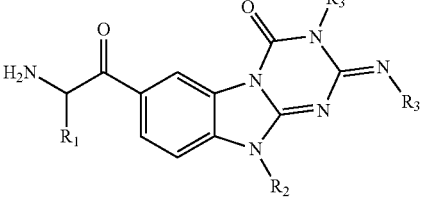 | 0 | 4 | 0 | 0 | 0 | 0 |
| 2049 | 83 | 17,340 | 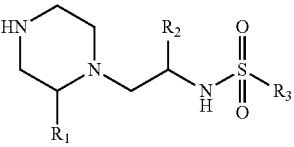 | 0 | 4 | 0 | 0 | 0 | 0 |
| 1664 | 96 | 31,320 | 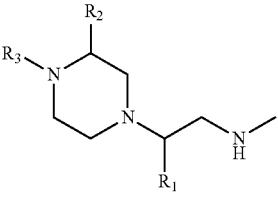 | 1 | 2 | 0 | 1 | 0 | 0 |
| 1665 | 96 | 31,320 | 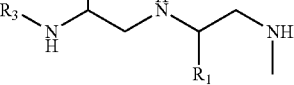 | 1 | 2 | 0 | 0 | 0 | 0 |
| 1956 | 120 | 738,192 | 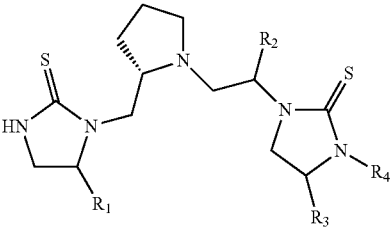 | 0 | 4 | 0 | 1 | 0 | 0 |
| 1662 | 96 | 31,320 | 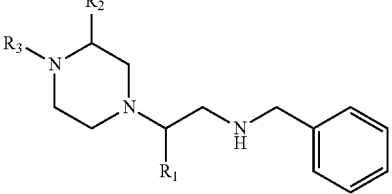 | 0 | 2 | 0 | 0 | 0 | 0 |
| 2158 | 110 | 45,864 | 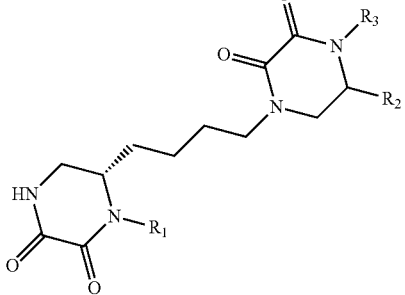 | 0 | 2 | 0 | 0 | 0 | 0 |

Supplemental TABLE S1-continued

Chemical composition of the synthetic scaffold ranking library.

| ID | # of samples | Total # | Structure of Core Scaffold | E | S | K | A | P | E |
|---|---|---|---|---|---|---|---|---|---|
| 2057 | 94 | 3,249 | | 1 | 1 | 0 | 0 | 0 | 0 |
| 1295 | 107 | 45,288 | | 0 | 1 | 0 | 0 | 0 | 0 |
| 2135 | 150 | 125,000 | | 0 | 0 | 0 | 1 | 0 | 0 |
| 1953 | 120 | 738,192 | | 0 | 0 | 0 | 0 | 0 | 0 |
| 1661 | 96 | 31,320 | | 0 | 0 | 0 | 0 | 0 | 0 |
| 1481 | 135 | 85,428 | | 0 | 0 | 0 | 0 | 0 | 0 |

Supplemental TABLE S1-continued

Chemical composition of the synthetic scaffold ranking library.

| ID | # of samples | Total # | Structure of Core Scaffold | E | S | K | A | P | E |
|----|----|----|----|---|---|---|---|---|---|
| 1277 | 400 | 16,400 | | 0 | 0 | 0 | 0 | 0 | 0 |
| 1387 | 400 | 16,000 | | 0 | 0 | 0 | 0 | 0 | 0 |
| 1409 | 400 | 10,800 | | 0 | 0 | 0 | 0 | 0 | 0 |
| 1978 | 128 | 38,250 | | 0 | 0 | 0 | 0 | 0 | 0 |
| 2017 | 156 | 134,560 | | 0 | 0 | 0 | 0 | 0 | 0 |
| 2103 | 127 | 3,990 | | 0 | 0 | 0 | 0 | 0 | 0 |

Supplemental TABLE S1-continued

Chemical composition of the synthetic scaffold ranking library.

| ID | # of samples | Total # | Structure of Core Scaffold | E | S | K | A | P | E |
|---|---|---|---|---|---|---|---|---|---|
| 2165 | 125 | 3,876 | (structure) | 0 | 0 | 0 | 0 | 0 | 0 |
| 2058 | 94 | 3,249 | (structure) | 0 | 0 | 0 | 0 | 0 | 0 |

"ID" corresponds to the numbers used in FIG. 1 and throughout the manuscript.
"# of samples" is the number of samples comprised in corresponding positional scanning library for a given scaffold.
"Total #" is the total number of compounds in a given scaffold ranking sample.
"ESKAPE" are the antimicrobial activity values used to generate the stacked scored bars in FIG. 1, score of 20 = 5 μM activity, 10 = 10 μM, 4 = 25 μM, 2 = 50 μM, 1 = 100 μM, 0 = no activity at any dose tested.
The table is presented in the same order as FIG. 1 in the manuscript; scaffolds that showed no activity against any of the pathogens were not included in FIG. 1.

Supplemental TABLE S2

Deconvolving the 2157 library.

| Sample # | Incorporated Functionality | R1 | R2 | R3 |
|---|---|---|---|---|
| 2157.001 | (H) | hydrogen | X | X |
| 2157.002 | (structure) | 2-phenylbutyl | X | X |
| 2157.003 | (structure) | 3-phenylbutyl | X | X |
| 2157.004 | (structure) | m-tolylethyl | X | X |

Supplemental TABLE S2-continued
| | Deconvolving the 2157 library. | | | |
|---|---|---|---|---|
| Sample # | Incorporated Functionality | R1 | R2 | R3 |
| 2157.005 | 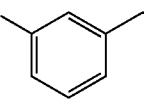 | 2-(3-fluoro-phenyl)-ethyl | X | X |
| 2157.006 | 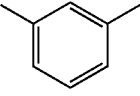 | 2-(3-bromo-phenyl)-ethyl | X | X |
| 2157.007 | 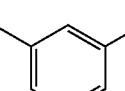 | 2-(3-trifluoromethyl-phenyl)-ethyl | X | X |
| 2157.008 | 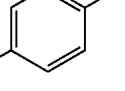 | p-tolylethyl | X | X |
| 2157.009 | 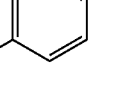 | 2-(4-fluoro-phenyl)-ethyl | X | X |
| 2157.010 | 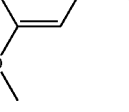 | 2-(3-methoxy-phenyl)-ethyl | X | X |
| 2157.011 | 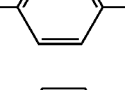 | 2-(4-bromo-phenyl)-ethyl | X | X |
| 2157.012 | 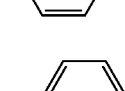 | 2-(4-methoxy-phenyl)-ethyl | X | X |
| 2157.013 | 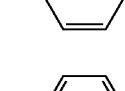 | 2-(4-ethoxy-phenyl)-ethyl | X | X |
| 2157.014 | 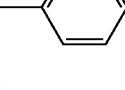 | 2-(4-isobutyl-phenyl)-propyl | X | X |
| 2157.015 | 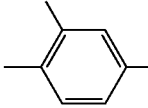 | 3,4-dichlorophenethyl | X | X |

Supplemental TABLE S2-continued
Deconvolving the 2157 library.
| Sample # | Incorporated Functionality | R1 | R2 | R3 |
|---|---|---|---|---|
| 2157.016 | 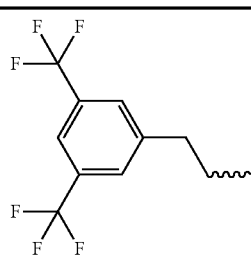 | 2-(3,5-bis-trifluoromethyl-phenyl)-ethyl | X | X |
| 2157.017 | 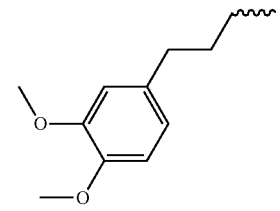 | 3-(3,4-dimethoxy-phenyl)-propyl | X | X |
| 2157.018 | 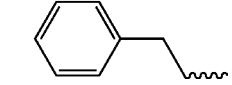 | phenethyl | X | X |
| 2157.019 | 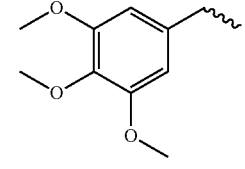 | 3,4,5-trimethoxy-benzyl | X | X |
| 2157.020 | 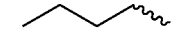 | butyl | X | X |
| 2157.021 |  | heptyl | X | X |
| 2157.022 | 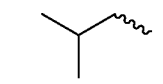 | isobutyl | X | X |
| 2157.023 | 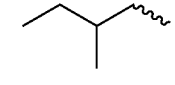 | 2-methylbutyl | X | X |
| 2157.024 | 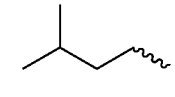 | 3-methylbutyl | X | X |
| 2157.025 | 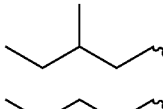 | 3-methylpentyl | X | X |
| 2157.026 | 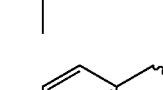 | 4-methylpentyl | X | X |
| 2157.027 | 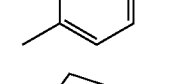 | 4-methyl-benzyl | X | X |
| 2157.028 | 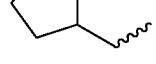 | cyclopentyl-methyl | X | X |

Supplemental TABLE S2-continued

Deconvolving the 2157 library.

| Sample # | Incorporated Functionality | R1 | R2 | R3 |
|---|---|---|---|---|
| 2157.029 | 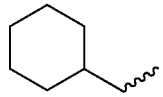 | cyclohexyl-methyl | X | X |
| 2157.030 | 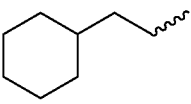 | cyclohexyl-ethyl | X | X |
| 2157.031 | 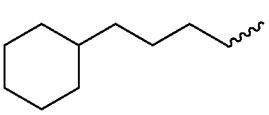 | cyclohexyl-butyl | X | X |
| 2157.032 | 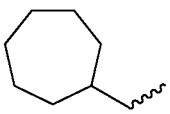 | cycloheptyl-methyl | X | X |
| 2157.033 | 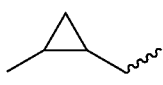 | 2-methylcyclopropyl-methyl | X | X |
| 2157.034 | 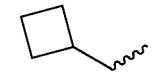 | cyclobutyl-methyl | X | X |
| 2157.035 | 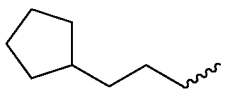 | 3-cyclopentyl-propyl | X | X |
| 2157.036 | 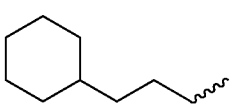 | cyclohexyl-propyl | X | X |
| 2157.037 | 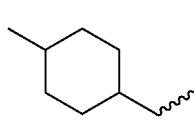 | 4-methyl-1-cyclohexyl-methyl | X | X |
| 2157.038 | 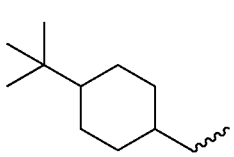 | 4-tert-butyl-cyclohexyl-methyl | X | X |
| 2157.039 | 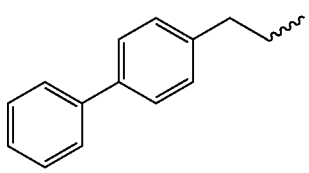 | 2-Biphenyl-4-yl-ethyl | X | X |
| 2157.040 | 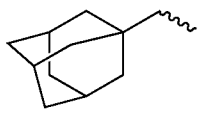 | adamantan-1-yl-methyl | X | X |
| 2157.041 | 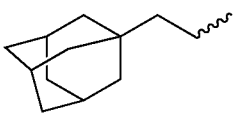 | adamantan-1-yl-ethyl | X | X |

Supplemental TABLE S2-continued

Deconvolving the 2157 library.

| Sample # | Incorporated Functionality | R1 | R2 | R3 |
|---|---|---|---|---|
| 2157.042 | (2-bicyclo[2.2.1]hept-2-yl-ethyl group) | 2-Bicyclo[2.2.1]hept-2-yl-ethyl | X | X |
| 2157.043 | (S-methyl) | X | S-methyl | X |
| 2157.044 | (S-benzyl) | X | S-benzyl | X |
| 2157.045 | (H) | X | hydrogen | X |
| 2157.046 | (S-2-butyl) | X | S-2-butyl | X |
| 2157.047 | (S-isobutyl) | X | S-isobutyl | X |
| 2157.048 | (R-hydroxymethyl) | X | R-hydroxymethyl | X |
| 2157.049 | ((R,R)-1-hydroxyethyl) | X | (R,R)-1-hydroxyethyl | X |
| 2157.050 | (S-isopropyl) | X | S-isopropyl | X |
| 2157.051 | (S-4-hydroxybenzyl) | X | S-4-hydroxybenzyl | X |
| 2157.052 | (R-methyl) | X | R-methyl | X |
| 2157.053 | (R-benzyl) | X | R-benzyl | X |
| 2157.054 | (R-2-butyl) | X | R-2-butyl | X |
| 2157.055 | (R-isobutyl) | X | R-isobutyl | X |
| 2157.056 | (S-hydroxymethyl) | X | S-hydroxymethyl | X |
| 2157.057 | ((S,S)-1-hydroxyethyl) | X | (S,S)-1-hydroxyethyl | X |

Supplemental TABLE S2-continued

Deconvolving the 2157 library.

| Sample # | Incorporated Functionality | R1 | R2 | R3 |
|---|---|---|---|---|
| 2157.058 | (isobutyl) | X | R-isopropyl | X |
| 2157.059 | (4-hydroxybenzyl) | X | R-4-hydroxybenzyl | X |
| 2157.060 | (benzyl) | X | S-phenyl | X |
| 2157.061 | (S-propyl) | X | S-propyl | X |
| 2157.062 | (R-propyl) | X | R-propyl | X |
| 2157.063 | (S-butyl) | X | S-butyl | X |
| 2157.064 | (R-butyl) | X | R-butyl | X |
| 2157.065 | (S-2-naphthylmethyl) | X | S-2-naphthylmethyl | X |
| 2157.066 | (R-2-naphthylmethyl) | X | R-2-naphthylmethyl | X |
| 2157.067 | (S-cyclohexylmethyl) | X | S-cyclohexylmethyl | X |
| 2157.068 | (R-cyclohexylmethyl) | X | R-cyclohexylmethyl | X |
| 2157.069 | H | X | X | hydrogen |
| 2157.070 | (2-phenylbutyl) | X | X | 2-phenylbutyl |

Supplemental TABLE S2-continued

Deconvolving the 2157 library.

| Sample # | Incorporated Functionality | R1 | R2 | R3 |
|---|---|---|---|---|
| 2157.071 | (3-phenylbutyl group structure) | X | X | 3-phenylbbutyl |
| 2157.072 | (m-tolylethyl structure) | X | X | m-tolylethyl |
| 2157.073 | (3-fluorophenylethyl structure) | X | X | 2-(3-fluoro-phenyl)-ethyl |
| 2157.074 | (3-bromophenylethyl structure) | X | X | 2-(3-bromo-phenyl)-ethyl |
| 2157.075 | (3-trifluoromethylphenylethyl structure) | X | X | 2-(3-trifluoromethyl-phenyl)-ethyl |
| 2157.076 | (p-tolylmethyl structure) | X | X | p-tolylmethyl |
| 2157.077 | (4-fluorophenylethyl structure) | X | X | 2-(4-fluoro-phenyl)-ethyl |
| 2157.078 | (3-methoxyphenylethyl structure) | X | X | 2-(3-methoxy-phenyl)-ethyl |
| 2157.079 | (4-bromophenylethyl structure) | X | X | 2-(4-bromo-phenyl)-ethyl |
| 2157.080 | (4-methoxyphenylethyl structure) | X | X | 2-(4-methoxy-phenyl)-ethyl |
| 2157.081 | (4-ethoxyphenylethyl structure) | X | X | 2-(4-ethoxy-phenyl)-ethyl |
| 2157.082 | (4-isobutylphenylpropyl structure) | X | X | 2-(4-isobutyl-phenyl)-propyl |

Supplemental TABLE S2-continued

| | Deconvolving the 2157 library. | | | |
|---|---|---|---|---|
| Sample # | Incorporated Functionality | R1 | R2 | R3 |
| 2157.083 | 3,4-dichlorophenyl group | X | X | 3,4-dichlorophenethyl |
| 2157.084 | 3,5-bis(trifluoromethyl)phenyl group | X | X | 2-(3,5-bis-trifluoromeethyl-phenyl)-ethyl |
| 2157.085 | 3,4-dimethoxyphenylpropyl group | X | X | 3-(3,4-dimethoxy-phenyl)-propyl |
| 2157.086 | phenethyl group | X | X | phenethyl |
| 2157.087 | 3,4,5-trimethoxybenzyl group | X | X | 3,4,5-trimethoxy-benzyl |
| 2157.088 | butyl chain | X | X | butyl |
| 2157.089 | heptyl chain | X | X | heptyl |
| 2157.090 | isobutyl group | X | X | isobutyl |
| 2157.091 | 2-methylbutyl group | X | X | 2-methylbutyl |
| 2157.092 | 3-methylbutyl group | X | X | 3-methylbutyl |
| 2157.093 | 3-methylpentyl group | X | X | 3-methylpentyl |
| 2157.094 | 4-methylpentyl group | X | X | 4-methylpentyl |

Supplemental TABLE S2-continued

Deconvolving the 2157 library.

| Sample # | Incorporated Functionality | R1 | R2 | R3 |
|---|---|---|---|---|
| 2157.095 | 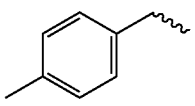 | X | X | 4-methyl-benzyl |
| 2157.096 | 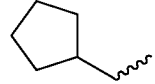 | X | X | cyclopently-methyl |
| 2157.097 | 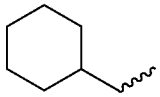 | X | X | cyclohexyl-methyl |
| 2157.098 | 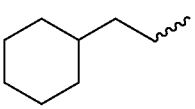 | X | X | cyclohexyl-ethyl |
| 2157.099 | 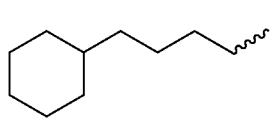 | X | X | cyclohexyl-butyl |
| 2157.100 | 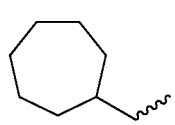 | X | X | cycloheptyl-methyl |
| 2157.101 | 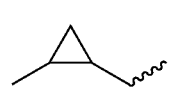 | X | X | 2-methylcyclopropyl-methyl |
| 2157.102 |  | X | X | cyclobutyl-methyl |
| 2157.103 | 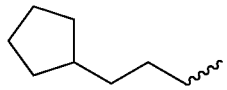 | X | X | 3-cyclopentyl-propyl |
| 2157.104 | 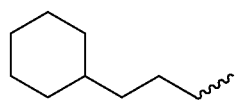 | X | X | cyclohexyl-propyl |
| 2157.105 | 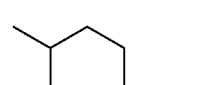 | X | X | 4-methyl-1-cyclohexyl-methyl |
| 2157.106 | 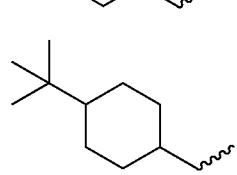 | X | X | 4-tert-butyl-cyclohexyl-methyl |
| 2157.107 | 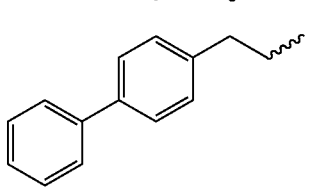 | X | X | 2-Biphenyl-4-yl-ethyl |

Supplemental TABLE S2-continued

Deconvolving the 2157 library.

| Sample # | Incorporated Functionality | R1 | R2 | R3 |
|---|---|---|---|---|
| 2157.108 | (adamantyl-methyl structure) | X | X | adamantan-1-yl-methyl |
| 2157.109 | (adamantyl-ethyl structure) | X | X | adamantan-1-yl-ethyl |
| 2157.110 | (norbornyl-ethyl structure) | X | X | 2-Bicyclo[2.2.1]hept-2-yl-ethyl |

The 2157 scaffold ranking mixture was systematically synthesized into a positional scanning library containing 110 samples that were fixed at either the $R_1$ (42 samples), $R_2$ (26 samples) or $R_3$ (42 samples) positions.

SUPPLEMETAL TABLE S4a

Chemical composition of individually synthesized bis-cyclic guanidines. Shown are the functional groups attached at each diversity position on the individual bis-cyclic guanidines, the molecular formulas, the physicochemical properties, the MS (ESI) m/z [M + H]+ "MW found," the retention time in minutes "RT min," and the stacked score "Total" for each compound. (Supplemental Table S4b shows the details on the stacked scores and Table S4c shows the full structure for all 54 compounds). The RT min was determined from analyzing the 214 nm spectrum of compounds run under conditions described in the section "LCMS analysis of crude material" in the Materials and Methods. All samples showed purity >80% by LCMS (214 nM).

| ID | R1 | R2 | R3 | Molecular Formula | MW | MH+ found | RT min. | AlogP | HBA | HBD | RB | PSA | Total |
|---|---|---|---|---|---|---|---|---|---|---|---|---|---|
| 1 | 2-(3-trifluoromethyl-phenyl)-ethyl | S-butyl | heptyl | $C_{30}H_{49}F_3N_6$ | 550.75 | 551.20 | 4.458 | 7.41 | 2 | 2 | 18 | 69.45 | 163 |
| 2 | 2-(3-trifluoromethyl-phenyl)-ethyl | S-butyl | cyclohexyl-butyl | $C_{33}H_{53}F_3N_6$ | 590.81 | 591.45 | 4.582 | 8.20 | 2 | 2 | 17 | 69.45 | 173 |
| 3 | 2-(3-trifluoromethyl-phenyl)-ethyl | S-butyl | 2-Biphenyl-4-yl-ethyl | $C_{37}H_{47}F_3N_6$ | 632.80 | 633.30 | 4.512 | 8.13 | 2 | 2 | 16 | 69.45 | 148 |
| 4 | 2-(3-trifluoromethyl-phenyl)-ethyl | R-2-naphthylmethyl | heptyl | $C_{37}H_{49}F_3N_6$ | 634.82 | 635.30 | 4.557 | 8.44 | 2 | 2 | 17 | 69.45 | 127 |
| 5 | 2-(3-trifluoromethyl-phenyl)-ethyl | R-2-naphthylmethyl | cyclohexyl-butyl | $C_{40}H_{53}F_3N_6$ | 674.88 | 675.30 | 4.721 | 9.23 | 2 | 2 | 16 | 69.45 | 109 |
| 6 | 2-(3-trifluoromethyl-phenyl)-ethyl | R-2-naphthylmethyl | 2-Biphenyl-4-yl-ethyl | $C_{44}H_{47}F_3N_6$ | 716.88 | 717.30 | 4.597 | 9.16 | 2 | 2 | 15 | 69.45 | 94 |
| 7 | 2-(3-trifluoromethyl-phenyl)-ethyl | S-cyclohexylmethyl | heptyl | $C_{33}H_{53}F_3N_6$ | 590.81 | 591.35 | 4.632 | 8.20 | 2 | 2 | 17 | 69.45 | 156 |
| 8 | 2-(3-trifluoromethyl-phenyl)-ethyl | S-cyclohexylmethyl | cyclohexyl-butyl | $C_{36}H_{57}F_3N_6$ | 630.87 | 631.40 | 4.813 | 8.99 | 2 | 2 | 16 | 69.45 | 115 |
| 9 | 2-(3-trifluoromethyl-phenyl)-ethyl | S-cyclohexylmethyl | 2-Biphenyl-4-yl-ethyl | $C_{40}H_{51}F_3N_6$ | 672.87 | 673.25 | 4.651 | 8.93 | 2 | 2 | 15 | 69.45 | 130 |
| 10 | cyclohexyl-butyl | S-butyl | heptyl | $C_{31}H_{60}N_6$ | 516.85 | 517.35 | 4.647 | 8.05 | 2 | 2 | 19 | 69.45 | 140 |
| 11 | cyclohexyl-butyl | S-butyl | cyclohexyl-butyl | $C_{34}H_{64}N_6$ | 556.91 | 557.35 | 4.832 | 8.84 | 2 | 2 | 18 | 69.45 | 155 |
| 12 | cyclohexyl-butyl | S-butyl | 2-Biphenyl-4-yl-ethyl | $C_{38}H_{58}N_6$ | 598.91 | 599.40 | 4.629 | 8.78 | 2 | 2 | 17 | 69.45 | 107.5 |
| 13 | cyclohexyl-butyl | R-2-naphthylmethyl | heptyl | $C_{38}H_{60}N_6$ | 600.92 | 601.40 | 4.759 | 9.08 | 2 | 2 | 18 | 69.45 | 125 |
| 14 | cyclohexyl-butyl | R-2-naphthylmethyl | cyclohexyl-butyl | $C_{41}H_{64}N_6$ | 640.99 | 641.45 | 4.898 | 9.87 | 2 | 2 | 17 | 69.45 | 94 |
| 15 | cyclohexyl-butyl | R-2-naphthylmethyl | 2-Biphenyl-4-yl-ethyl | $C_{45}H_{58}N_6$ | 682.98 | 683.40 | 4.747 | 9.80 | 2 | 2 | 16 | 69.45 | 68 |
| 16 | cyclohexyl-butyl | S-cyclohexylmethyl | heptyl | $C_{34}H_{64}N_6$ | 556.91 | 557.35 | 4.841 | 8.84 | 2 | 2 | 18 | 69.45 | 151 |
| 17 | cyclohexyl-butyl | S-cyclohexylmethyl | cyclohexyl-butyl | $C_{37}H_{68}N_6$ | 596.98 | 597.40 | 5.028 | 9.64 | 2 | 2 | 17 | 69.45 | 120 |
| 18 | cyclohexyl-butyl | S-cyclohexylmethyl | 2-Biphenyl-4-yl-ethyl | $C_{41}H_{62}N_6$ | 638.97 | 639.40 | 4.832 | 9.57 | 2 | 2 | 16 | 69.45 | 120 |
| 19 | adamantan-1-yl-ethyl | S-butyl | heptyl | $C_{33}H_{60}N_6$ | 540.87 | 541.30 | 4.644 | 7.36 | 2 | 2 | 17 | 69.45 | 156 |
| 20 | adamantan-1-yl-ethyl | S-butyl | cyclohexyl-butyl | $C_{36}H_{64}N_6$ | 580.93 | 581.45 | 4.797 | 8.15 | 2 | 2 | 16 | 69.45 | 160 |
| 21 | adamantan-1-yl-ethyl | S-butyl | 2-Biphenyl-4-yl-ethyl | $C_{40}H_{58}N_6$ | 622.93 | 623.40 | 4.649 | 8.08 | 2 | 2 | 15 | 69.45 | 123 |

SUPPLEMETAL TABLE S4a-continued

Chemical composition of individually synthesized bis-cyclic guanidines. Shown are the functional groups attached at each diversity position on the individual bis-cyclic guanidines, the molecular formulas, the physicochemical properties, the MS (ESI) m/z [M + H]+ "MW found," the retention time in minutes "RT min," and the stacked score "Total" for each compound. (Supplemental Table S4b shows the details on the stacked scores and Table S4c shows the full structure for all 54 compounds). The RT min was determined from analyzing the 214 nm spectrum of compounds run under conditions described in the section "LCMS analysis of crude material" in the Materials and Methods. All samples showed purity >80% by LCMS (214 nM).

| ID | R1 | R2 | R3 | Molecular Formula | MW | MH+ found | RT min. | AlogP | HBA | HBD | RB | PSA | Total |
|---|---|---|---|---|---|---|---|---|---|---|---|---|---|
| 22 | adamantan-1-yl-ethyl | R-2-naphthylmethyl | heptyl | $C_{40}H_{60}N_6$ | 624.94 | 625.40 | 4.717 | 8.38 | 2 | 2 | 16 | 69.45 | 135 |
| 23 | adamantan-1-yl-ethyl | R-2-naphthylmethyl | cyclohexyl-butyl | $C_{43}H_{64}N_6$ | 665.01 | 665.45 | 4.898 | 9.18 | 2 | 2 | 15 | 69.45 | 29 |
| 24 | adamantan-1-yl-ethyl | R-2-naphthylmethyl | 2-Biphenyl-4-yl-ethyl | $C_{47}H_{58}N_6$ | 707.00 | 707.40 | 4.747 | 9.11 | 2 | 2 | 14 | 69.45 | 14 |
| 25 | adamantan-1-yl-ethyl | S-cyclohexylmethyl | heptyl | $C_{36}H_{64}N_6$ | 580.93 | 581.40 | 4.810 | 8.15 | 2 | 2 | 16 | 69.45 | 160 |
| 26 | adamantan-1-yl-ethyl | S-cyclohexylmethyl | cyclohexyl-butyl | $C_{39}H_{68}N_6$ | 621.00 | 621.45 | 5.002 | 8.94 | 2 | 2 | 15 | 69.45 | 120 |
| 27 | adamantan-1-yl-ethyl | S-cyclohexylmethyl | 2-Biphenyl-4-yl-ethyl | $C_{43}H_{62}N_6$ | 662.99 | 663.45 | 4.791 | 8.87 | 2 | 2 | 14 | 69.45 | 84 |
| 28 | heptyl | hydrogen | hydrogen | $C_{17}H_{34}N_6$ | 322.49 | 323.05 | 3.450 | 2.54 | 2 | 2 | 11 | 78.24 | 0 |
| 29 | heptyl | hydrogen | m-tolylethyl | $C_{26}H_{44}N_6$ | 440.67 | 441.15 | 4.008 | 5.14 | 2 | 2 | 14 | 69.45 | 4 |
| 30 | heptyl | hydrogen | 2-methylbutyl | $C_{22}H_{44}N_6$ | 392.63 | 393.10 | 3.956 | 4.39 | 2 | 2 | 14 | 69.45 | 0 |
| 31 | heptyl | S-2-butyl | hydrogen | $C_{21}H_{42}N_6$ | 378.60 | 379.10 | 3.884 | 4.22 | 2 | 2 | 13 | 78.24 | 4 |
| 32 | heptyl | S-2-butyl | m-tolylethyl | $C_{30}H_{52}N_6$ | 496.77 | 497.25 | 4.299 | 6.81 | 2 | 2 | 16 | 69.45 | 51 |
| 33 | heptyl | S-2-butyl | 2-methylbutyl | $C_{26}H_{52}N_6$ | 448.73 | 449.25 | 4.211 | 6.07 | 2 | 2 | 16 | 69.45 | 4 |
| 34 | heptyl | R-propyl | hydrogen | $C_{20}H_{40}N_6$ | 364.57 | 365.10 | 3.801 | 3.90 | 2 | 2 | 13 | 78.24 | 4 |
| 35 | heptyl | R-propyl | m-tolylethyl | $C_{29}H_{50}N_6$ | 482.75 | 483.20 | 4.256 | 6.50 | 2 | 2 | 16 | 69.45 | 22 |
| 36 | heptyl | R-propyl | 2-methylbutyl | $C_{25}H_{50}N_6$ | 434.70 | 435.20 | 4.158 | 5.75 | 2 | 2 | 16 | 69.45 | 4 |
| 37 | cyclohexyl-methyl | hydrogen | hydrogen | $C_{17}H_{32}N_6$ | 320.48 | 321.05 | 3.195 | 2.03 | 2 | 2 | 7 | 78.24 | 0 |
| 38 | cyclohexyl-methyl | hydrogen | m-tolylethyl | $C_{26}H_{42}N_6$ | 438.65 | 439.15 | 3.848 | 4.63 | 2 | 2 | 10 | 69.45 | 4 |
| 39 | cyclohexyl-methyl | hydrogen | 2-methylbutyl | $C_{22}H_{42}N_6$ | 390.61 | 391.10 | 3.688 | 3.89 | 2 | 2 | 10 | 69.45 | 0 |
| 40 | cyclohexyl-methyl | S-2-butyl | hydrogen | $C_{21}H_{40}N_6$ | 376.58 | 377.10 | 3.687 | 3.71 | 2 | 2 | 9 | 78.24 | 0 |
| 41 | cyclohexyl-methyl | S-2-butyl | m-tolylethyl | $C_{30}H_{50}N_6$ | 494.76 | 495.20 | 4.182 | 6.31 | 2 | 2 | 12 | 69.45 | 4 |
| 42 | cyclohexyl-methyl | S-2-butyl | 2-methylbutyl | $C_{26}H_{50}N_6$ | 446.72 | 447.25 | 4.080 | 5.56 | 2 | 2 | 12 | 69.45 | 4 |
| 43 | cyclohexyl-methyl | R-propyl | hydrogen | $C_{20}H_{38}N_6$ | 362.56 | 363.05 | 3.584 | 3.39 | 2 | 2 | 9 | 78.24 | 0 |
| 44 | cyclohexyl-methyl | R-propyl | m-tolylethyl | $C_{29}H_{48}N_6$ | 480.73 | 481.25 | 4.125 | 5.99 | 2 | 2 | 12 | 69.45 | 4 |
| 45 | cyclohexyl-methyl | R-propyl | 2-methylbutyl | $C_{25}H_{48}N_6$ | 432.69 | 433.20 | 4.006 | 5.24 | 2 | 2 | 12 | 69.45 | 4 |
| 46 | 4-Methyl-1-cyclohexyl-methyl | hydrogen | hydrogen | $C_{18}H_{34}N_6$ | 334.50 | 335.10 | 3.379 | 2.28 | 2 | 2 | 7 | 78.24 | 0 |
| 47 | 4-Methyl-1-cyclohexyl-methyl | hydrogen | m-tolylethyl | $C_{27}H_{44}N_6$ | 452.68 | 453.15 | 3.969 | 4.88 | 2 | 2 | 10 | 69.45 | 4 |
| 48 | 4-Methyl-1-cyclohexyl-methyl | hydrogen | 2-methylbutyl | $C_{23}H_{44}N_6$ | 404.64 | 405.15 | 3.820 | 4.14 | 2 | 2 | 10 | 69.45 | 0 |
| 49 | 4-Methyl-1-cyclohexyl-methyl | S-2-butyl | hydrogen | $C_{22}H_{42}N_6$ | 390.61 | 391.10 | 3.812 | 3.96 | 2 | 2 | 9 | 78.24 | 4 |
| 50 | 4-Methyl-1-cyclohexyl-methyl | S-2-butyl | m-tolylethyl | $C_{31}H_{52}N_6$ | 508.78 | 509.25 | 4.261 | 6.56 | 2 | 2 | 12 | 69.45 | 24 |
| 51 | 4-Methyl-1-cyclohexyl-methyl | S-2-butyl | 2-methylbutyl | $C_{27}H_{52}N_6$ | 460.74 | 461.25 | 4.163 | 5.81 | 2 | 2 | 12 | 69.45 | 4 |
| 52 | 4-Methyl-1-cyclohexyl-methyl | R-propyl | hydrogen | $C_{21}H_{40}N_6$ | 376.58 | 377.10 | 3.730 | 3.64 | 2 | 2 | 9 | 78.24 | 4 |
| 53 | 4-Methyl-1-cyclohexyl-methyl | R-propyl | m-tolylethyl | $C_{30}H_{50}N_6$ | 494.76 | 495.25 | 4.214 | 6.24 | 2 | 2 | 12 | 69.45 | 4 |
| 54 | 4-Methyl-1-cyclohexyl-methyl | R-propyl | 2-methylbutyl | $C_{26}H_{50}N_6$ | 446.72 | 447.20 | 4.112 | 5.50 | 2 | 2 | 12 | 69.45 | 4 |

SUPPLEMENTAL TABLE S4b

MIC data for Individual Compounds. Shown in columns 2 through 7 are the doses where a compound showed activity against a given pathogen. Columns 8 through 13 show the "stacked score" activity, 100/MIC, for each compound against a given pathogen. Column 14 is the total stacked score value used in FIGS. 3 and 5 of the paper. To distinguish E. faecium from E. cloacae in ESKAPE, the latter organism is denoted in red in the above table.

| ID | 25 ug/ml | 10 ug/ml | 5 ug/ml | 4 ug/ml | 3 ug/ml | 2 ug/ml | E | S | K | A | P | E | Total |
|---|---|---|---|---|---|---|---|---|---|---|---|---|---|
| 1 | ESKAPE | ESKAPE | ESKAPE | SK | SK | S | 20 | 50 | 33 | 20 | 20 | 20 | 163 |
| 2 | ESKAPE | ESKAPE | ESKAPE | ESAP | ES | E | 50 | 33 | 20 | 25 | 25 | 20 | 173 |
| 3 | ESKAPE | ESKAPE | ESKAPE | ESKA | S | — | 25 | 33 | 25 | 25 | 20 | 20 | 148 |
| 4 | ESKAPE | ESKAE | ESKAE | ESA | E | — | 33 | 25 | 20 | 25 | 4 | 20 | 127 |
| 5 | ESKAPE | ESKAE | ESKAE | K | — | — | 20 | 20 | 25 | 20 | 4 | 20 | 109 |
| 6 | ESKAPE | ESKAE | SKAE | — | — | — | 10 | 20 | 20 | 20 | 4 | 20 | 94 |
| 7 | ESKAPE | ESKAPE | ESKAPE | ESAP | ES | — | 33 | 33 | 20 | 25 | 25 | 20 | 156 |

SUPPLEMENTAL TABLE S4b-continued

MIC data for Individual Compounds. Shown in columns 2 through 7 are the doses where a compound showed activity against a given pathogen. Columns 8 through 13 show the "stacked score" activity, 100/MIC, for each compound against a given pathogen. Column 14 is the total stacked score value used in FIGS. 3 and 5 of the paper. To distinguish *E. faecium* from *E. cloacae* in ESKAPE, the latter organism is denoted in red in the above table.

| ID | 25 ug/ml | 10 ug/ml | 5 ug/ml | 4 ug/ml | 3 ug/ml | 2 ug/ml | E | S | K | A | P | E | Total |
|---|---|---|---|---|---|---|---|---|---|---|---|---|---|
| 8 | ESKAPE | ESKAPE | EKAPE | P | — | — | 20 | 10 | 20 | 20 | 25 | 20 | 115 |
| 9 | ESKAPE | ESKAPE | ESKAPE | EP | — | — | 25 | 20 | 20 | 20 | 25 | 20 | 130 |
| 10 | ESKAPE | ESKAPE | ESKAPE | ESAP | — | — | 25 | 25 | 20 | 25 | 25 | 20 | 140 |
| 11 | ESKAPE | ESKAPE | ESAPE | EA | E | E | 50 | 20 | 20 | 25 | 20 | 20 | 155 |
| 12 | ESKAPE | ESKAPE | ESKAE | A | — | — | 20 | 20 | 20 | 25 | 2.5 | 20 | 107.5 |
| 13 | ESKAPE | ESKAE | ESKAE | P | — | — | 20 | 20 | 20 | 20 | 25 | 20 | 125 |
| 14 | ESKAPE | ESKAE | SKAE | — | — | — | 10 | 20 | 20 | 20 | 4 | 20 | 94 |
| 15 | ESKAPE | ESKE | SE | — | — | — | 10 | 20 | 10 | 4 | 4 | 20 | 68 |
| 16 | ESKAPE | ESKAPE | ESKAPE | EAP | EA | — | 33 | 20 | 20 | 33 | 25 | 20 | 151 |
| 17 | ESKAPE | ESKAPE | ESKAPE | — | — | — | 20 | 20 | 20 | 20 | 20 | 20 | 120 |
| 18 | ESKAPE | ESKAPE | ESKAPE | — | — | — | 20 | 20 | 20 | 20 | 20 | 20 | 120 |
| 19 | ESKAPE | ESKAPE | ESKAPE | ESAP | ES | — | 33 | 33 | 20 | 25 | 25 | 20 | 156 |
| 20 | ESKAPE | ESKAPE | ESKAPE | EAP | E | E | 50 | 20 | 20 | 25 | 25 | 20 | 160 |
| 21 | ESKAPE | ESKAPE | ESKAPE | EA | E | — | 33 | 20 | 20 | 25 | 5 | 20 | 123 |
| 22 | ESKAPE | ESKAE | ESKAE | EAP | — | — | 25 | 20 | 20 | 25 | 25 | 20 | 135 |
| 23 | ESE | S | S | S | — | — | 4 | 25 | 0 | 0 | 0 | 0 | 29 |
| 24 | ES | S | — | — | — | — | 4 | 10 | 0 | 0 | 0 | 0 | 14 |
| 25 | ESKAPE | ESKAPE | ESKAPE | EAP | E | E | 50 | 20 | 20 | 25 | 25 | 20 | 160 |
| 26 | ESKAPE | ESKAPE | ESKAPE | — | — | — | 20 | 20 | 20 | 20 | 20 | 20 | 120 |
| 27 | ESKAPE | ESKPE | SKP | — | — | — | 10 | 20 | 20 | 4 | 20 | 10 | 84 |
| 28 | — | — | — | — | — | — | 0 | 0 | 0 | 0 | 0 | 0 | 0 |
| 29 | S | — | — | — | — | — | 0 | 4 | 0 | 0 | 0 | 0 | 4 |
| 30 | — | — | — | — | — | — | 0 | 0 | 0 | 0 | 0 | 0 | 0 |
| 31 | S | — | — | — | — | — | 0 | 4 | 0 | 0 | 0 | 0 | 4 |
| 32 | ESAP | ES | S | S | S | — | 10 | 33 | 0 | 4 | 4 | 0 | 51 |
| 33 | S | — | — | — | — | — | 0 | 4 | 0 | 0 | 0 | 0 | 4 |
| 34 | S | — | — | — | — | — | 0 | 4 | 0 | 0 | 0 | 0 | 4 |
| 35 | ESAP | S | — | — | — | — | 4 | 10 | 0 | 4 | 4 | 0 | 22 |
| 36 | S | — | — | — | — | — | 0 | 4 | 0 | 0 | 0 | 0 | 4 |
| 37 | — | — | — | — | — | — | 0 | 0 | 0 | 0 | 0 | 0 | 0 |
| 38 | S | — | — | — | — | — | 0 | 4 | 0 | 0 | 0 | 0 | 4 |
| 39 | — | — | — | — | — | — | 0 | 0 | 0 | 0 | 0 | 0 | 0 |
| 40 | — | — | — | — | — | — | 0 | 0 | 0 | 0 | 0 | 0 | 0 |
| 41 | S | — | — | — | — | — | 0 | 4 | 0 | 0 | 0 | 0 | 4 |
| 42 | S | — | — | — | — | — | 0 | 4 | 0 | 0 | 0 | 0 | 4 |
| 43 | — | — | — | — | — | — | 0 | 0 | 0 | 0 | 0 | 0 | 0 |
| 44 | S | — | — | — | — | — | 0 | 4 | 0 | 0 | 0 | 0 | 4 |
| 45 | S | — | — | — | — | — | 0 | 4 | 0 | 0 | 0 | 0 | 4 |
| 46 | — | — | — | — | — | — | 0 | 0 | 0 | 0 | 0 | 0 | 0 |
| 47 | S | — | — | — | — | — | 0 | 4 | 0 | 0 | 0 | 0 | 4 |
| 48 | — | — | — | — | — | — | 0 | 0 | 0 | 0 | 0 | 0 | 0 |
| 49 | S | — | — | — | — | — | 0 | 4 | 0 | 0 | 0 | 0 | 4 |
| 50 | ESA | ES | — | — | — | — | 10 | 10 | 0 | 4 | 0 | 0 | 24 |
| 51 | S | — | — | — | — | — | 0 | 4 | 0 | 0 | 0 | 0 | 4 |
| 52 | S | — | — | — | — | — | 0 | 4 | 0 | 0 | 0 | 0 | 4 |
| 53 | S | — | — | — | — | — | 0 | 4 | 0 | 0 | 0 | 0 | 4 |
| 54 | S | — | — | — | — | — | 0 | 4 | 0 | 0 | 0 | 0 | 4 |

Supplemental TABLE S4c
Structures of individually synthesized bis-cyclic guanidines.
1
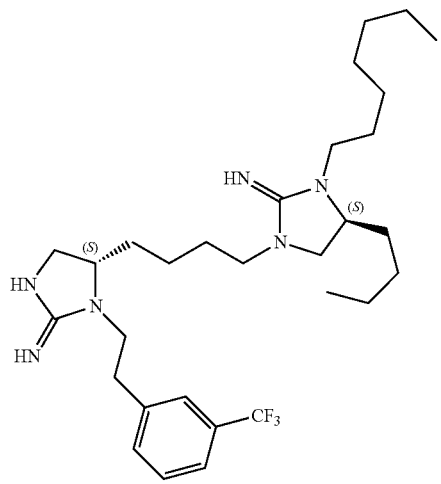
2
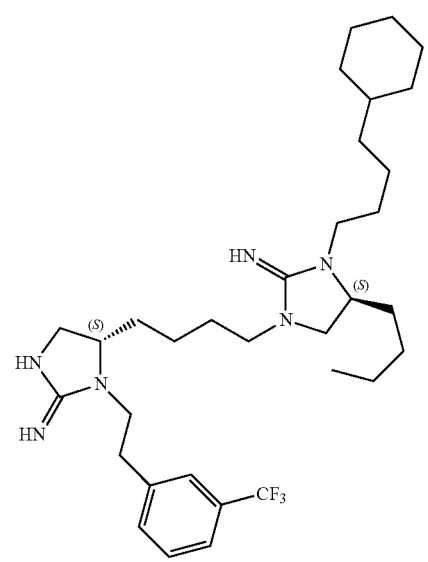
Supplemental TABLE S4c-continued
Structures of individually synthesized bis-cyclic guanidines.
3
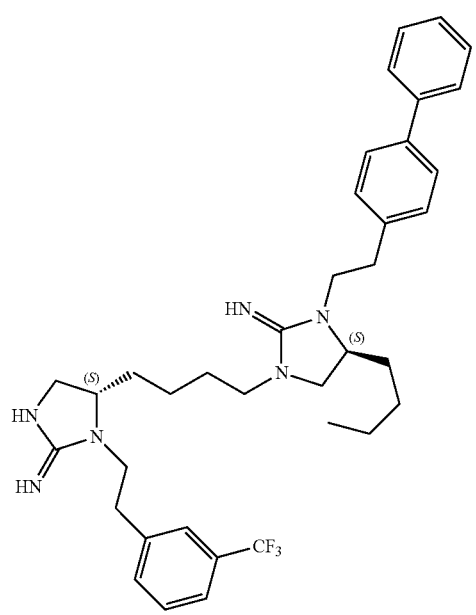
4
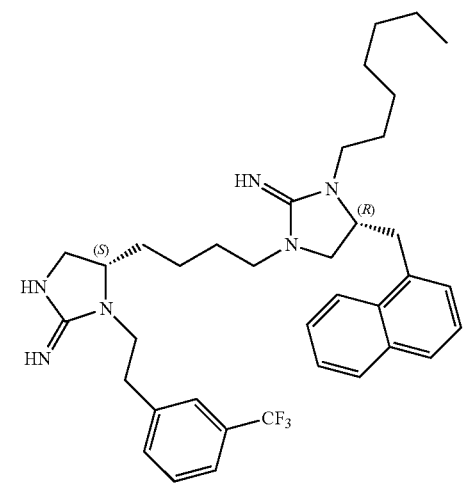

Supplemental TABLE S4c-continued
Structures of individually synthesized bis-cyclic guanidines.
5
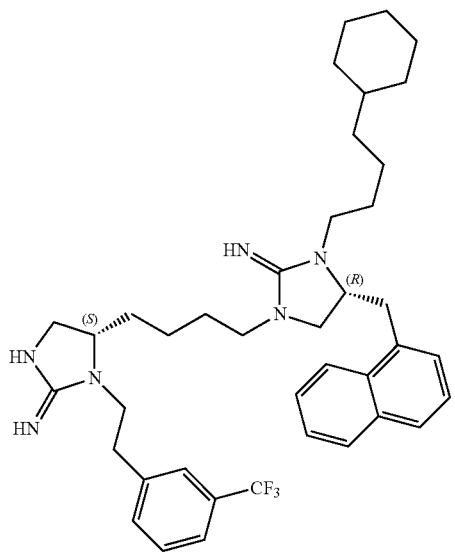
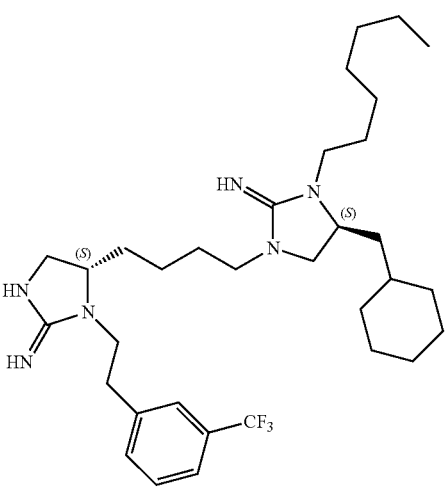
6
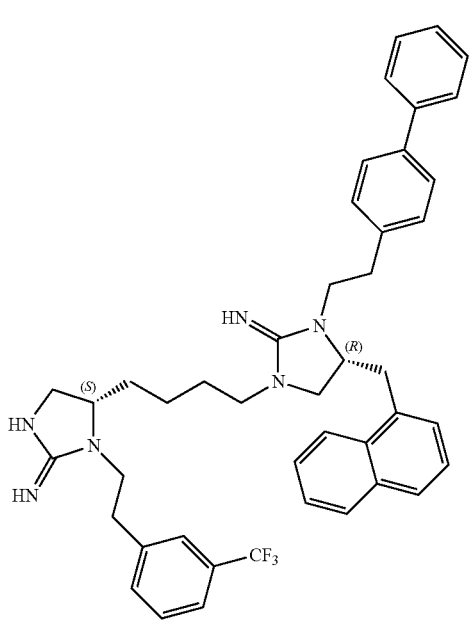
8
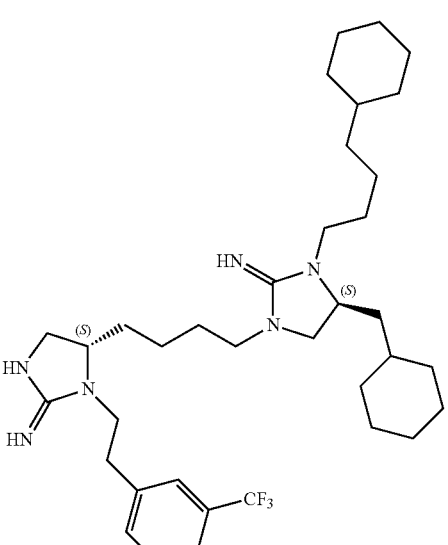

Supplemental TABLE S4c-continued
Structures of individually synthesized bis-cyclic guanidines.
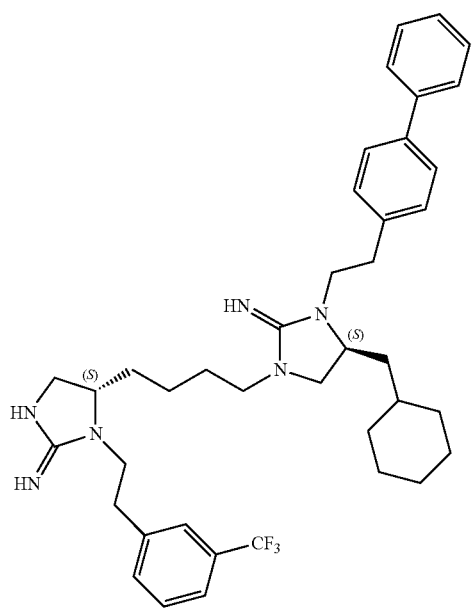
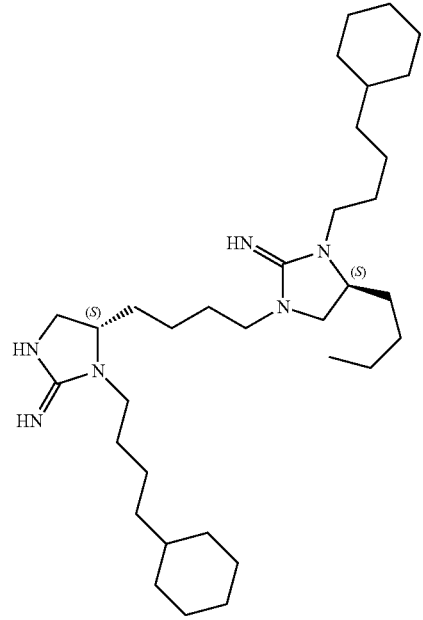
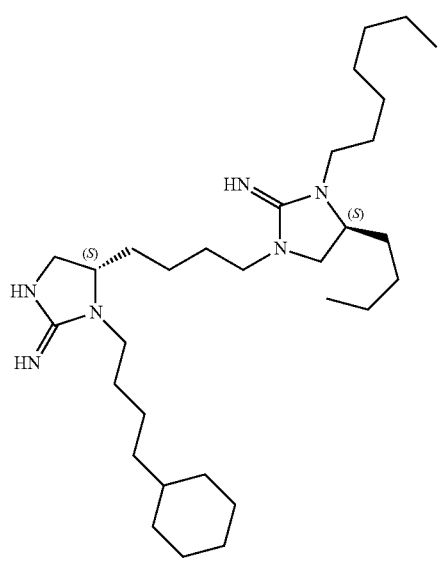
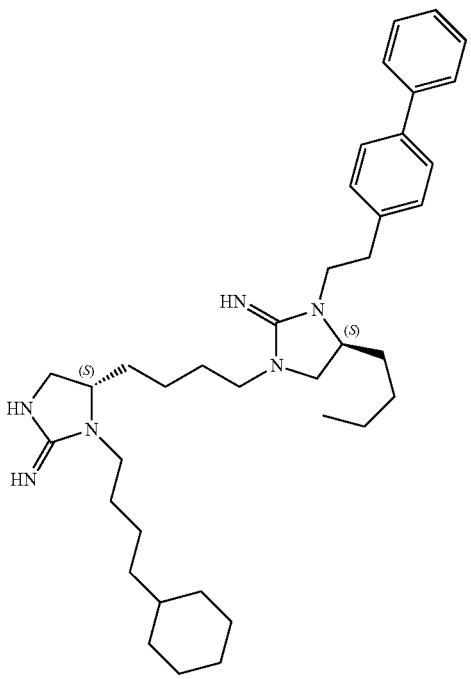

Supplemental TABLE S4c-continued
Structures of individually synthesized bis-cyclic guanidines.
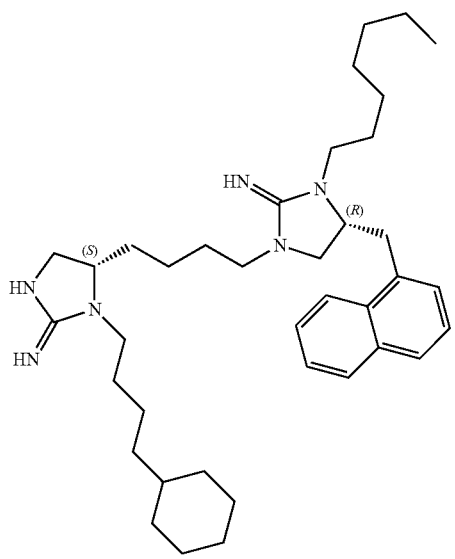
5
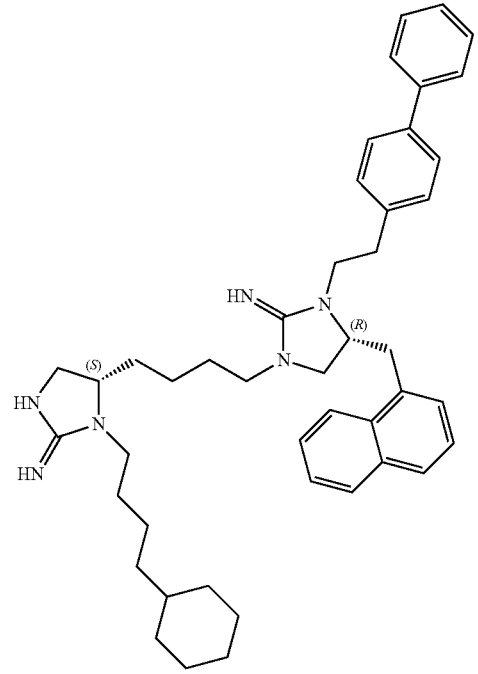
14
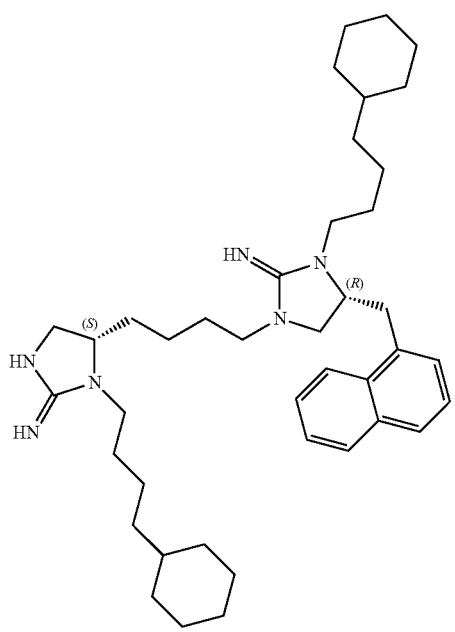
16
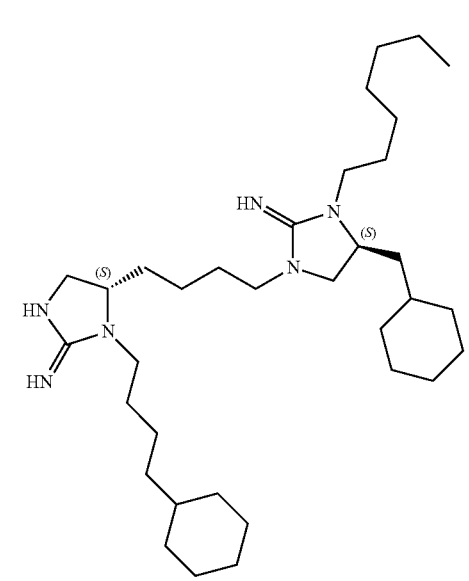

Supplemental TABLE S4c-continued
Structures of individually synthesized bis-cyclic guanidines.
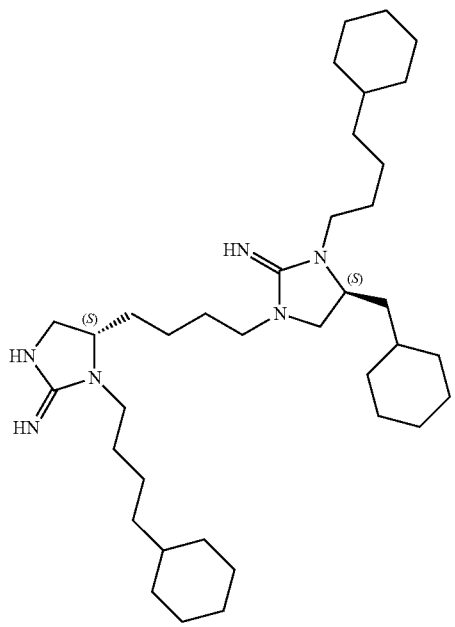
18
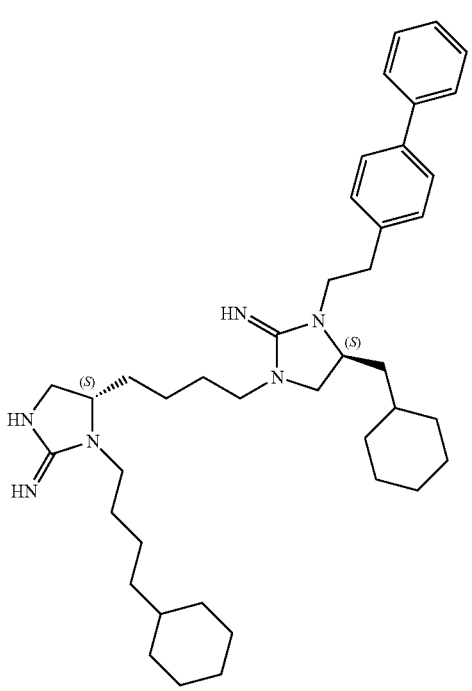
Supplemental TABLE S4c-continued
Structures of individually synthesized bis-cyclic guanidines.
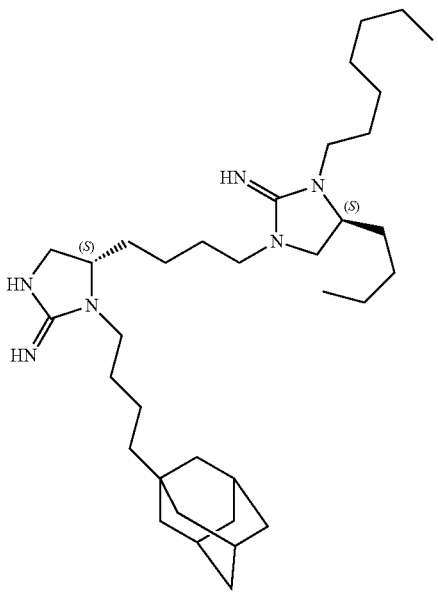
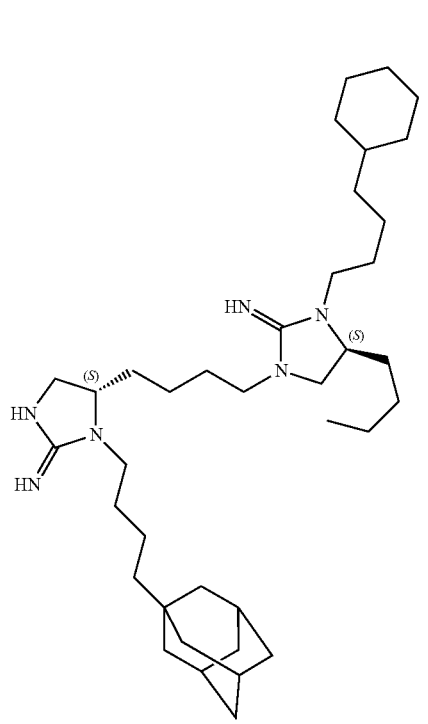

Supplemental TABLE S4c-continued
Structures of individually synthesized bis-cyclic guanidines.
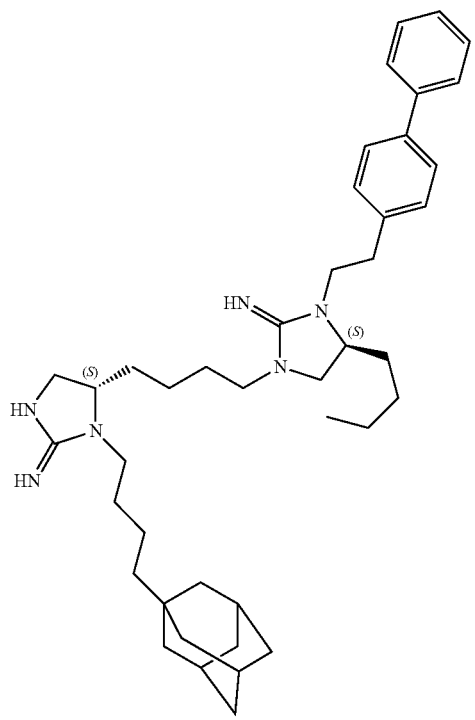
5
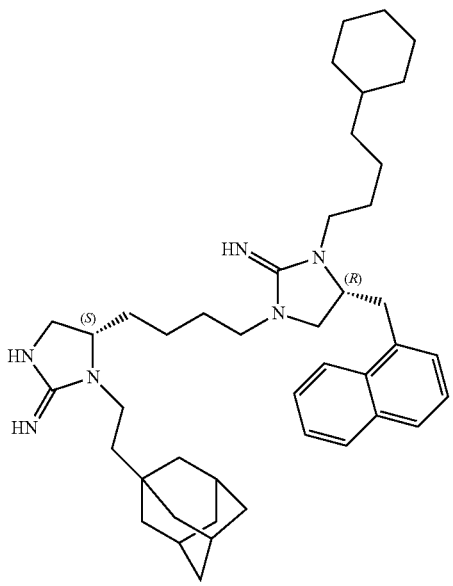
22
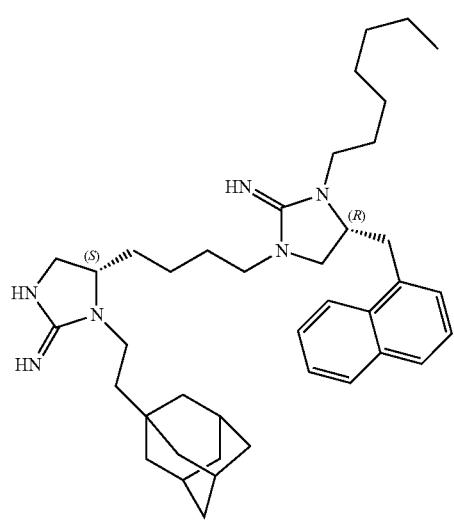
23
24
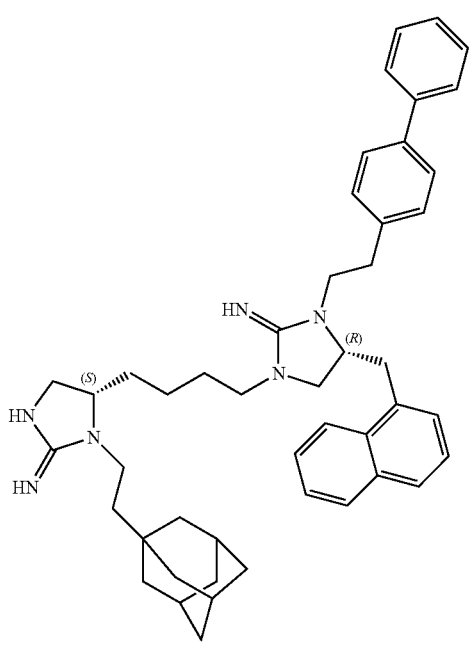
25

Supplemental TABLE S4c-continued
Structures of individually synthesized bis-cyclic guanidines.
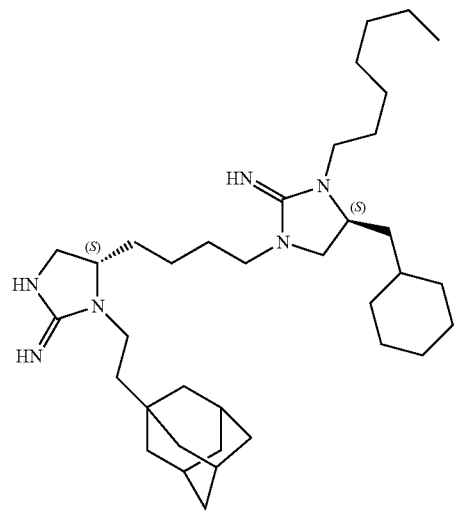
5
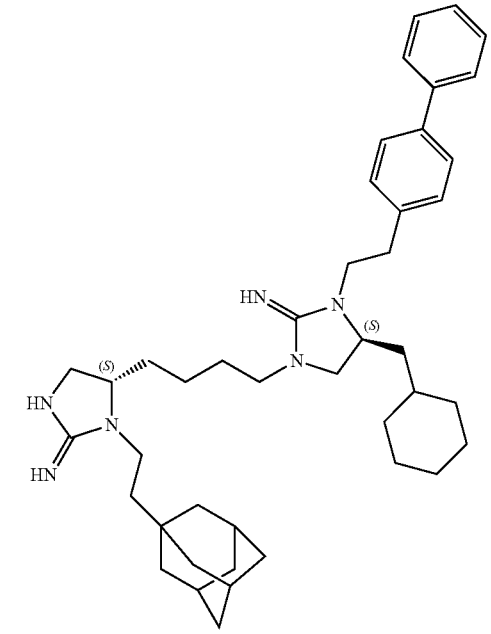
26
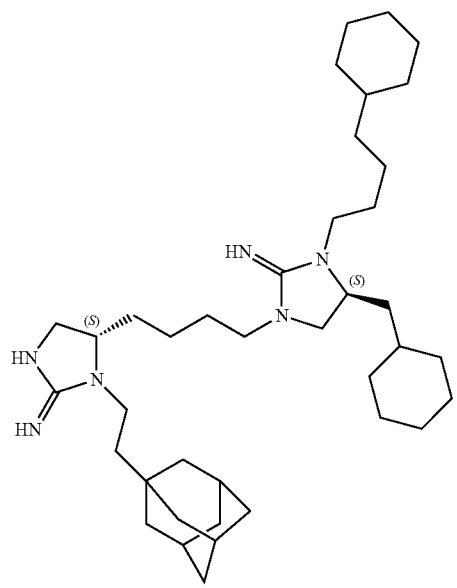
Supplemental TABLE S4c-continued
Structures of individually synthesized bis-cyclic guanidines.
28
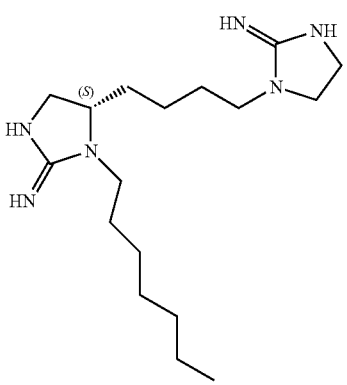
29
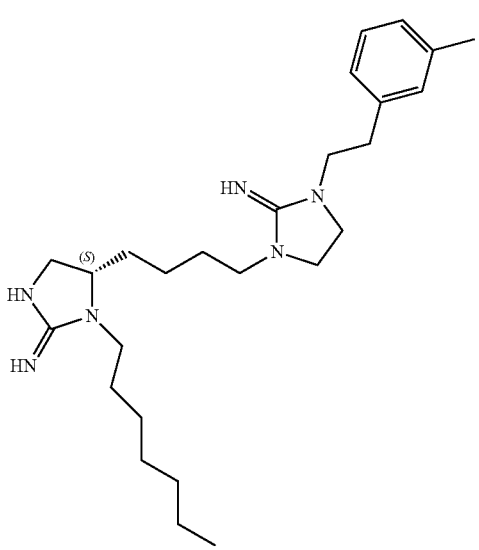

Supplemental TABLE S4c-continued
Structures of individually synthesized bis-cyclic guanidines.
5
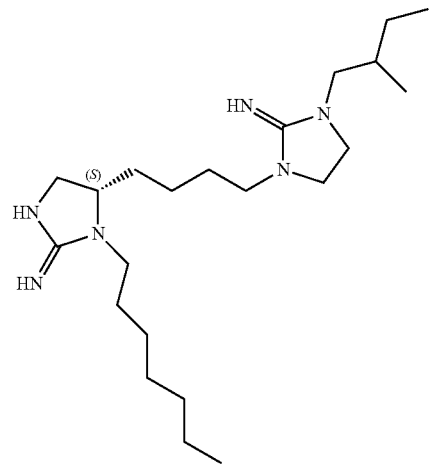
31
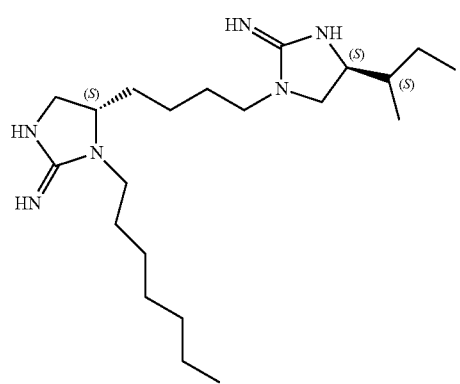
32
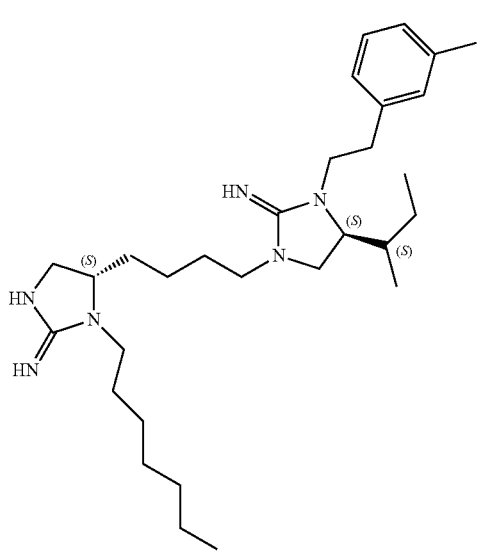
Supplemental TABLE S4c-continued
Structures of individually synthesized bis-cyclic guanidines.
6
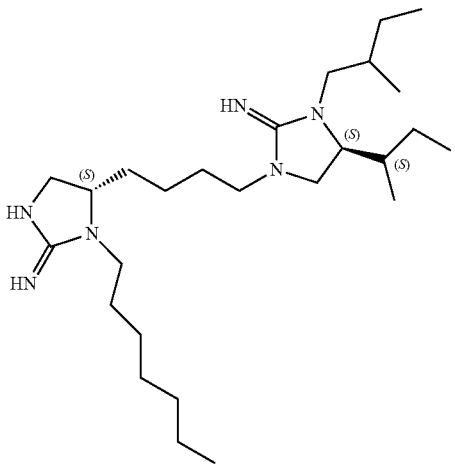
34
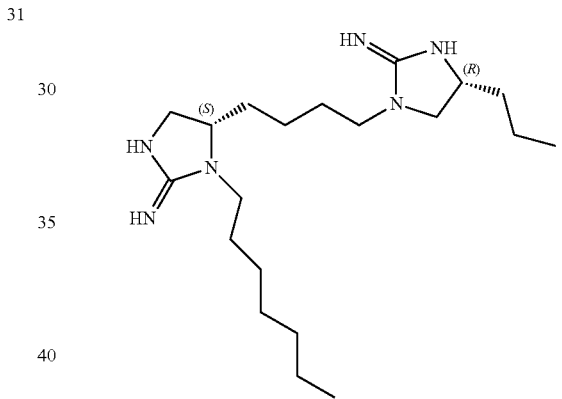
35
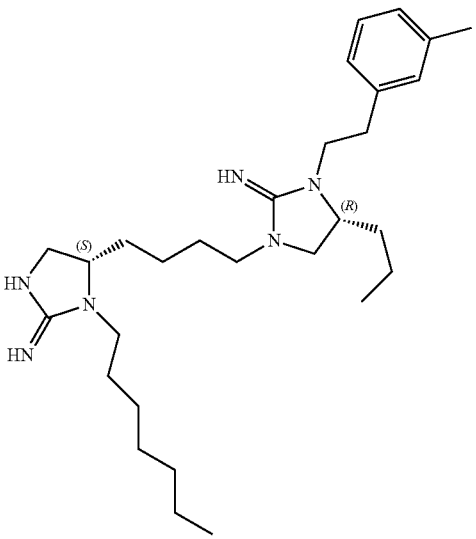

Supplemental TABLE S4c-continued
Structures of individually synthesized bis-cyclic guanidines.
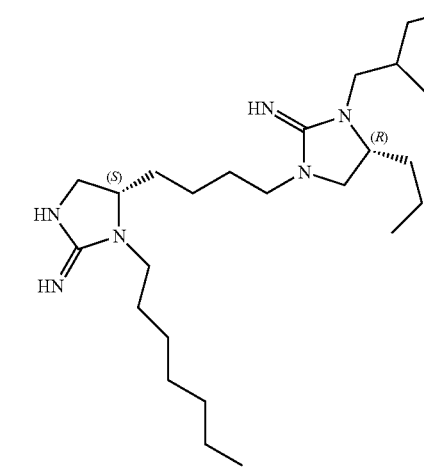
5
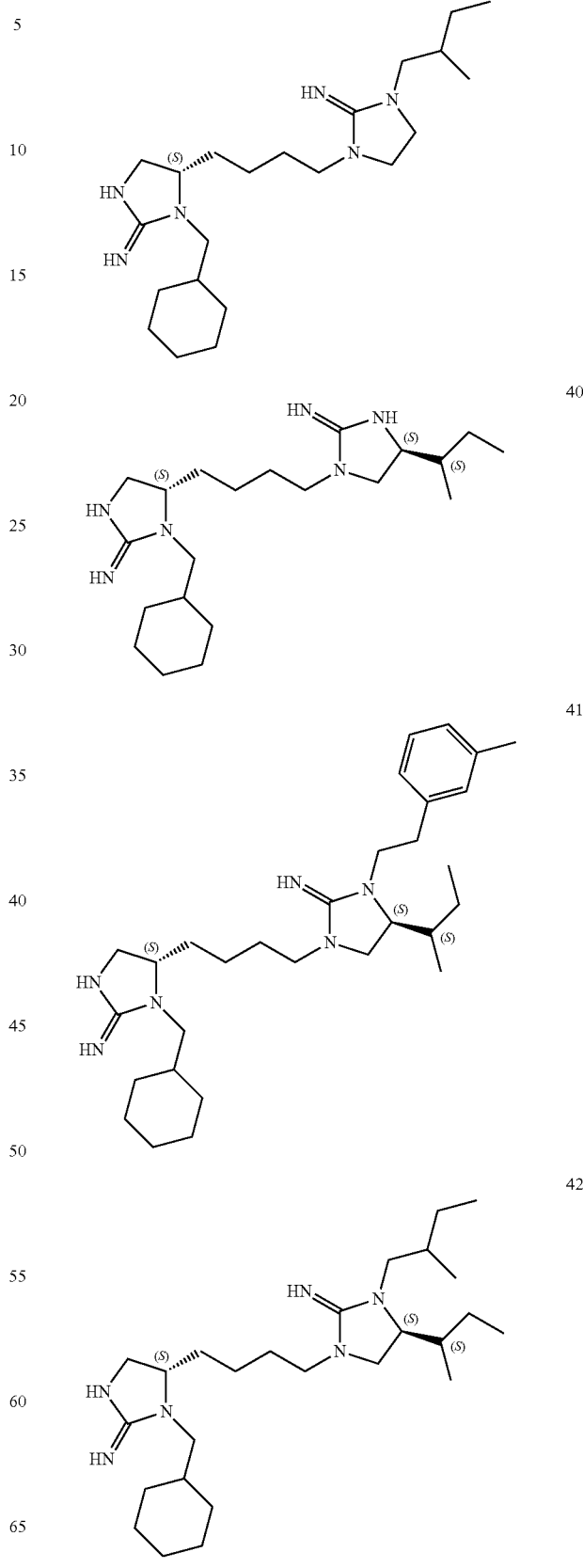
37
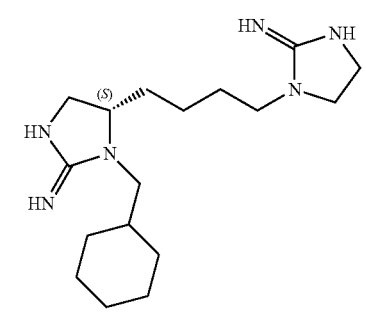
38
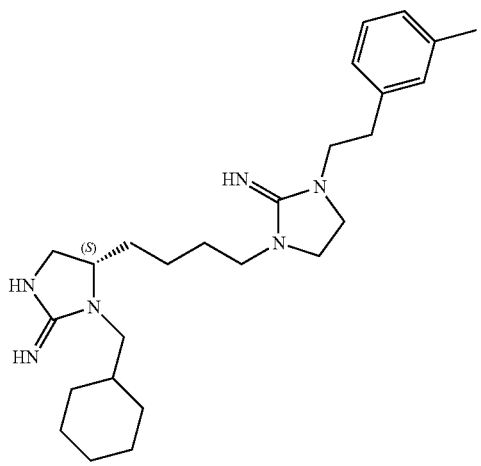
39

Supplemental TABLE S4c-continued
Structures of individually synthesized bis-cyclic guanidines.
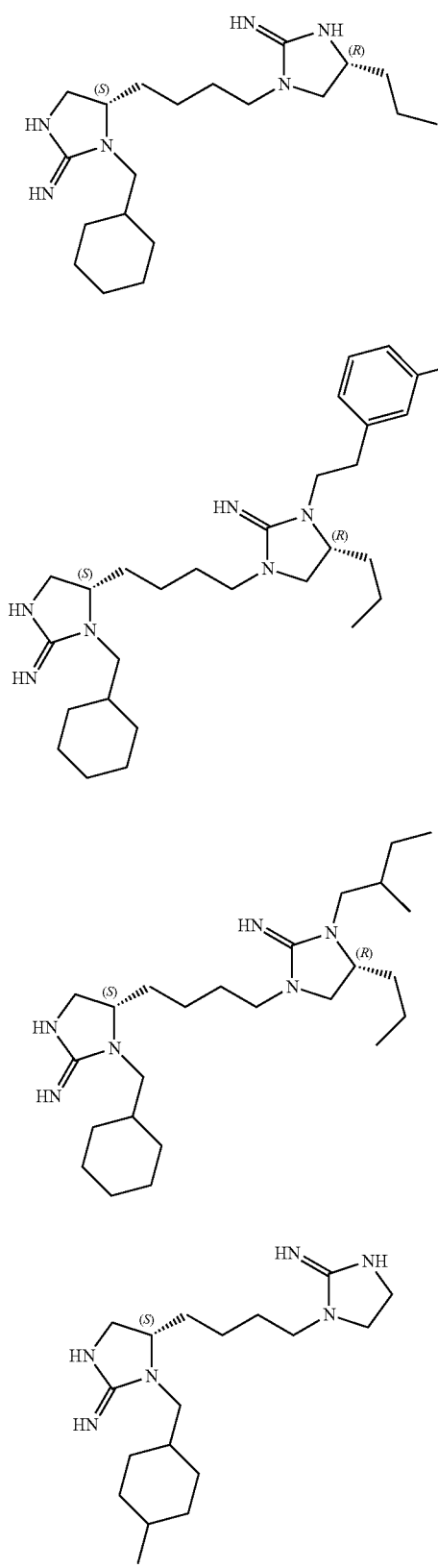
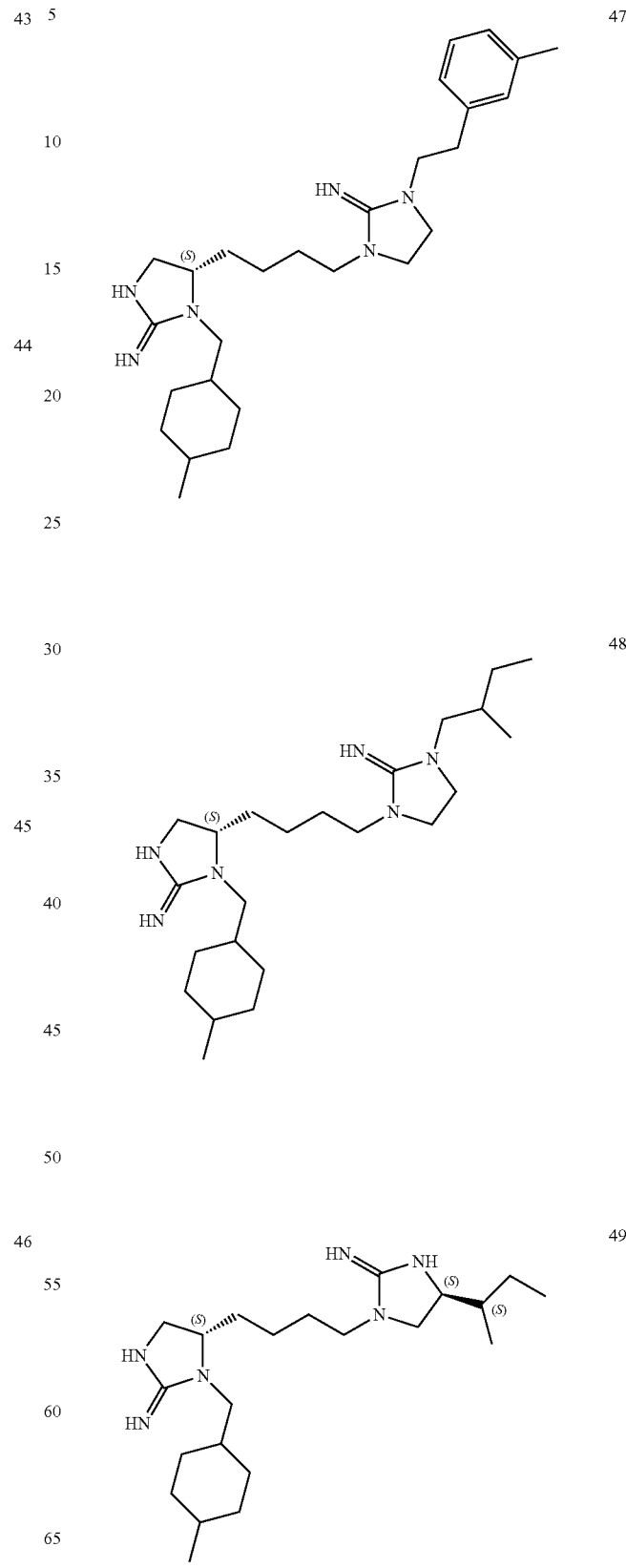

Supplemental TABLE S4c-continued

Structures of individually synthesized bis-cyclic guanidines.

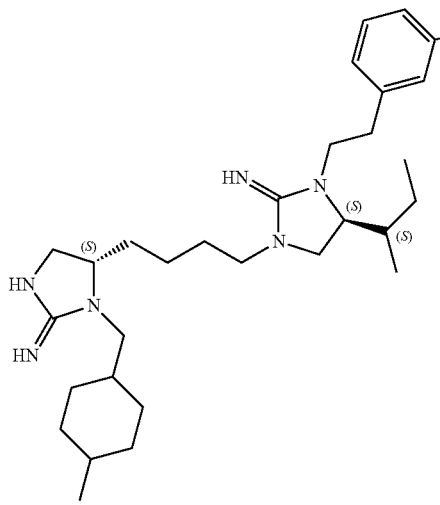

51

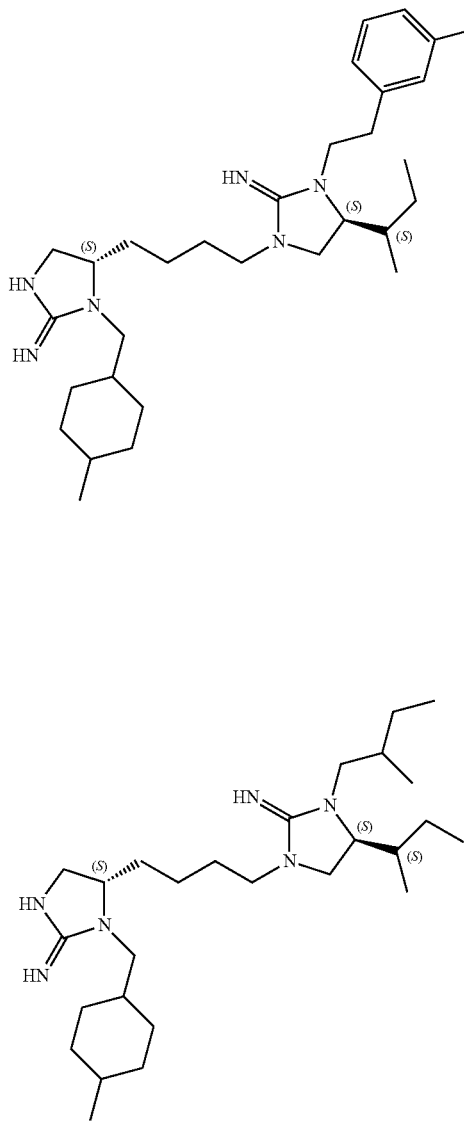

52

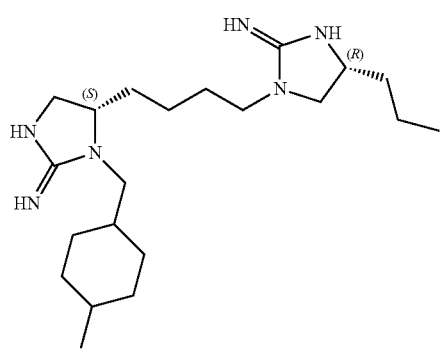

Supplemental TABLE S4c-continued

Structures of individually synthesized bis-cyclic guanidines.

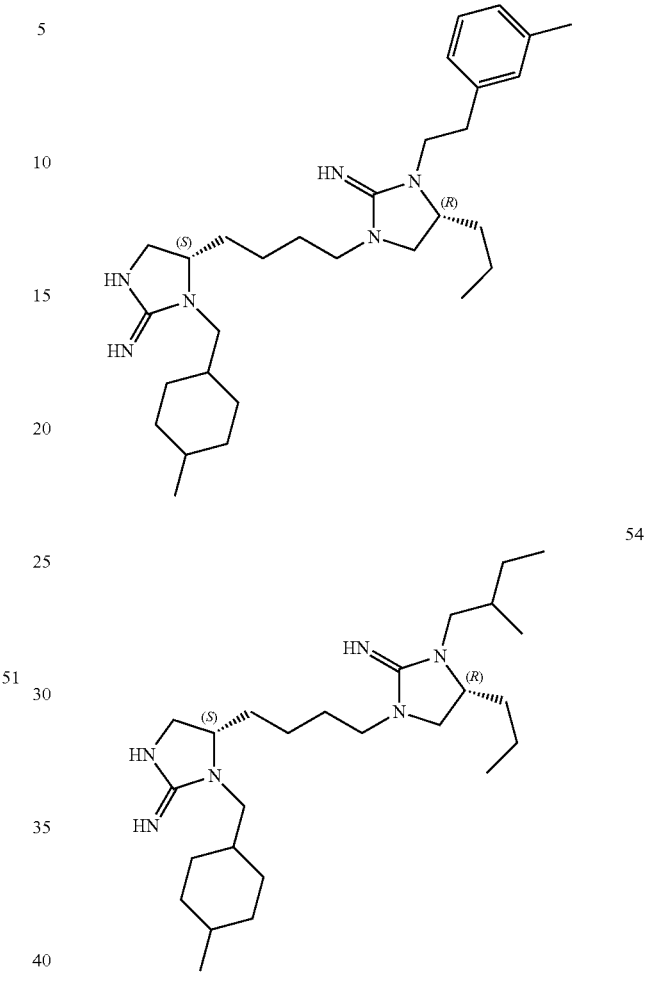

54

SUPPLEMENTAL TABLE S5

Minimal inhibitory concentrations of lead bis-cyclic guanidine against the entire panel of ESKAPE pathogens.

| Isolate | 1 [MIC μM] | 2 [MIC μM] | 7 [MIC μM] | 16 [MIC μM] | 19 [MIC μM] |
|---|---|---|---|---|---|
| *E. faecium* | | | | | |
| 1451 | 2.0 | 2.0 | 2.0 | 2.0 | 2.0 |
| 1406 | 2.0 | 2.0 | 2.0 | 2.0 | 2.0 |
| 1407 | 2.0 | 2.0 | 2.0 | 2.0 | 2.0 |
| 1432 | 2.0 | 2.0 | 2.0 | 2.0 | 2.0 |
| 1438 | 2.0 | 2.0 | 2.0 | 2.0 | 2.0 |
| 1439 | 2.0 | 2.0 | 2.0 | 2.0 | 2.0 |
| 1443 | 2.0 | 2.0 | 2.0 | 2.0 | 2.0 |
| 1444 | 2.0 | 2.0 | 2.0 | 2.0 | 2.0 |
| 1449 | 2.0 | 2.0 | 2.0 | 2.0 | 2.0 |
| 1450 | 2.0 | 2.0 | 2.0 | 2.0 | 2.0 |
| *S. aureus* | | | | | |
| 1043 | 2.0 | 2.0 | 2.0 | 2.0 | 2.0 |
| 1049 | 2.0 | 2.0 | 2.0 | 2.0 | 2.0 |
| 626 | 2.0 | 2.0 | 2.0 | 2.0 | 2.0 |
| 690 | 2.0 | 2.0 | 2.0 | 2.0 | 2.0 |
| 693 | 2.0 | 2.0 | 2.0 | 2.0 | 2.0 |
| 635 | 2.0 | 2.0 | 2.0 | 2.0 | 2.0 |
| 648 | 2.0 | 2.0 | 2.0 | 2.0 | 2.0 |

SUPPLEMENTAL TABLE S5-continued

Minimal inhibitory concentrations of lead bis-cyclic guanidine against the entire panel of ESKAPE pathogens.

| Isolate | 1 [MIC μM] | 2 [MIC μM] | 7 [MIC μM] | 16 [MIC μM] | 19 [MIC μM] |
|---|---|---|---|---|---|
| 715 | 2.0 | 2.0 | 2.0 | 2.0 | 2.0 |
| 728 | 2.0 | 2.0 | 2.0 | 2.0 | 2.0 |
| 542 | 2.0 | 2.0 | 2.0 | 2.0 | 2.0 |
| 834 | 2.0 | 2.0 | 2.0 | 2.0 | 2.0 |
| *K. pneumoniae* | | | | | |
| 1411 | 2.0 | 2.0 | 2.0 | 2.0 | 2.0 |
| 1433 | 2.0 | 2.0 | 2.0 | 2.0 | 2.0 |
| 1434 | 5.0 | 3.0 | 5.0 | 5.0 | 5.0 |
| 1440 | 2.0 | 5.0 | 3.0 | 3.0 | 3.0 |
| 1441 | 2.0 | 2.0 | 2.0 | 2.0 | 2.0 |
| 1408 | 2.0 | 2.0 | 2.0 | 2.0 | 2.0 |
| 1409 | 3.0 | 3.0 | 3.0 | 3.0 | 3.0 |
| 1410 | 3.0 | 2.0 | 2.0 | 3.0 | 3.0 |
| 1412 | 5.0 | 2.0 | 2.0 | 3.0 | 3.0 |
| 1413 | 3.0 | 2.0 | 2.0 | 3.0 | 3.0 |
| *A. baumannii* | | | | | |
| 1403 | 2.0 | 2.0 | 2.0 | 2.0 | 2.0 |
| 1643 | 2.0 | 2.0 | 2.0 | 2.0 | 2.0 |
| 1644 | 2.0 | 2.0 | 2.0 | 2.0 | 2.0 |
| 1647 | 2.0 | 2.0 | 2.0 | 2.0 | 2.0 |
| 1648 | 2.0 | 2.0 | 2.0 | 2.0 | 2.0 |
| 1649 | 2.0 | 2.0 | 2.0 | 2.0 | 2.0 |
| 1650 | 2.0 | 2.0 | 2.0 | 2.0 | 2.0 |
| 1651 | 2.0 | 2.0 | 2.0 | 2.0 | 2.0 |
| 1653 | 2.0 | 2.0 | 2.0 | 2.0 | 2.0 |
| 1654 | 2.0 | 2.0 | 2.0 | 2.0 | 2.0 |
| *P. aeruginosa* | | | | | |
| 1414 | 5.0 | 3.0 | 3.0 | 3.0 | 5.0 |
| 1415 | 5.0 | 3.0 | 3.0 | 3.0 | 5.0 |
| 1416 | 5.0 | 2.0 | 2.0 | 2.0 | 3.0 |
| 1417 | 5.0 | 3.0 | 3.0 | 3.0 | 3.0 |
| 1418 | 7.0 | 7.0 | 7.0 | 7.0 | 7.0 |
| 1419 | 5.0 | 3.0 | 3.0 | 3.0 | 3.0 |
| 1420 | 5.0 | 3.0 | 5.0 | 3.0 | 5.0 |
| 1421 | 5.0 | 3.0 | 2.0 | 3.0 | 5.0 |
| 1422 | 5.0 | 3.0 | 5.0 | 3.0 | 5.0 |
| 1423 | 2.0 | 2.0 | 2.0 | 2.0 | 2.0 |
| *E. cloacae* | | | | | |
| 1404 | 2.0 | 2.0 | 2.0 | 2.0 | 2.0 |
| 1405 | 5.0 | 2.0 | 2.0 | 2.0 | 2.0 |
| 1430 | 3.0 | 2.0 | 2.0 | 2.0 | 3.0 |
| 1431 | 5.0 | 2.0 | 2.0 | 2.0 | 2.0 |
| 1445 | 3.0 | 2.0 | 2.0 | 2.0 | 3.0 |
| 1446 | 7.0 | 7.0 | 5.0 | 5.0 | 5.0 |
| 1447 | 5.0 | 3.0 | 2.0 | 2.0 | 2.0 |
| 1448 | 3.0 | 3.0 | 2.0 | 2.0 | 2.0 |
| 1454 | 3.0 | 2.0 | 2.0 | 2.0 | 2.0 |
| 1455 | 2.0 | 2.0 | 2.0 | 2.0 | 2.0 |

MIC values were determined for each of the 5 lead agents against the entire collection of ESKAPE pathogens. Strain information is included in supplemental table S6.

SUPPLEMENTAL TABLE S6

Clinical ESKAPE strains used in this study.

| Strain name | Identifying Features | Provenance | References |
|---|---|---|---|
| *E. faecium* | | | |
| 1451 | R = Gentamycin, Penicillin G, Tetracycline, Daptomycin<br>S = Vancomycin, Linezolid | Moffitt Cancer Center Urine | This Study |
| 1406 | R = Penicillin G, Tetracycline, Daptomycin, Vancomycin, Linezolid<br>S = Gentamycin | Moffitt Cancer Center VRE Screen | This Study |
| 1407 | R = Gentamycin, Penicillin G, Tetracycline, Daptomycin, Vancomycin, Linezolid | Moffitt Cancer Center Urine | This Study |
| 1432 | R = Gentamycin, Penicillin G, Tetracycline, Daptomycin, Vancomycin<br>S = Linezolid | Moffitt Cancer Center Urine | This Study |
| 1438 | R = Gentamycin, Penicillin G, Tetracycline, Daptomycin, Vancomycin, Linezolid | Moffitt Cancer Center VRE Screen | This Study |
| 1439 | R = Gentamycin, Penicillin G, Tetracycline, Daptomycin, Vancomycin, Linezolid | Moffitt Cancer Center VRE Screen | This Study |
| 1443 | R = Gentamycin, Penicillin G, Tetracycline, Daptomycin, Vancomycin, Linezolid | Moffitt Cancer Center VRE Screen | This Study |
| 1444 | R = Gentamycin, Penicillin G, Tetracycline, Daptomycin, Vancomycin<br>S = Linezolid | Moffitt Cancer Center Tissue | This Study |
| 1449* | R = Gentamycin, Penicillin G, Tetracycline, Daptomycin, Vancomycin, Linezolid | Moffitt Cancer Center Rectum | This Study |
| 1450 | R = Gentamycin, Penicillin G, Tetracycline, Daptomycin, Vancomycin, Linezolid | Moffitt Cancer Center Rectum | This Study |
| *S. aureus* | | | |
| 1043 | R = Ampicillin, Azithromycin, Cethromycin, Erythromycin, Penicillin<br>S = Gentamycin, Oxacillin, Sulfamethoxazole, Rifampin, Tetracycline | University of Washington Medical Center (WA-UW-04-008) Sputum | This Study |

SUPPLEMENTAL TABLE S6-continued

Clinical ESKAPE strains used in this study.

| Strain name | Identifying Features | Provenance | References |
|---|---|---|---|
| 1049 | R = Ampicillin, Azithromycin, Cethromycin, Erythromycin, Penicillin<br>S = Gentamycin, Oxacillin, Sulfamethoxazole, Rifampin, Tetracycline | University of Washington Medical Center (WA-UW-04-014) Buttock skin | This Study |
| 626 | R = Ampicillin, Azithromycin, Chloramphenicol, Clindamycin, Cethromycin, Erythromycin, Penicillin<br>S = Gentamycin, Oxacillin, Sulfamethoxazole, Rifampin, Tetracycline | Tampa General Hospital Nose-Throat | This Study |
| 690 | R = Ampicillin, Azithromycin, Chloramphenicol, Cethromycin, Erythromycin, Penicillin<br>S = Gentamycin, Oxacillin, Sulfamethoxazole, Rifampin, Tetracycline | Tampa General Hospital (FL-TGH-04-056) Nose | This Study |
| 693 | R = Ampicillin, Azithromycin, Chloramphenicol, Cethromycin, Erythromycin, Penicillin<br>S = Gentamycin, Oxacillin, Sulfamethoxazole, Rifampin, Tetracycline | Tampa General Hospital (FL-TGH-04-059) Nasal | This Study |
| 635* | R = Ampicillin, Azithromycin, Chloramphenicol, Clindamycin, Cethromycin, Erythromycin, Penicillin<br>S = Gentamycin, Oxacillin, Sulfamethoxazole, Rifampin, Tetracycline | Tampa General Hospital (FL-TGH-03-021-B) Blood | Carroll et al. (2013) |
| 648 | R = Ampicillin, Chloramphenicol, Penicillin, Gentamycin, Tetracycline<br>S = Oxacillin, Sulfamethoxazole, Rifampin, Tetracycline, Erythromycin | Tampa General Hospital Blood | This Study |
| 715 | R = Ampicillin, Azithromycin, Cethromycin, Erythromycin, Penicillin, Chloramphenicol<br>S = Gentamycin, Oxacillin, Sulfamethoxazole, Rifampin, Tetracycline | Tampa General Hospital Feces | This Study |
| 728 | R = Ampicillin, Azithromycin, Cethromycin, Erythromycin, Penicillin<br>S = Gentamycin, Oxacillin, Sulfamethoxazole, Rifampin, Tetracycline | Tampa General Hospital (FL-TGH-04-086-B) Blood | This Study |
| 542 | R = Ampicillin, Azithromycin, Cethromycin, Erythromycin, Penicillin<br>S = Gentamycin, Oxacillin, Sulfamethoxazole, Rifampin, Tetracycline | Harborview Medical Center WA (WA-HMC-03-47436) Blood | This Study |
| FPR 3757# | R = β lactams, erythromycin, clindamycin, tetracycline, ciprofloxacin, mupirocin, doxycycline<br>S = trimethoprim-sulfamethoxazole | | Diep et al. (2006) |

*K. pneumoniae*

| 1411 | R = Tetracycline, Ciprofloxacin, Ampicillin<br>S = Chloramphenicol, Gentamycin, Imepenem | Moffitt Cancer Center Stool | This Study |
|---|---|---|---|
| 1433* | R = Tetracycline, Ciprofloxacin, Ampicillin, Imepenem<br>S = Chloramphenicol, Gentamycin | Moffitt Cancer Center Urine | This Study |
| 1434 | R = Tetracycline, Ciprofloxacin, Ampicillin, Imepenem<br>S = Chloramphenicol, Gentamycin | Moffitt Cancer Center Urine | This Study |
| 1440 | R = Tetracycline, Gentamycin, Ciprofloxacin, Ampicillin, Imepenem<br>S = Chloramphenicol | Moffitt Cancer Center Urine | This Study |
| 1441 | R = Tetracycline, Gentamycin, Ciprofloxacin, Ampicillin, Imepenem<br>S = Chloramphenicol | Moffitt Cancer Center Fluid | This Study |
| 1408 | R = Tetracycline, Gentamycin, Ciprofloxacin, Ampicillin<br>S = Chloramphenicol, Imepenem | Moffitt Cancer Center Respiratory | This Study |
| 1409 | R = Tetracycline, Gentamycin, Ciprofloxacin, Ampicillin<br>S = Chloramphenicol, Imepenem | Moffitt Cancer Center Wound | This Study |
| 1410 | R = Tetracycline, Gentamycin, Ciprofloxacin, Ampicillin<br>S = Chloramphenicol, Imepenem | Moffitt Cancer Center Blood | This Study |

SUPPLEMENTAL TABLE S6-continued

Clinical ESKAPE strains used in this study.

| Strain name | Identifying Features | Provenance | References |
|---|---|---|---|
| 1412 | R = Tetracycline, Gentamycin, Ciprofloxacin, Ampicillin<br>S = Chloramphenicol, Imepenem | Moffitt Cancer Center<br>Blood | This Study |
| 1413 | R = Tetracycline, Gentamycin, Ciprofloxacin, Ampicillin<br>S = Chloramphenicol, Imepenem | Moffitt Cancer Center<br>Blood | This Study |
| *A. baumannii* | | | |
| 1403* | R = Ampicillin, Ciprofloaxacin, Gentamycin, Polymyxin B, Trimethoprim, Sulfamethoxazole<br>S = Rifampin, Chloramphenicol, Tetracycline, Imepenem | Moffitt Cancer Center<br>Urine | This Study |
| 1643 | R = Ampicillin, Amikacin, Amp-Sulbactam, Aztreonam, Cefepime, Cefotaxime, Ceftazidime, Ceftriaxone, Ciprofloxacin, Chloramphenicol, Gentamycin, Piperacillin, Timentin, Tobramycin, Trimethoprim, Sulfamethoxazole, Levofloxacin<br>S = Imepenem, Meropenem, Polymyxin B, Rifampin | University of Nebraska Medical Center (2006)<br>Sputum<br>PFGE A: 510 | Jacobs et al. (2010) |
| 1644 | R = Ampicillin, Chloramphenicol, Ciprofloxacin<br>S = Gentamycin, Polymyxin B, Rifampin, Tetracycline | ATCC (1968)<br>Blood<br>PFGE C: 17904 | Jacobs et al. (2010) |
| 1647 | R = Gentamycin, Polymyxin B, Ampicillin, Tetracycline, Ciprofloxacin, Chloramphenicol, Sulfamethoxazole<br>S = Rifampin | ATCC (1951)<br>Fetal meningitis<br>PFGE E: 17978 | Jacobs et al. (2010) |
| 1648 | R = Ampicillin, Aztreonam, Chloramphenicol, Ciprofloxacin, Cefotaxime,<br>S = Amikacin, Amp-Sulbactam, Cefepime, Ceftriaxone, Gentamycin, Piperacillin, Timentin, Tobramycin, Trimethoprim, Sulfamethoxazole, Levofloxacin, Polymyxin B, Rifampin, Tetracycline | CDC (TX; 1998)<br>Endotracheal tube<br>PFGE F: 983701 | Jacobs et al. (2010) |
| 1649 | R = Ampicillin, Aztreonam, Cefotaxime, Sulfamethoxazole, Ceftriaxone, Tetracycline<br>S = Amikacin, Amp-Sulbactam, Cefepime,, Gentamycin, Piperacillin, Timentin, Tobramycin, Trimethoprim, Levofloxacin, Polymyxin B, Rifampin, Ciprofloxacin, Chloramphenicol | CDC (TX; 1998)<br>Sputum<br>PFGE G: 983702 | Jacobs et al. (2010) |
| 1650 | R = Ampicillin, Aztreonam, Sulfamethoxazole, Tetracycline, Chloramphenicol<br>S = Amikacin, Amp-Sulbactam, Cefepime,, Gentamycin, Piperacillin, Timentin, Tobramycin, Trimethoprim, Levofloxacin, Polymyxin B, Rifampin, Ciprofloxacin, Cefotaxime, Ceftriaxone | CDC (TX; 1998)<br>Tracheal aspirate<br>PFGE H: 983705 | Jacobs et al. (2010) |
| 1651 | R = Ampicillin, Aztreonam, Sulfamethoxazole, Chloramphenicol<br>S = Amikacin, Amp-Sulbactam, Cefepime,, Gentamycin, Piperacillin, Timentin, Tobramycin, Trimethoprim, Levofloxacin, Polymyxin B, Rifampin, Ciprofloxacin, Cefotaxime, Ceftriaxone, Tetracycline | CDC (TX; 1998)<br>Cerebrospinal fluid<br>PFGE I: 983709 | Jacobs et al. (2010) |
| 1653 | R = Ampicillin, Amikacin, Amp-Sulbactam, Aztreonam, Cefepime, Cefotaxime, Ceftazidime, Ceftriaxone, Ciprofloxacin, Gentamycin, Piperacillin, Timentin, Tobramycin, Trimethoprim, Sulfamethoxazole<br>S = Imepenem, Meropenem, Polymyxin B, Rifampin, Levofloxacin | CDC (IN; 2001)<br>Blood<br>PFGE K: 011205 | Jacobs et al. (2010) |
| 1654 | R = Ampicillin, Amikacin, Amp-Sulbactam, Aztreonam, Cefepime, Cefotaxime, Ceftazidime, Ceftriaxone, Ciprofloxacin, Gentamycin, Piperacillin, Tobramycin, Trimethoprim, Sulfamethoxazole, Levofloxacin<br>S = Imepenem, Meropenem, Polymyxin B, Rifampin, Timentin, Chloramphenicol, Tetracycline | CDC (KY; 2007)<br>Unknown<br>PFGE L: 070954 | Jacobs et al. (2010) |
| *P. aeruginosa* | | | |
| 1414 | R = Ampicillin, Polymyxin B, Gentamycin, Chloramphenicol, Imepenem, Ciprofloxacin<br>S = Tetracycline | Moffitt Cancer Center<br>Fluid | This Study |

SUPPLEMENTAL TABLE S6-continued

Clinical ESKAPE strains used in this study.

| Strain name | Identifying Features | Provenance | References |
|---|---|---|---|
| 1415 | R = Ampicillin, Polymyxin B, Gentamycin, Chloramphenicol, Imepenem, Ciprofloxacin<br>S = Tetracycline | Moffitt Cancer Center Fluid | This Study |
| 1416 | R = Ampicillin, Polymyxin B, Gentamycin, Chloramphenicol, Imepenem<br>S = Ciprofloxacin, Tetracycline | Moffitt Cancer Center Fluid | This Study |
| 1417 | R = Ampicillin, Polymyxin B, Gentamycin, Chloramphenicol, Imepenem<br>S = Ciprofloxacin, Tetracycline | Moffitt Cancer Center Wound | This Study |
| 1418 | R = Ampicillin, Polymyxin B, Gentamycin, Chloramphenicol, Imepenem, Ciprofloxacin, Tetracycline | Moffitt Cancer Center Respiratory | This Study |
| 1419 | R = Ampicillin, Polymyxin B, Gentamycin, Chloramphenicol, Imepenem, Ciprofloxacin<br>S = Tetracycline | Moffitt Cancer Center Respiratory | This Study |
| 1420 | R = Ampicillin, Polymyxin B, Gentamycin, Chloramphenicol, Imepenem, Ciprofloxacin<br>S = Tetracycline | Moffitt Cancer Center Urine | This Study |
| 1421 | R = Ampicillin, Polymyxin B, Gentamycin, Chloramphenicol, Imepenem, Ciprofloxacin<br>S = Tetracycline | Moffitt Cancer Center Respiratory | This Study |
| 1422 | R = Ampicillin, Polymyxin B, Gentamycin, Chloramphenicol, Imepenem, Ciprofloxacin<br>S = Tetracycline | Moffitt Cancer Center Fluid | This Study |
| 1423* | R = Ampicillin, Polymyxin B, Gentamycin, Chloramphenicol, Imepenem, Ciprofloxacin, Tetracycline | Moffitt Cancer Center Urine | This Study |
| E. cloacae | | | |
| 1404 | R = Ampicillin, Chloamphenicol, Imepenem, Gentamycin, Polymyxin B, Ciprofloxacin<br>S = Tetracycline | Moffitt Cancer Center Urine | This Study |
| 1405 | R = Ampicillin, Chloamphenicol, Imepenem, Gentamycin, Polymyxin B, Ciprofloxacin, Tetracycline | Moffitt Cancer Center Wound | This Study |
| 1430 | R = Ampicillin, Chloamphenicol, Imepenem, Gentamycin<br>S = Polymyxin B, Ciprofloxacin, Tetracycline | Moffitt Cancer Center Blood | This Study |
| 1431 | R = Ampicillin, Chloamphenicol, Imepenem, Gentamycin, Polymyxin B, Ciprofloxacin<br>S = Tetracycline | Moffitt Cancer Center Urine | This Study |
| 1445 | R = Ampicillin, Chloamphenicol, Imepenem, Gentamycin, Polymyxin B, Ciprofloxacin<br>S = Tetracycline | Moffitt Cancer Center Sputum | This Study |
| 1446 | R = Ampicillin, Chloamphenicol, Imepenem, Gentamycin, Polymyxin B, Ciprofloxacin<br>S = Tetracycline | Moffitt Cancer Center Urine | This Study |
| 1447 | R = Ampicillin, Chloamphenicol, Imepenem, Gentamycin, Polymyxin B, Ciprofloxacin, Tetracycline | Moffitt Cancer Center Urine | This Study |
| 1448 | R = Ampicillin, Chloamphenicol, Imepenem, Gentamycin, Polymyxin B, Ciprofloxacin, Tetracycline | Moffitt Cancer Center Urine | This Study |
| 1454* | R = Ampicillin, Chloamphenicol, Imepenem, Gentamycin, Polymyxin B, Ciprofloxacin, Tetracycline | Moffitt Cancer Center Urine | This Study |
| 1455 | R = Ampicillin, Chloamphenicol, Imepenem, Gentamycin, Polymyxin B, Ciprofloxacin, Tetracycline | Moffitt Cancer Center Urine | This Study |

The clinical strain set used in this study is detailed, alongside drug resistances/sensitivities, provenance and patient site of isolation. R denotes known resistances to given compounds, and S refers to any sensitivity determined.
*= Isolates used for library screening, positional scanning screening, MBC, MBEC and resistance assays.
= Isolate used for the murine model of infection.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

We claim:

1. A pharmaceutical composition comprising a therapeutically effective amount of a bis-cyclic guanidine compound, or a pharmaceutically acceptable salt of bis-cyclic guanidine compound, and a pharmaceutically acceptable carrier, to treat an infection, wherein the bis-cyclic guanidine compound has the following structure:

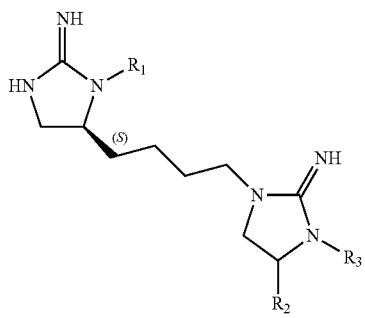

R₁ is selected from the group consisting of: 2-(3-trifluoromethyl-phenyl)-ethyl, cyclohexyl-butyl, and adamantan-1-yl-ethyl;

R₂ is selected from the group consisting of: (S or R)-butyl, (S or R)-2-naphthylmethyl, and (S or R)-cyclohexylmethyl;

R₃ is selected from the group consisting of: heptyl, cyclohexyl-butyl, and 2-biphenyl-4-yl-ethyl; and wherein the infection is caused by one or more bacteria selected from the group consisting of: *Enterococcus faecium, Staphylococcus aureus, Klebsiella pneumoniae, Acinetobacter baumannii, Pseudomonas aeruginosa,* and *Enterobacter cloacae.*

2. The pharmaceutical composition of claim 1, wherein the bis-cyclic guanidine compound is selected from one of the following structures:

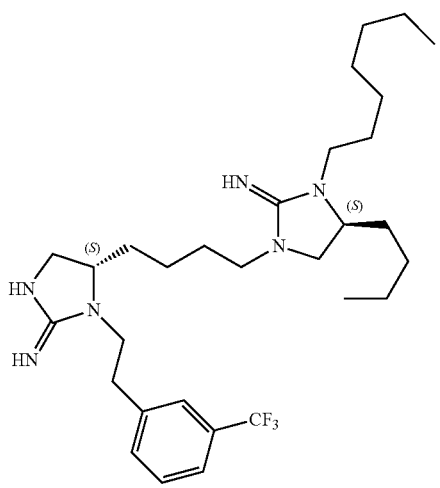

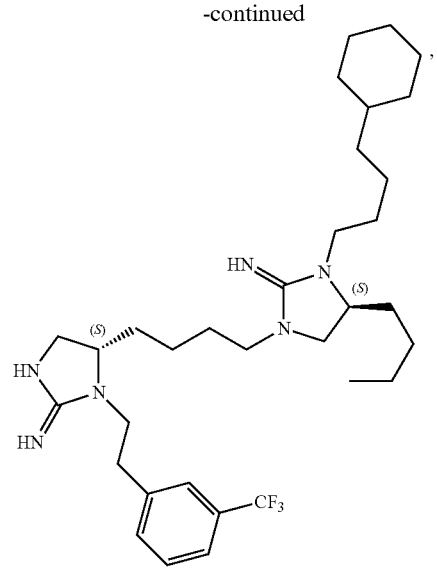

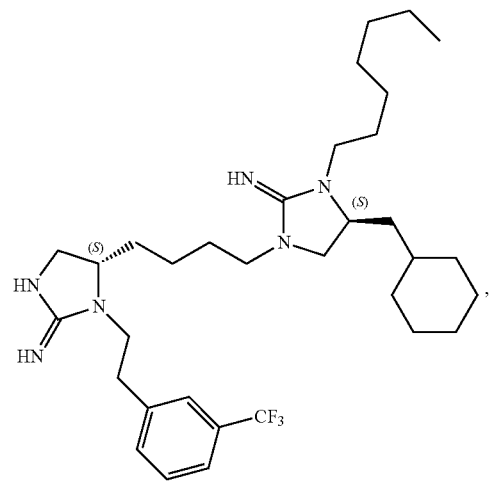

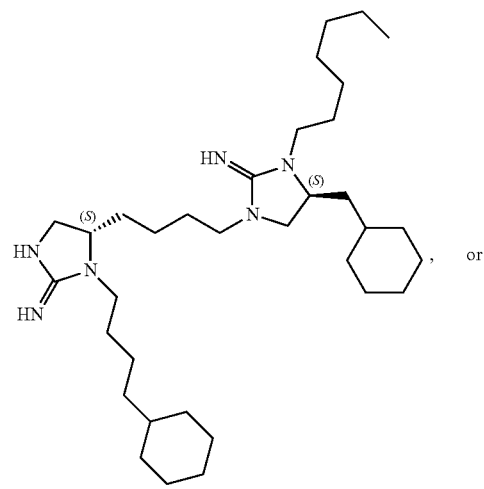

or

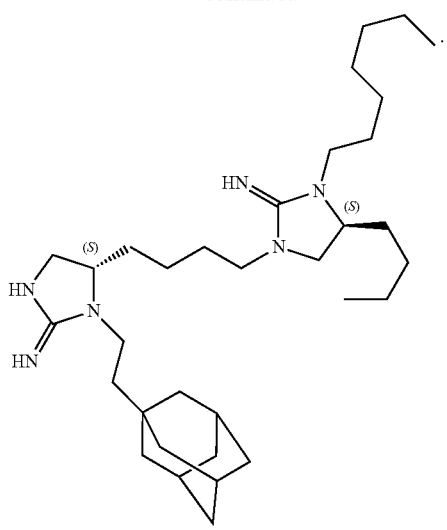

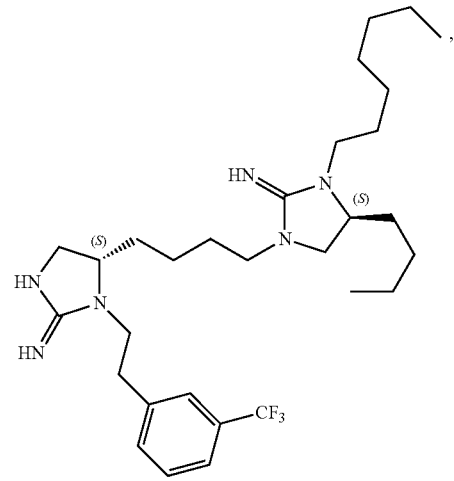

3. A method of treating an infection comprising: delivering to a subject in need thereof, a pharmaceutical composition, wherein the pharmaceutical composition includes a therapeutically effective amount of a bis-cyclic guanidine compound, or a pharmaceutically acceptable salt of the bis-cyclic guanidine compound, and a pharmaceutically acceptable carrier, to treat the infection, wherein the bis-cyclic guanidine compound has the following structure:

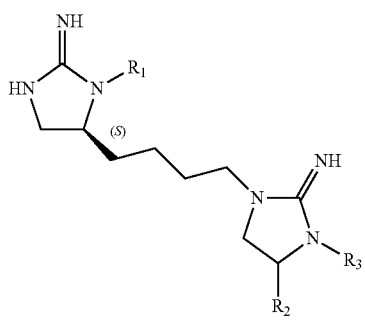

R$_1$ is selected from the group consisting of: 2-(3-trifluoromethyl-phenyl)-ethyl, cyclohexyl-butyl, and adamantan-1-yl-ethyl;

R$_2$ is selected from the group consisting of: (S or R)-butyl, (S or R)-2-naphthylmethyl, and (S or R)-cyclohexylmethyl;

R$_3$ is selected from the group consisting of: heptyl, cyclohexyl-butyl, and 2-biphenyl-4-yl-ethyl; and wherein the infection is caused by one or more bacteria selected from the group consisting of: *Enterococcus faecium, Staphylococcus aureus, Klebsiella pneumoniae, Acinetobacter baumannii, Pseudomonas aeruginosa,* and *Enterobacter cloacae.*

4. The method of claim 3, wherein the pharmaceutical composition is a broad spectrum antibiotic.

5. The method of claim 3, wherein the bis-cyclic guanidine compound is selected from one of the following structures:

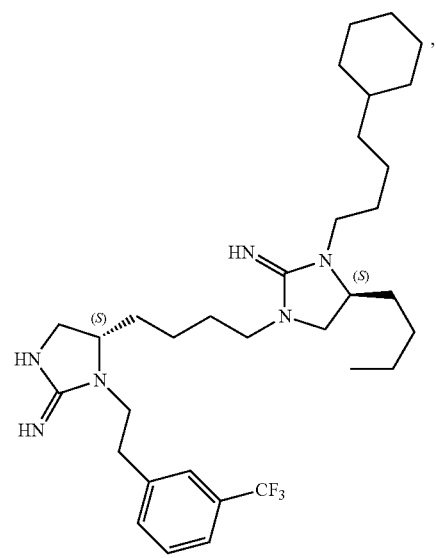

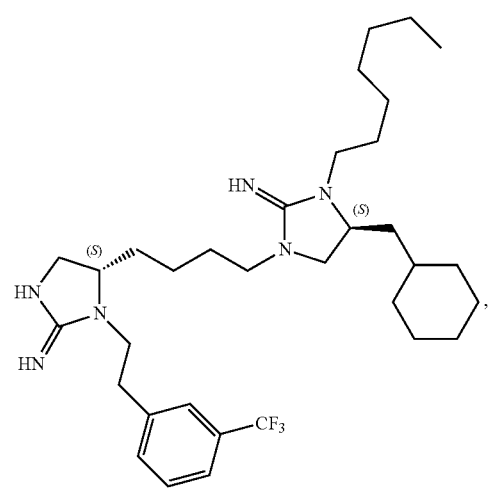

-continued

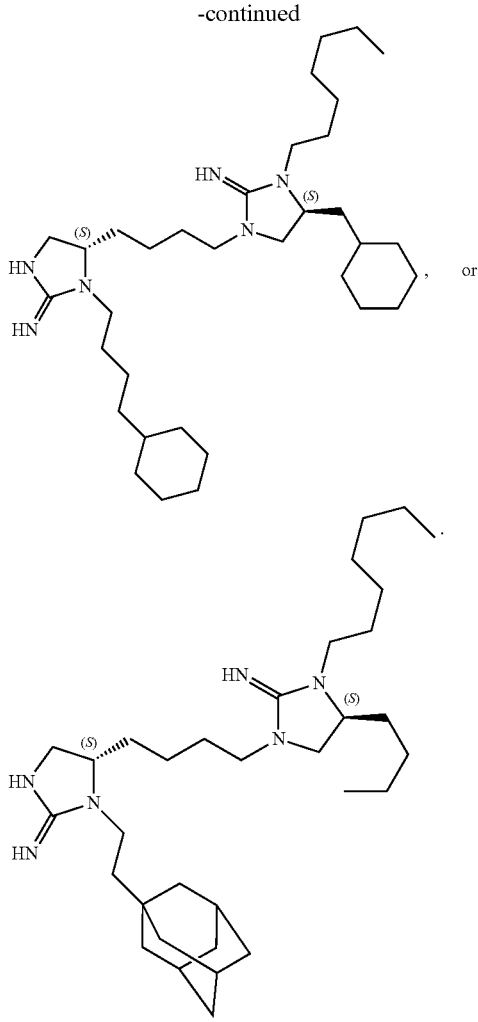

6. A method of inhibiting the growth of a biofilm or the growth of bacteria, comprising:
exposing a surface having a biofilm thereon or exposed to bacteria to a composition comprising a bis-cyclic guanidine compound, wherein the bis-cyclic guanidine compound has the following structure:

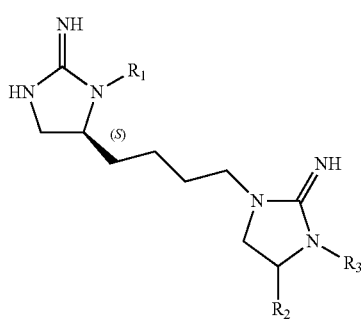

$R_1$ is selected from the group consisting of: 2-(3-trifluoromethyl-phenyl)-ethyl, cyclohexyl-butyl, and adamantan-1-yl-ethyl;

$R_2$ is selected from the group consisting of: (S or R)-butyl, (S or R)-2-naphthylmethyl, and (S or R)-cyclohexylmethyl;

$R_3$ is selected from the group consisting of: heptyl, cyclohexyl-butyl, and 2-biphenyl-4-yl-ethyl; and wherein the biofilm or the bacteria is selected from the group consisting of: *Enterococcus faecium*, *Staphylococcus aureus*, *Klebsiella pneumoniae*, *Acinetobacter baumannii*, *Pseudomonas aeruginosa*, and *Enterobacter cloacae*.

7. The method of claim 6, wherein the bis-cyclic guanidine compound is selected from one of the following structures:

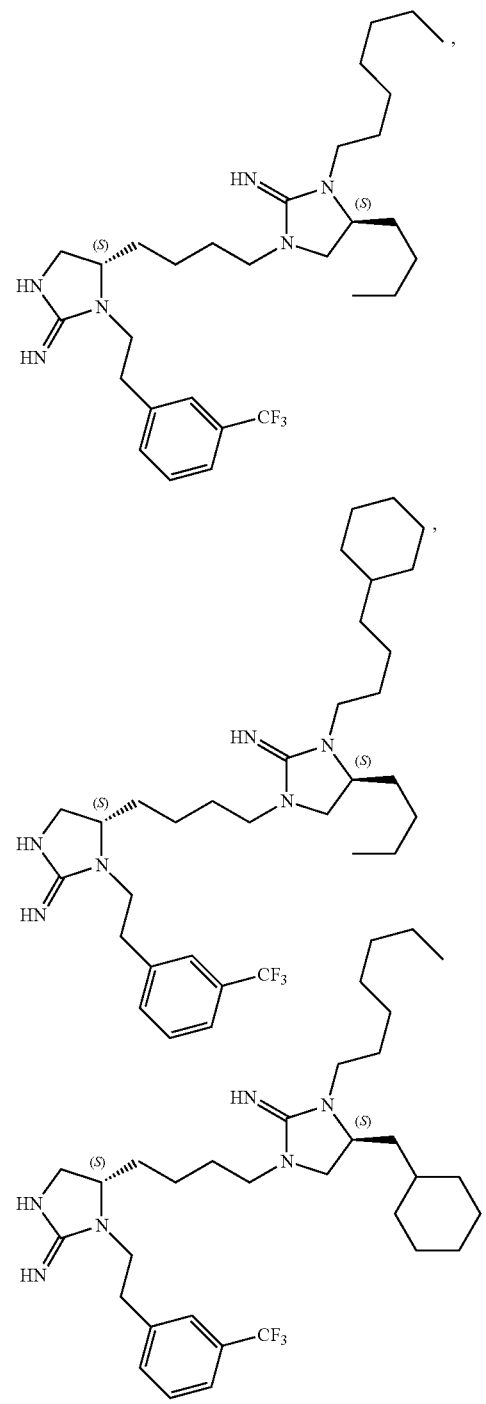

117
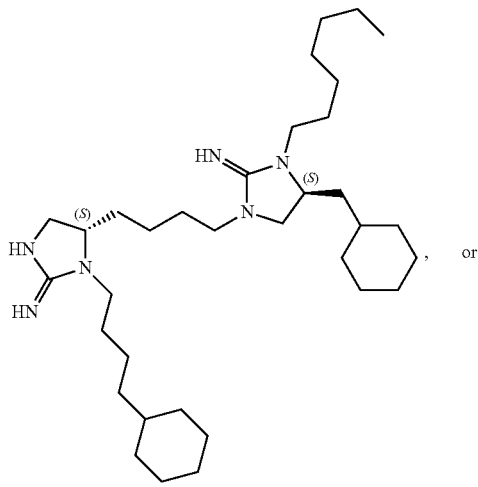
, or
118
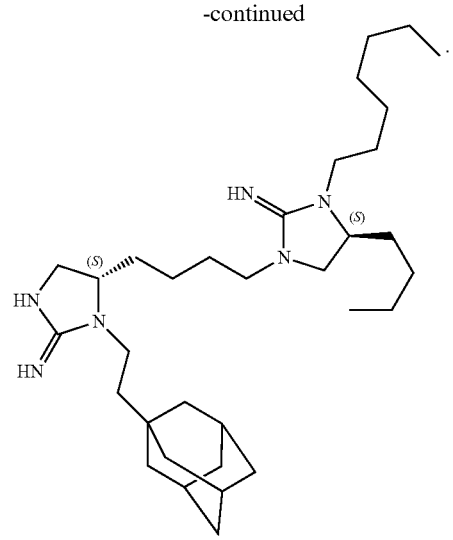
.
* * * * *